United States Patent
Kumada et al.

(10) Patent No.: US 8,618,247 B2
(45) Date of Patent: Dec. 31, 2013

(54) PEPTIDE, USE OF THE PEPTIDE, METHOD FOR THE PRODUCTION OF THE PEPTIDE, SOLID SUPPORT HAVING THE PEPTIDE IMMOBILIZED THEREON, AND METHOD FOR PRODUCTION OF THE SOLID SUPPORT

(75) Inventors: Yoichi Kumada, Kyoto (JP); Michimasa Kishimoto, Kyoto (JP); Yuki Shiritani, Kyoto (JP); Kyoko Hamasaki, Kyoto (JP); Takuhito Ohse, Kawaguchi (JP); Mitsuyasu Koike, Kawaguchi (JP)

(73) Assignees: Enplas Corporation, Saitama (JP); National University Corporation Kyoto Institute of Technology, Kyoto (JP)

( * ) Notice: Subject to any disclaimer, the term of this patent is extended or adjusted under 35 U.S.C. 154(b) by 268 days.

(21) Appl. No.: 12/864,368

(22) PCT Filed: Feb. 12, 2009

(86) PCT No.: PCT/JP2009/000555
§ 371 (c)(1),
(2), (4) Date: Nov. 10, 2010

(87) PCT Pub. No.: WO2009/101807
PCT Pub. Date: Aug. 20, 2009

(65) Prior Publication Data
US 2011/0045538 A1   Feb. 24, 2011

(30) Foreign Application Priority Data

Feb. 14, 2008  (JP) ................................. 2008-033135
Sep. 25, 2008  (JP) ................................. 2008-246068

(51) Int. Cl.
*A61K 38/00* (2006.01)
*C07K 1/00* (2006.01)
*A61K 36/00* (2006.01)
*A23J 1/00* (2006.01)
*C07K 16/00* (2006.01)

(52) U.S. Cl.
USPC ............ 530/300; 530/350; 530/370; 530/412

(58) Field of Classification Search
None
See application file for complete search history.

(56) References Cited

FOREIGN PATENT DOCUMENTS

WO    WO 2005/058959    *   6/2005

OTHER PUBLICATIONS

Kumada et al. Biotechnol. Prog. 2006 22:401-406.*
Immunoassay, p. 1, Sep. 20, 2012.*
Rudikoff et al. PNAS 1982 vol. 79 pp. 1979-1983.*
MacCallum et al. J. Mol. Biol. (1996) 262, 732-745.*
Pascalis et al. The Journal of Immunology (2002) 169, 3076-3084.*
Vajdos et al. JMB (2002) 320, 415-428.*
Kumada et al. Journal of Biotechnology 2007, 127:288-299.*
Kumada et al. Biotechnol. Prog. 2006. 22:401-405.*
Holm et al Molecular Immunology (2007) 44, 1075-1084.*
SEQ ID No. 4 alignment. pp. 1-2, Jun. 22, 2013.*

* cited by examiner

*Primary Examiner* — Chun Dahle
(74) *Attorney, Agent, or Firm* — William C. Schrot; AuerbachSchrot LLC

(57) ABSTRACT

Provided is a peptide containing a variable region and improved in production efficiency.

The peptide contains a variable region to which an antigen-binding site is to be formed and has an amino acid sequence expressing a specific adsorption function to a solid phase at a site closer to the C-terminal than a heavy-chain variable region or at a site closer to the C-terminal than a light-chain variable region.

10 Claims, 17 Drawing Sheets

(a)

(b)

(c)

(d)

(a)

(b)

(a)

(b)

PEPTIDE, USE OF THE PEPTIDE, METHOD FOR THE PRODUCTION OF THE PEPTIDE, SOLID SUPPORT HAVING THE PEPTIDE IMMOBILIZED THEREON, AND METHOD FOR PRODUCTION OF THE SOLID SUPPORT

TECHNICAL FIELD

The present invention relates to a novel peptide, use of the peptide and a method for producing the peptide, and particularly relates to a peptide expressing a binding function specifically to a hydrophilic solid phase, use of the peptide and a method for producing the peptide. Furthermore, the present invention relates to a peptide that can be used for detecting or measuring a compound by use of a solid-phase method and a method for detecting or measuring a compound by using the peptide. Moreover, the present invention relates to a peptide containing a variable region in which an antigen-binding site is to be formed and an immunoglobulin molecule, and further relates to a single-chain antibody (scFv) containing a variable region, a multivalent single-chain antibody (sc(Fv)$_n$), a single-chain antibody fused with a constant region (scFv-Fc), a Fab fragment or an F(ab')$_2$ fragment and a solid phase on which each of these peptides are immobilized, and a method for producing the solid phase.

BACKGROUND ART

An antibody (immunoglobulin) is a protein specifically binding to an antigen and plays the leading role in humoral immunity in-vivo. FIG. 6(a) is a schematic view showing a basic structure of an antibody (immunoglobulin). An antibody molecule 61 has two heavy chains (H-chain) 62 having a molecular weight of 50,000 to 70,000 and two light chains (L-chain) 63 having a molecular weight of 23,000. These four chain-form polypeptides are connected via a disulphide bond and a non-covalent bond to form the shape of the letter Y as a whole. The heavy chain (H-chain) 62 is constituted of 4 or 5 domains. A variable region ($V_H$) domain is positioned on the N-terminal side and 3 to 4 constant-region ($C_H1$, $C_H2$, $C_H3$, $C_H4$) domains are arranged toward the C-terminal. Note that, FIG. 6(a) shows a heavy chain 62 constituted of four domains ($V_H$, $C_H1$, $C_H2$, $C_H3$). The light chain (L-chain) 63 is constituted of two domains. A variable region ($V_L$) domain is positioned on the N-terminal side, and a constant region ($C_L$) domain is positioned on the C-terminal side.

The variable regions ($V_H$ and $V_L$) of the heavy chain 62 and the light chain 63 are positioned at two sites on the N-terminal side and integrated with each other to sterically form an antigen-binding site specifically binding to an antigen. Therefore, specificity of the antibody is determined by the amino acid sequences of the heavy-chain variable region and the light-chain variable region ($V_H$ and $V_L$) and a combination thereof. The amino acid sequences of the variable regions ($V_H$ and $V_L$) and the combination thereof vary depending upon the corresponding antigen. The constant regions ($C_H1$, $C_H2$, $C_H3$, $C_H4$ and $C_L$) of the heavy chain and the light chain have almost the same structure in every class or subclass.

The antibody molecule 61 is decomposed by a protease. i.e., papain at the hinge 64 present between $C_H1$ and $C_H2$ domains of the heavy chain to obtain two Fab fragments 65 and a single Fc fragment 66, as shown in FIG. 6(b). Note that, when the antibody molecule 61 is decomposed by another type of protease, i.e., pepsin, an F(ab')$_2$ fragment 67 can be obtained, which has two Fab fragments 65 connected via a disulphide bond at the hinge 64, as shown in FIG. 6(c). The Fab fragment 65 and the F(ab')$_2$ fragment 67 have an antigen-binding site constituted of the heavy-chain and light-chain variable regions ($V_H$ and $V_L$) and thus have a specificity to an antigen. They can be used in an antigen-antibody reaction.

Furthermore, a single-chain antibody (scFv) 68, which has a heavy-chain variable region ($V_H$) and light-chain variable region ($V_L$) connected via a linker peptide 69, can also form a sterical antigen-binding site constituted of the heavy-chain and light-chain variable regions ($V_H$ and $V_L$) and thus has a specificity to an antigen. The antibody (scFv) 68 can be used for an antigen-antibody reaction. FIG. 6(d) is a schematic view showing a basic structure of a single-chain antibody (scFv) 68. In FIG. 6(d), the C terminal of the heavy-chain variable region ($V_H$) is linked to the N terminal of the light-chain variable region ($V_L$) by a chain-form linker peptide 69.

In the antigen-antibody reaction, the specificity between an antigen and an antibody is high. If an antigen-binding site varies, the corresponding antigen differs. There are not less than a million combinations of a heavy-chain variable region and a light-chain variable region ($V_H$ and $V_L$). Which type of antigen-antibody reaction is exhibited by each of these combinations must be verified by a basic experiment. Furthermore, taking advantage of high antigen-antibody specificity, the antigen-antibody reaction has been used in various applications and fields.

As a method for detecting or measuring a minute amount of substance, immunoassay is conventionally known, which uses specific affinity between an antigen and an antibody. The immunoassay uses the diversity of antigen-antibody reaction to analyze various biogenic substances and is used in a wide variety of fields. Furthermore, to increase measurement sensitivity of immunoassay, various types of methods using a label such as a radioactive compound, a fluorescent substance, an enzyme are known. Corresponding to the labels, they are called e.g., radio immunoassay (RIA), immunofluorescent assay (fluoroimmunoassay: FIA) and enzymatic immunoassay (ELISA: Enzyme-Linked ImmunoSorbent Assay and also called enzyme immunoassay). Particularly, ELISA is a highly sensitive method excellent in quantitativity and a highly versatile detection method requiring no complicated steps such as purification and pretreatment and thus used in various analyses such as medical diagnosis, quantification of environmental hormones/residual agricultural chemical, bovine spongiform encephalopathy (BSE) examination and proteome analysis.

In these microanalyses based on immunoassay, a solid-phase method is employed, in which a protein such as an antigen, an antibody or an enzyme is immobilized to a solid phase such as a test tube or a microplate by means of physical adsorption and chemical binding. As the solid phase, usually, a hydrophobic plastic is used. Since a protein tightly binds to the hydrophobic solid phase by means of a hydrophobic interaction, the hydrophobic solid phase can be excellently used in a relatively large number of proteins. Presently, hydrophobic polystyrene (PS) is frequently used as a hydrophobic plastic.

Furthermore, any one of the immunoassays requires a plurality of times of an adsorption/reaction treatment and a washing treatment and thus takes a long time until a target substance is detected. Note that, also in an experiment for verifying an antigen-antibody reaction, the experiment is generally performed by immobilizing an antibody or the like to a solid phase such as a test tube and a microplate. In short, a solid-phase method is used.

For example, ELISA is roughly divided into a direct adsorption method, a sandwich method and a competitive method. In the case of the sandwich ELISA method according to Patent Document 1, first, an antibody against a target substance is allowed to bind to a solid phase and then the solid phase is washed a plurality of times. Second, a reagent (hereinafter referred to as a "blocking reagent"), which is not involved in an antigen-antibody reaction and an enzyme reaction, is allowed to bind to unbound sites remaining on the solid phase such that other reagents may not bind to the surface of the solid phase. After completion of blocking, the solid phase is washed a plurality of times. Third, a sample containing the target substance is allowed to react with the antibody bound onto the solid phase, and then, the solid phase is washed a plurality of times. Fourth, a second antibody is allowed to react with the target substance, and then, the solid phase is washed a plurality of times. Fifth, the second antibody is allowed to react with an enzyme label, and then, the solid phase is washed a plurality of times. Sixth, the enzyme label is allowed to react with a substrate and absorbance is measured to detect the target substance in the sample or the concentration thereof is measured (see Patent Document 1, paragraph 0039). Note that, if an antibody previously labeled with an enzyme is used as the second antibody to be reacted in the fourth treatment, the fifth treatment is no longer required.

Patent Document 1: National Publication of International Patent Application No. 2002-526777

DISCLOSURE OF THE INVENTION

Problems to be Solved by the Invention

As described above, there are not less than one million combinations of heavy-chain and light-chain variable regions ($V_H$ and $V_L$). Therefore, a great many number of experiments are required to verify an antigen-antibody reaction. However, since an antibody has a large molecular weight, animal cells are required to produce the antibody. A production cost is not cheap.

Furthermore, in the solid-phase methods for use in e.g., verification tests and immunoassay, usually, a hydrophobic plastic is used. However, since binding is made due to a hydrophobic interaction, which site of a protein such as an antigen, an antibody or an enzyme etc., binds to a solid phase cannot be specified. Depending upon the binding site to a solid phase, configuration change and inactivation occur. For example, an enzyme, i.e., O-acetylserine sulfhydrylase-A is almost completely inactivated when it binds to hydrophobic polystyrene. In addition, when a protein is connected to a solid phase randomly as mentioned above, not only measurement sensitivity but also measurement accuracy decreases.

The antibody molecule 61 has a shape of the letter Y as a whole, as shown in FIG. 6. At two N-terminal sides of the upper portion thereof, a sterical antigen-binding site is formed of the heavy-chain and the light-chain variable regions ($V_H$ and $V_L$). In immobilizing an antibody, if the C-terminal side binds vertically to a surface of a solid phase, the antigen-binding site faces outside and sterically normally positioned. As a result, an antigen-antibody reaction can be performed. However, if the N-terminal side binds to a solid phase, at least the antigen-binding site positioned on the N-terminal side cannot react with an antigen. In addition, at the time of binding to the solid phase, the tertiary structure of an antigen-binding site changes, causing denaturation of the antibody. In some of the cases, no antigen-antibody reaction is performed.

The fab fragment 65 and the F(ab')$_2$ fragment 67 are smaller in molecular weight than the antibody molecule 61. They can be produced directly in e.g., Escherichia coli and yeast. However, since the ratio occupied by antigen-binding sites is high, if the fragments are allowed to bind at random to a solid-phase surface, these is a high possibility of causing no antigen-antibody reaction. An extreme case is a single-chain antibody (scFv) 68, which is constituted of basically antigen-binding sites alone. The structure is favorable as an antibody substance for investigating an antigen-antibody reaction since the effect of an Fc region and a constant region can be eliminated; however the structure is extremely unfavorable for immobilization. When the single-chain antibody (scFv) 68 is immobilized as it is to a hydrophobic substrate, no substantial antigen-antibody reaction is shown.

Furthermore, when a protein is produced by a known cloning technology, a great deal of time and labor is required for a step of separating and purifying a desired protein product. For example, when Escherichia coli is used as a host, not only a desired protein but also various types of contaminants are present in Escherichia coli. Therefore, after Escherichia coli is cultured, Escherichia coli cells are crushed and a bacterial soluble fraction is centrifugally obtained and purified by a column. In this way, it is necessary to recover the desired protein.

Furthermore, when a large amount of xenogeneic gene is allowed to express in a host by introducing recombinant DNA therein, a protein is sometimes produced in the form of insoluble and inert aggregate, i.e., an inclusion body, to avoid a negative effect of the produced protein upon the host. The inclusion body is centrifugally recovered and then solubilized. However, the protein of the inclusion body is not active in this state and must be activated by returning the folding of the protein to a normal state. That is, a refolding operation is also required.

Furthermore, as described above, in immunoassay, an adsorption/reaction treatment and a washing treatment must be performed a plurality of times and a long time is required until a target substance is detected. It has been desired to develop a method for detecting or measuring a trace substance in a short time.

The present invention was made to solve one or some of the problems mentioned above, and provides a peptide containing a variable region that can be used in antigen-antibody reaction, a solid phase having each of these peptides immobilized thereto and a method for producing such a solid phase. Furthermore, there is provided a peptide containing a variable region and improved in production efficiency, a peptide containing a variable region, which is rarely changed in structure and rarely inactivated even if it is immobilized, a peptide containing a variable region, which can maintain the structure of a protein more than ever and maintain activity more than ever, for use in immonoassay, a peptide containing a variable region that can be used in immunoassay improved in measurement sensitivity with a stable measurement accuracy or a peptide containing a variable region, which can be used in a method for detecting or measuring a trace substance in a shorter time compared to a conventional method, and a solid phase having each of these peptides immobilized thereto and a method for producing such a solid phase.

Note that, in the specification, a novel and useful peptide and use of the peptide are disclosed. Furthermore, the present invention discloses a peptide expressing a function specifically binding to a hydrophilic solid phase and also use of the peptide. Furthermore, the present invention discloses a peptide that can be used for detecting or measuring a compound by use of the solid-phase method and use of the peptide.

Means for Solving the Problem

To attain the aforementioned objects, there is provided a peptide containing a variable region in which an antigen-binding site is to be formed and having an amino acid sequence expressing a specific adsorption function to a solid phase at a site closer to the C-terminal than a heavy-chain variable region or at a site closer to the C-terminal than a light-chain variable region. Furthermore, the peptide of the present invention is a peptide containing a variable region in which an antigen-binding site is to be formed and having any one of amino acid sequences represented by Sequence ID Nos. 1 to 20 of the sequence listing at a site closer to the C-terminal than a heavy-chain variable region or at a site closer to the C-terminal than a light-chain variable region. Moreover, the peptide of the present invention is preferably a single-chain antibody (scFv), a multivalent single-chain antibody (sc(Fv)$_n$), a single-chain antibody fused with a constant region (scFv-Fc), a Fab fragment or an F(ab')$_2$ fragment.

In the peptide of the present invention, it is preferable that the amino acid sequence expresses a specific adsorption function to a surface of a hydrophilic resin. The surface of the resin may be a hydrophilic polystyrene surface.

Furthermore, it is more preferable that the single-chain antibody (scFv), multivalent single-chain antibody (sc(Fv)$_n$), single-chain antibody fused with a constant region (scFv-Fc), Fab fragment or F(ab')$_2$ fragment has the amino acid sequence both in the heavy chain and in the light chain. The peptide of the present invention has a linker peptide that connects the heavy-chain variable region and the light-chain variable region and may have the amino acid sequence between the linker peptide and the variable region or within the linker peptide.

Furthermore, in a method for producing a purified peptide of the present invention, a solution containing a peptide having an amino acid sequence expressing a specific adsorption function to a solid phase and contaminants is brought into contact with a surface of the solid phase to allow the peptide into direct contact with the surface of the solid phase to purify the peptide.

Furthermore, in a method for producing a reconstructed peptide of the present invention, a solution containing a denatured peptide having an amino acid sequence expressing a specific adsorption function to a solid phase and a denaturizing agent is brought into contact with a surface of the solid phase to allow the peptide to directly adsorb to the surface of the solid phase to reconstruct the denatured peptide. The denatured peptide herein may be an inclusion body.

In the method for producing a peptide, the peptide contains a variable region in which an antigen-binding site is to be formed and may have the aforementioned amino acid sequence at a site closer to the C-terminal than a heavy-chain variable region or at a site closer to the C-terminal than a light-chain variable region. Furthermore, the solution may contain a crushed material, a medium or a secretion of a host which produced the peptide. Furthermore, as the amino acid sequence, any one of the amino acid sequences represented by Sequence ID Nos. 1 to 20 of the sequence listing can be used.

Furthermore, in the present invention, a solid phase having a peptide immobilized thereto may be produced by introducing a gene containing a base sequence, which encodes a peptide having an amino acid sequence expressing a specific adsorption function to a solid phase, into a host to obtain a transformant, bringing a solution containing a product of the transformant into contact with a surface of the solid phase to allow the peptide in directly adsorb to the surface of the solid phase. The peptide herein contains a variable region in which an antigen-binding site is to be formed at a site closer to the C-terminal than a heavy-chain variable region or at a site closer to the C-terminal than a light-chain variable region.

The solution containing the product may contain a crushed material of the host, a medium for the host, or a secretion produced by secretion from yeast.

Furthermore, the present invention is directed to a peptide containing a variable region in which an antigen-binding site is to be formed or may be directed to a gene containing a base sequence, which encodes a peptide having an amino acid sequence expressing a specific adsorption function to a solid phase, at a site closer to the C-terminal than a heavy-chain variable region or at a site closer to the C-terminal than a light-chain variable region, a vector prepared of the gene or a host having the gene introduced therein.

Furthermore, the peptide of the present invention is preferably a peptide containing the amino acid sequence represented by Sequence ID No. 1 of the sequence listing. Furthermore, the peptide of the present invention is a peptide, which is to be immobilized to a solid phase used in immunoassay and which may contain the amino acid sequence represented by Sequence ID No. 1 of the sequence listing. The amino acid sequence represented by Sequence ID No. 1 of the sequence listing may be any one of the amino acid sequences represented by Sequence ID Nos. 2 to 10.

The solid phase may have a hydrophilic resin surface and the solid phase may have a hydrophilic polystyrene surface. The immunoassay may be an enzymatic immunoassay.

Furthermore, the present invention also discloses an immobilized enzyme containing the amino acid sequence represented by Sequence ID No. 1 of the sequence listing, a gene having a base sequence encoding the amino acid sequence represented by Sequence ID No. 1 of the sequence listing, and a vector prepared of the gene or a host having the gene introduced therein. Furthermore, the amino acid sequence represented by Sequence ID No. 1 of the sequence listing may be any one of the amino acid sequences represented by Sequence ID Nos. 2 to 10 of the sequence listing.

Advantages of the Invention

Since the peptide of the present invention exhibits an excellent binding ability to a predetermined solid-phase surface and can be immobilized directly to a predetermined solid phase, the peptide of the present invention can be easily separated and purified. More specifically, after the peptide of the present invention is produced, even though sufficient purification is not performed, the peptide of the present invention can be allowed to bind directly to a solid phase simply by bringing a solution containing the peptide of the present invention into contact with a predetermined solid phase. Separation/purification of the peptide of the invention from the solution and immobilization to the solid phase can be simultaneously performed. As a result, a separation/purification step (for example, purification step using an affinity column), which conventionally takes a long time, can be omitted and the time required from production of the peptide of the present invention to immobilization to a solid phase can be drastically reduced. Therefore, the efficiency in producing the peptide of the present invention is dramatically improved. In addition, in this step, a protein produced in the form of an inclusion body and denatured protein can be refolded.

Furthermore, the peptide of the present invention can be used in detecting or measuring a compound using a solid-phase method. Particularly, in immunoassay, compared to conventional methods, measurement time can be reduced by a specific adsorption function and immobilization can be performed while maintaining the activity of an original peptide. Thus, measurement sensitivity can be improved to obtain a stable measurement accuracy.

BEST MODE FOR CARRYING OUT OF THE INVENTION

Figure 1:
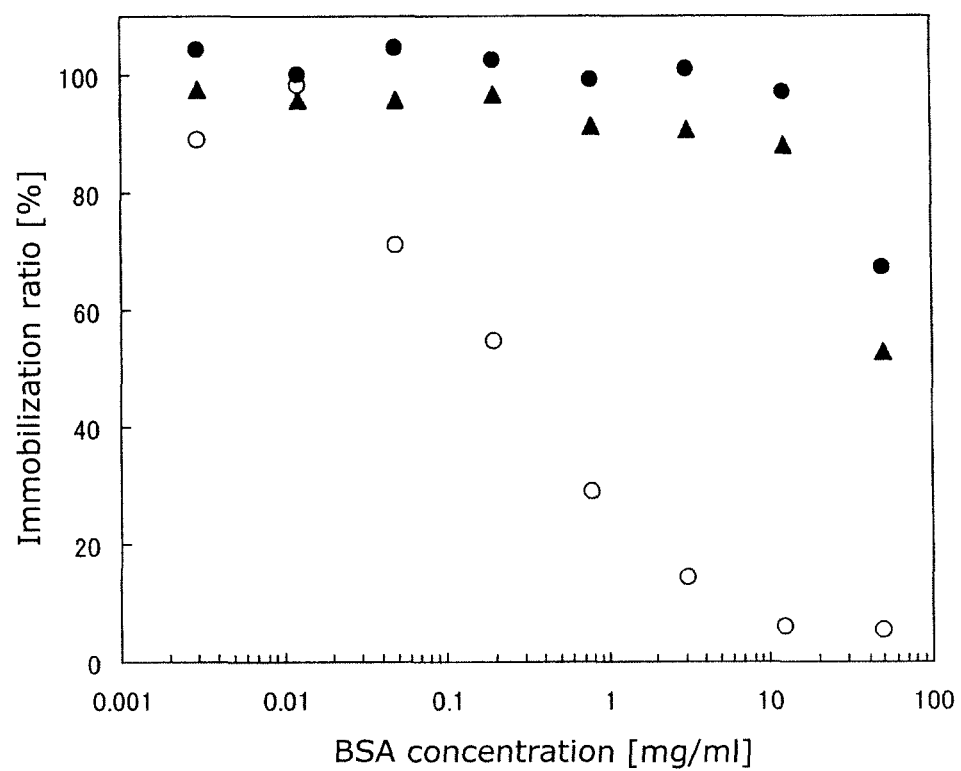
FIG. 1 is a graph showing the immobilization ratio to a hydrophilic polystyrene surface in the presence of BSA.
Figure 2:
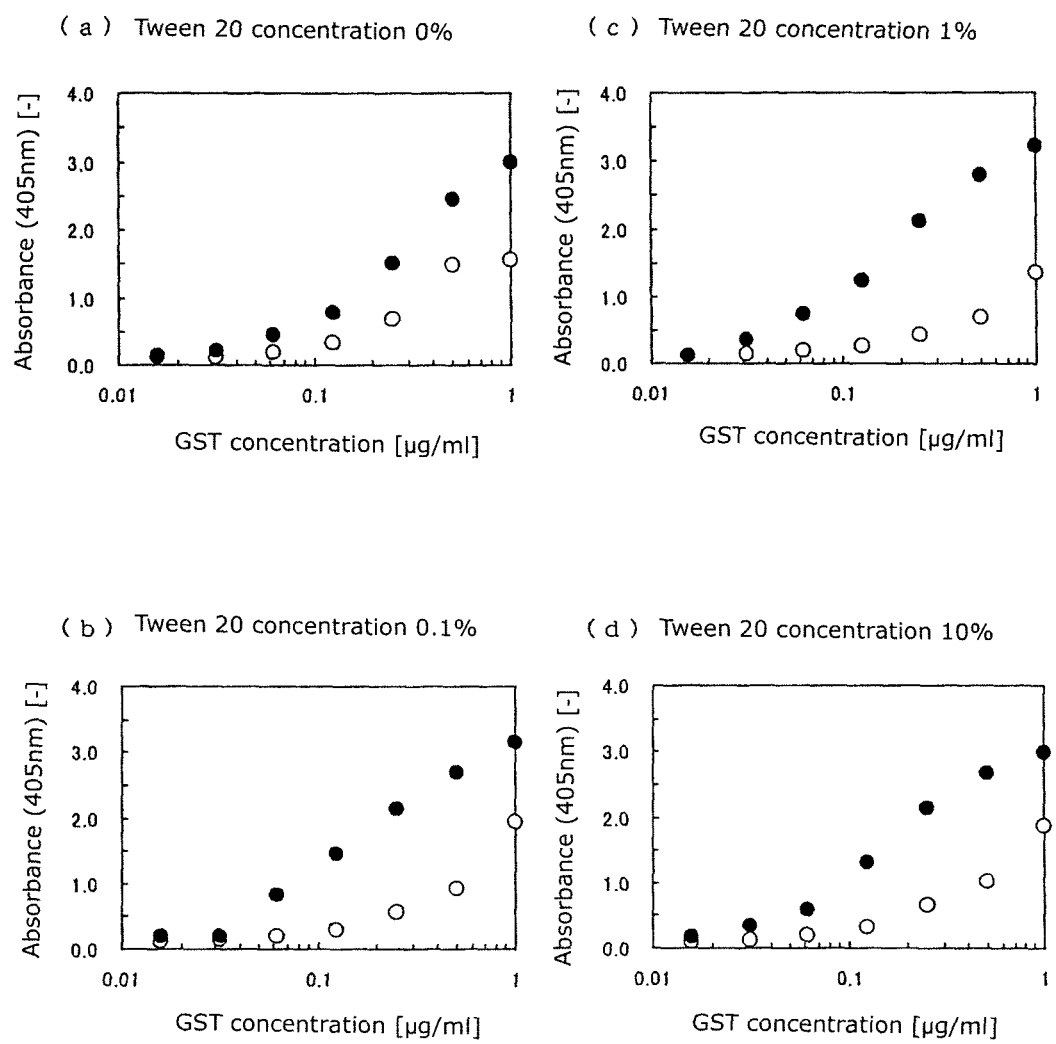
FIG. 2(a) to (d) are graphs showing the binding ability to a hydrophilic polystyrene plate in the conditions of a Tween 20 addition amount of 0, 0.1, 1 and 10%, respectively.
Figure 3:
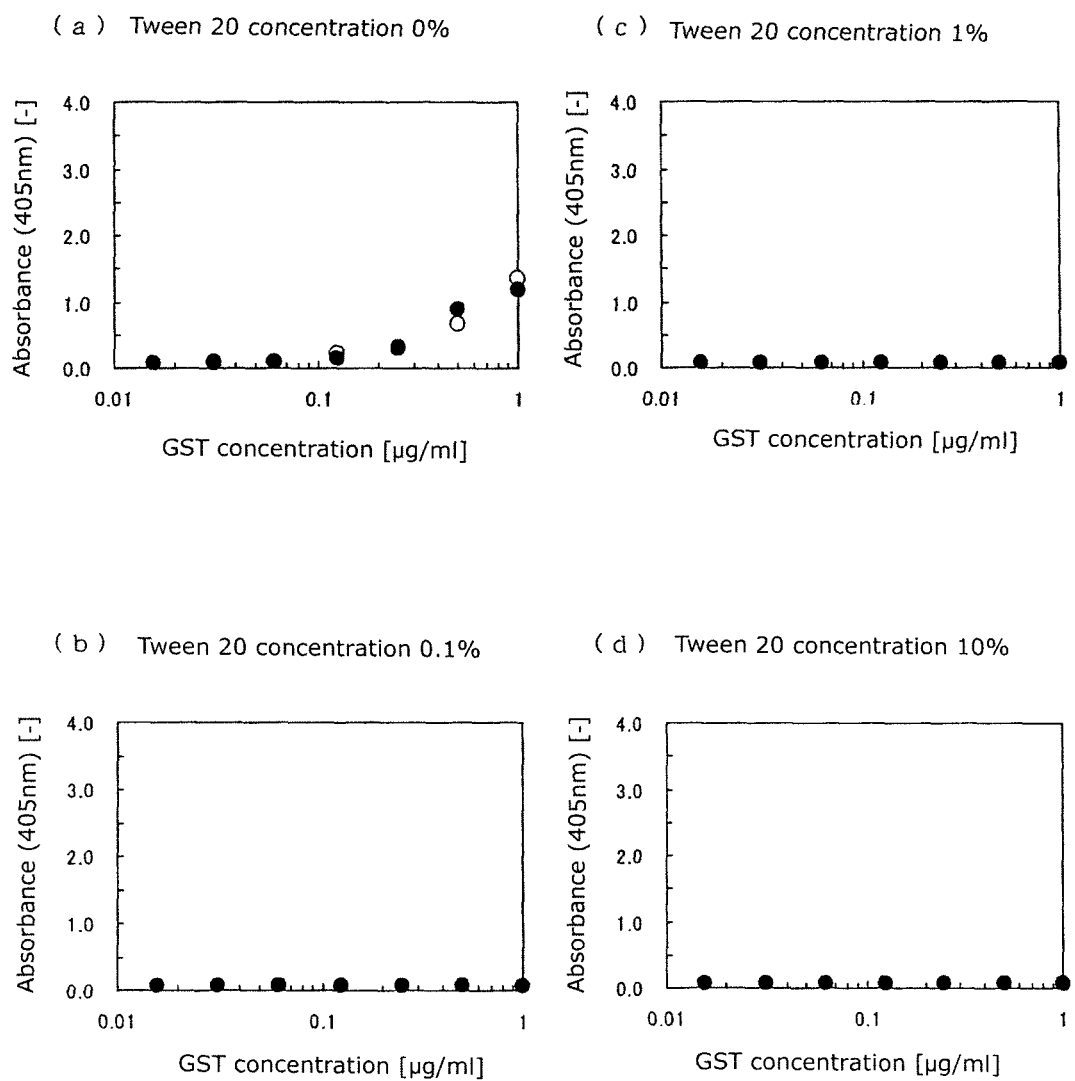
FIG. 3(a) to (d) are graphs showing the binding ability to a hydrophobic polystyrene plate in the conditions of a Tween 20 addition amount of 0, 0.1, 1 and 10%, respectively.

The present invention will be specifically described below. The peptide of the present invention has an amino acid sequence (hereinafter referred to as "the amino acid sequence of the invention") expressing a specific adsorption function to a solid phase. The amino acid sequence of the invention is, for example, any one of the amino acid sequences represented by Sequence ID Nos. 1 to 20 of the sequence listing (hereinafter, referred to as "amino acid sequence 1 of the invention" to "amino acid sequence 20 of the invention"). The peptide having the amino acid sequence of the invention will be referred to as "the peptide of the invention".

The amino acid sequence of the invention expresses a specific adsorption function to a predetermined solid phase (for example, a solid phase having a hydrophilic resin surface). Therefore, the peptide of the invention exhibits an excellent binding ability to a predetermined solid-phase surface and can be immobilized directly to the specific solid-phase. By virtue of this, the peptide of the invention can be easily separated and purified. More specifically, after the peptide of the invention is produced, even if sufficient purification is not performed, the peptide of the invention can be allowed to bind directly to a solid phase simply by bringing a solution containing the peptide of the invention to a predetermined solid phase. That is, a separation/purification step of the peptide of the invention from the solution to an immobilization step of the peptide to a solid phase can be simultaneously performed. As a result, a separation/purification step (for example, purification step using an affinity column) requiring a long time in a conventional method can be omitted, with the result that the time required from production of the peptide of the invention to immobilization to a solid phase can be drastically reduced. The efficiency in producing the peptide of the invention is thus dramatically improved. In addition, in this step, refolding of a protein produced in the form of an inclusion body and denatured protein can be also made.

Furthermore, the peptide of the invention can be used in detecting or measuring a compound by use of a solid-phase method. An antigen, an antibody or an enzyme to be subjected to detection or measurement of a compound, can be directly immobilized to a predetermined solid phase by introducing the amino acid sequence of the invention into the antigen, antibody or enzyme, thereby enabling detection or measurement of the compound. Particularly, the peptide of the invention is preferably applied to detection or measurement of a trace substance using immunoassay. Furthermore, the peptide of the invention can directly and specifically bind onto a predetermined solid phase preferentially by the introduction site of the amino acid sequence of the invention even in the presence of contaminants and thereby can be immobilized onto a predetermined solid phase with the orientation and structure controlled. Therefore, immobilization can be made while maintaining activity of an original peptide compared to conventional immobilization. Therefore, measurement sensitivity can be improved to obtain stable measurement accuracy.

For example, in the case of applying to a sandwich ELISA method, a peptide having the amino acid sequence of the invention is introduced into an antibody causing an antigen-antibody reaction specifically to a target substance to prepare the peptide of the invention, i.e., an antibody. First, such an antibody is allowed to directly bind to a predetermined solid phase, which is then washed a plurality of times. Second, unbound sites remaining on the solid phase are blocked by a blocking reagent, and then, the solid phase is washed a plurality of times. Third, a sample containing the target substance is allowed to react with the peptide of the invention, i.e., the antibody, bound to the solid phase, and then, the solid phase is washed a plurality of times. Fourth, a second antibody, which is not the peptide of the invention, is allowed to react with the target substance, and then, the solid phase is washed a plurality of times. Fifth, the second antibody is allowed to react with an enzyme label, and then, the solid phase is washed a plurality of times. Sixth, the enzyme label is allowed to react with a substrate and absorbance is measured to detect the target substance in the sample or the concentration thereof is measured.

As mentioned above, the detection or measurement of a compound can be made by immunoassay using the peptide of the invention. Note that, if an antibody already tagged with an enzyme label is used as the second antibody to be reacted in the fourth treatment, the fifth step is no longer required. Furthermore, since a specific binding is made by the peptide of the invention even in the presence of a blocking reagent, if the peptide of the invention, i.e., an antibody, and a blocking reagent are simultaneously allowed to bind to a predetermined solid phase in the first treatment, the second treatment can be omitted. As a result, the time for detection or measurement of a compound can be reduced.

Furthermore, the peptide of the invention, i.e., an antibody, and a target substance are first subjected to an antigen-antibody reaction in a solution to form an immune complex, and then, the immune complex is immobilized onto a predetermined solid phase. In this way, a new method for detecting or measuring a compound capable of dramatically reducing the time for detecting or measuring a compound can be realized. More specifically, the first treatment and the third treatment of the sandwich method can be carried out in a single treatment. If a blocking reagent is also added to the solution, the first, second and third treatments can be carried out in a single treatment. More preferably, after the immune complex of the peptide of the invention, i.e., an antibody, with a target substance is formed, and an antigen-antibody reaction between the immune complex and the second antibody enzymatically labeled is also performed in the solution to form a larger immune complex, which is immobilized onto a predetermined solid phase. In this way, the first to fifth treatments can be carried out in a single treatment.

The peptide of the invention can be specifically and directly immobilized onto a predetermined solid phase with the orientation and structure controlled even in the presence of a contaminant. Therefore, even if a blocking reagent is present and even in the state of an immune complex, the immune complex can be immobilized to perform detection or measurement of a target substance. In addition, since the antigen-antibody reaction is extremely rapidly performed in a solution without sterical hindrance, the rate of the reaction can be drastically increased compared to a conventional antigen-antibody reaction performed in an immobilized state. Consequently, measurement sensitivity can be improved to obtain stable measurement accuracy.

Furthermore, the peptide of the invention finds another use. If an enzyme is employed as the peptide of the invention, it can be used as an immobilized enzyme fixed on a hydrophilic resin surface. Since an enzyme is generally soluble in water, it is discarded every time it is used. However, if an enzyme is immobilized by binding it to a solid phase, it can be separated from a water-soluble reaction product and can be continuously and repeatedly used in a reaction.

Amino acid sequence 1 of the invention (SEQ ID NO:1) is the sequence of RXXXRRXRR (R: arginine, X: isoleucine (I), leucine (L), valine (V), alanine (A), glycine (G), methionine (M), serine (S) or threonine (T), which is used singly or in combination of a plurality of elements) in the order from the N-terminal side toward the C-terminal side, as represented by Sequence ID No. 1 of the sequence listing. Therefore, amino acid sequence 1 of the invention includes at least amino acid sequences 2 to 10 of the invention.

Amino acid sequence 2 of the invention (SEQ ID NO:2) is the sequence obtained by replacing all Xs of amino acid sequence 1 of the invention by isoleucine (I), that is, the sequence of RIIIRRIRR (R: arginine, I: isoleucine) in the order from the N-terminal side toward the C-terminal side. Amino acid sequence 3 of the invention (SEQ ID NO:3) is the sequence obtained by replacing Xs of amino acid sequence 1 of the invention by a combination of alanine (A) and isoleucine (I), that is, the sequence of RAIARRIRR (R: arginine, A: alanine, I: isoleucine) in the order from the N-terminal side toward the C-terminal side. Amino acid sequence 4 of the invention (SEQ ID NO:4) is the sequence obtained by replacing all Xs of amino acid sequence 1 of the invention by leucine (L), that is, the sequence of RLLLRRLRR (R: arginine, L: leucine) in the order from the N-terminal side toward the C-terminal side. Amino acid sequence 5 of the invention (SEQ ID NO:5) is the sequence obtained by replacing all Xs of amino acid sequence 1 of the invention by valine (V), that is, the sequence of RVVVRRVRR (R: arginine, V: valine) in the order from the N-terminal side toward the C-terminal side. Amino acid sequence 6 of the invention (SEQ ID NO:6) is the sequence obtained by replacing all Xs of amino acid sequence 1 of the invention by alanine (A), that is, the sequence of RAAARRARR (R: arginine, A: alanine) in the order from the N-terminal side toward the C-terminal side. Amino acid sequence 7 of the invention (SEQ ID NO:7) is the sequence obtained by replacing all Xs of amino acid sequence 1 of the invention by glycine (G), that is, a sequence of RGGGRRGRR (R: arginine, G: glycine) in the order from the N-terminal side toward the C-terminal side.

As described later in Examples 1 to 6, it was confirmed that any one of the peptides having amino acid sequences 2 to 7 of the invention expresses a specific adsorption function to a predetermined solid-phase surface. In amino acid sequences 2 to 7 of the invention, arginine (R) is commonly located at the 1, 5, 6, 8, 9th positions from the N-terminal side and different amino acids (Xs of amino acid sequence 1 of the invention) are arranged between them. As amino acid sequences 2, 4 to 7 of the invention, amino acids of a same type are arranged, whereas alanine (A) and isoleucine (I) are arranged in combination in the case of amino acid sequence 3 of the invention. Since all of them exhibit the same properties in common, it is presumed that the specific adsorption function to a predetermined solid-phase surface may be expressed by employing, as X of amino acid sequence 1 of the invention, isoleucine (I), leucine (L), valine (V), alanine (A) and glycine (G), singly or in combination.

Furthermore, amino acid sequence 8 of the invention (SEQ ID NO:8) is the sequence obtained by replacing all Xs of amino acid sequence 1 of the invention by methionine (M), that is, the sequence of RMMMRRMRR (R: arginine, M: methionine) in the order from the N-terminal side toward the C-terminal side. Amino acid sequence 9 of the invention (SEQ ID NO:9) is the sequence obtained by replacing all Xs of amino acid sequence 1 of the invention by serine (S), that is, the sequence of RSSSRRSRR (R: arginine, S: serine) in the order from the N-terminal side toward the C-terminal side. Amino acid sequence 10 of the invention (SEQ ID NO:10) is the sequence obtained by replacing all Xs of amino acid sequence 1 of the invention by threonine (T), that is, the sequence of RTTTRRTRR (R: arginine, T: threonine) in the order from the N-terminal side toward the C-terminal side.

As described later in Examples 7 to 9, it was confirmed that any one of the peptides having amino acid sequences 8 to 10 of the invention expresses a specific adsorption function to a predetermined solid-phase surface. Although methionine (M), serine (S) or threonine (T) contains sulfur and a hydroxy group (OH) in the R group of the amino acid (R—CH(NH2) COOH), it partially has a chain-form saturated hydrocarbon and a neutral amino acid. In this respect, they are common with isoleucine (I), leucine (L), valine (V) and alanine (A), which have an R group constituted of a chain-form saturated hydrocarbon. Furthermore, methionine (M), serine (S) and threonine (T) are also common with them in that R group has neither a cyclic structure nor an aromatic compound and they are amino acids a less-bulky tertiary structure. For this reason, even if methionine (M), serine (S) or threonine (T) is selected as X of amino acid sequence 1 of the invention, the same effect is presumably obtained.

Furthermore, amino acid sequence 11 of the invention (SEQ ID NO:11) is the sequence of KGLRGWREMISL (lysine (K), glycine (G), leucine (L), arginine (R), glycine (G), tryptophan (W), arginine (R), glutamine acid (E), methionine (M), isoleucine (I), serine (S), leucine (L)) in the order from the N-terminal side toward the C-terminal side, as represented by Sequence ID No. 11 of the sequence listing.

Amino acid sequence 12 of the invention (SEQ ID NO:12) is the sequence of ADYLSRWGSIRN (alanine (A), aspartic acid (D), tyrosine (Y), leucine (L), serine (S), arginine (R), tryptophan (W), glycine (G), serine (S), isoleucine (I), arginine (R), asparagine (N)) in the order from the N-terminal side toward the C-terminal side, as represented by Sequence ID No. 12 of the sequence listing.

Amino acid sequence 13 of the invention (SEQ ID NO:13) is the sequence of SRVHRAVLNGVS (serine (S), arginine (R), valine (V), histidine (H), arginine (R), alanine (A), valine (V), leucine (L), asparagine (N), glycine (G), valine (V), serine (S)) in the order from the N-terminal side toward the C-terminal side, as represented by Sequence ID No. 13 of the sequence listing.

Amino acid sequence 14 of the invention (SEQ ID NO:14) is the sequence of RPPGVVRRYALG (arginine (R), proline (P), proline (P), glycine (G), valine (V), valine (V), arginine (R), arginine (R), tyrosine (Y), alanine (A), leucine (L), glycine (G)) in the order from the N-terminal side toward the C-terminal side, as represented by Sequence ID No. 14 of the sequence listing.

Amino acid sequence 15 of the invention (SEQ ID NO:15) is the sequence of VRSWEEQARVTT (valine (V), arginine (R), serine (S), tryptophan (W), glutamine acid (E), glutamine acid (E), glutamine (Q), alanine (A), arginine (R), valine (V), threonine (T), threonine (T)) in the order from the N-terminal side toward the C-terminal side, as represented by Sequence ID No. 15 of the sequence listing.

Amino acid sequence 16 of the invention (SEQ ID NO:16) is the sequence of RAFIASRRIKRP (arginine (R), alanine (A), phenylalanine (F), isoleucine (I), alanine (A), serine (S), arginine (R), arginine (R), isoleucine (I), lysine (K), arginine (R), proline (P)) in the order from the N-terminal side toward the C-terminal side, as represented by Sequence ID No. 16 of the sequence listing.

Amino acid sequence 17 of the invention (SEQ ID NO:17) is the sequence of RESTLKGTSRAV (arginine (R), glutamine acid (E), serine (S), threonine (T), leucine (L), lysine (K), glycine (G), threonine (T), serine (S), arginine (R), alanine (A), valine (V)) in the order from the N-terminal side toward the C-terminal side, as represented by Sequence ID No. 17 of the sequence listing.

Amino acid sequence 18 of the invention (SEQ ID NO:18) is the sequence of AGLRLKKAAIHR (alanine (A), glycine (G), leucine (L), arginine (R), leucine (L), lysine (K), lysine (K), alanine (A), alanine (A), isoleucine (I), histidine (H), arginine (R)) in the order from the N-terminal side toward the C-terminal side, as represented by Sequence ID No. 18 of the sequence listing.

Amino acid sequence 19 of the invention (SEQ ID NO:19) is the sequence of SSLLRAVPEPTG (serine (S), serine (S), leucine (L), leucine (L), arginine (R), alanine (A), valine (V), proline (P), glutamine acid (E), proline (P), threonine (T), glycine (G)) in the order from the N-terminal side toward the C-terminal side, as represented by Sequence ID No. 19 of the sequence listing.

Amino acid sequence 20 of the invention (SEQ ID NO:20) is the sequence of RAFIASRRIRRP (arginine (R), alanine (A), phenylalanine (F), isoleucine (I), alanine (A), serine (S), arginine (R), arginine (R), isoleucine (I), arginine (R), arginine (R), proline (P)) in the order from the N-terminal side toward the C-terminal side, as represented by Sequence ID No. 20 of the sequence listing.

Amino acid sequences 1 to 20 of the invention can express a specific adsorption function to a predetermined solid phase. The predetermined solid phase refers to a solid phase having a hydrophilic resin surface as long as it has been so far confirmed. More specifically, the peptide of the invention is improved in binding ability to a hydrophilic resin surface compared to the original peptide. Particularly, the peptide of the invention exhibits an excellent binding ability to a hydrophilic polystyrene surface. The binding ability refers to an ability to preferentially bind to something in competitive with contaminants, and can be evaluated by comparing the amount of peptide of the invention binding to a solid phase in the presence of competitive contaminants such as other peptides, polymer compounds and surfactants.

Examples of the solid phase having a hydrophilic resin surface include a solid phase having a surface of a plastic resin, such as polystyrene, polycarbonate, polypropylene, polyethylene, polydimethylsiloxane (PDMS) and poly(methyl methacrylate) (PMMA) and modified to be hydrophilic by a treatment. The surface of a plastic resin produced is usually hydrophobic. However, the surface is modified with any one of hydrophilic treatments to obtain a solid phase having a hydrophilic resin surface. For example, when a $UV+O_3$ treatment or a plasma oxidation treatment is applied to a polystyrene surface, a solid phase having a hydrophilic polystyrene surface can be prepared.

The form of a solid phase may be a plate-form (including a wall surface and bottom surface of a container and a well) or a granule-form. As described in Japanese Patent Application Laid-Open No. 2007-279018, if fluid manipulation portions (wells) of a microwell plate are filled with granular plastic substrates whose surface are hydrophilically treated, the peptide of the invention can be immobilized to the surface of the granular plastic substrates simply by pouring a solution containing the peptide of the invention into the wells.

In the specification, the "peptide" refers to a substance consisting of not less than two amino acids bound via a peptide bond and includes an oligopeptide, a polypeptide, a protein, a homomeric peptide and a heteromeric peptide. Furthermore, the peptide of the invention is sometimes present in the state of an electrically neutral state or in the form of a salt, may be present in the form only consisting of the amino acid sequence of the invention shown in the sequence listing, in the form of a fusion protein consisting of a specific protein having the peptide of the invention fused at an end or the inside thereof, in the form of a complex obtained by adding a sugar, polyethylene glycol, an NCS group (isothiocyanate), an NHS group (N-Hydroxy succinimide ester), a maleimide group, a thiol group, biotin, a fluorescent dye, etc., and further in the form of a derivative or a polymer obtained by acetylation, amidation of a peptide and/or crosslinked polymerization by a polyfunctional test.

The base sequence represented by Sequence ID No. 21 of the sequence listing is an example of the base sequence encoding amino acid sequence 2 of the invention, more specifically, DNA containing the base sequence of cgt atc atc atc cga agg att cga cga (SEQ ID NO:21) (a: adenine, g: guanine, c: cytosine, t: thymine) in the order from the 5' end side toward the 3' end side. The base sequence represented by Sequence ID No. 22 of the sequence listing is an example of the base sequence encoding amino acid sequence 3 of the invention, more specifically, DNA containing the base sequence of cgt gcg att gcg cga agg att cga cga (SEQ ID NO:22) (a: adenine, g: guanine, c: cytosine, t: thymine) in the order from the 5' end side toward the 3' end side. The base sequence encoding amino acid sequence 2 or 3 of the invention is not limited to that represented by Sequence ID No. 21 or 22. Other than this, the sequence of codon corresponding to each amino acid represented by amino acid sequence 2 or 3 of the invention can be employed. The gene containing the base sequence encoding the amino acid sequence of the invention is expressed in the host by use of a vector such as a phage or a plasmid or by introducing it into the genomic DNA of the host to biologically synthesize the peptide of the invention.

As the peptide of the invention, various proteins can be used and can be applied to many antigens, antibodies, lectins, enzymes, receptor proteins, or the like. For example, the peptide of the invention can be applied to glutathione transferase (GST: Glutathione S-Transferase), maltose-binding protein (MBP), alkaline phosphatase (ALP), peroxidase (POD), luciferase, green fluorescent protein (GFP), β-galactosidase (β-Gal), trypsin, chymotrypsin, thrombin, Factor Xa, angiotensin converting enzyme, tyrosine kinase, insulin receptor, EGF receptor, streptavidin (SA), a monoclonal antibody (Mab), a polyclonal antibody (Pab), a single-chain antibody (scFv), a multivalent single-chain antibody (sc(Fv)$_n$) (for example, a divalent single-chain antibody (sc(Fv)$_2$)), a single-chain antibody fused with a constant region (scFv-Fc), a Fab fragment and an F(ab')$_2$ fragment (an antibody fragment containing an antigen-binding site), complement-system protein C1q, concanavalin A (ConA), lentil lectin (LCA) and an antibody-binding protein (e.g., Protein A, ZZ, Protein G, Protein L), etc. Note that, in the specification, to distinguish the peptide of the invention, a peptide obtained by removing the amino acid sequence of the invention from the peptide of the invention (including a peptide to which the amino acid sequence of the invention is to be introduced afterward) will be hereinafter referred to as "the original peptide".

Note that, when a peptide containing a variable region in which an antigen-binding site is to be formed is used as the peptide of the invention, the antibody molecule itself is included; however, a single-chain antibody (scFv), a multivalent single-chain antibody (sc(Fv)$_n$), a single-chain antibody fused with a constant region (scFv-Fc), a Fab fragment and an F(ab')$_2$ fragment, which are capable of being produced in *Escherichia coli* and yeast, are preferably used. A multivalent single-chain antibody (sc(Fv)$_n$), which consists of a plurality of single-chain antibodies (scFv) each connected via a linker peptide, is a generic term of a peptide having a plurality of antigen-binding sites (heavy-chain variable region ($V_H$) and light-chain variable region ($V_L$) domains) within a molecule. The antigen-binding sites may be the same or different. Note that, the divalent single-chain antibody (sc(Fv)$_2$) refers to an antibody consisting of two single-chain antibodies (scFv) connected via a linker peptide. The single-chain antibody fused with a constant region (scFv-Fc) is a generic term of a fusion protein having a Fc domain on the C-terminal side of the single-chain antibody (scFv). The Fab fragment refers to one of the fragments obtained by papain digestion of an antibody molecule and having a light chain consisting of $V_L$ and $C_L$ and a heavy chain consisting of $V_H$ and $C_H1$ domains associated with each other; however it can be prepared by genetic recombination technology. The F(ab')$_2$ fragment refers to one of the fragments obtained by pepsin digestion of an antibody molecule and having two Fab molecules connected by a disulphide bond at the hinge portion; however, it can be prepared by genetic recombination technology.

In the peptide of the invention, the site to which the amino acid sequence of the invention is to be introduced is the site which does not prevent the physiological activity that the original peptide intrinsically has. For example, in an antigen, a site except for an antigenic determinant is used. In an antibody, a site except for an antibody activating group is used. Particularly, immobilization is made on a solid phase while maintaining the tertiary structure of the original peptide. It is therefore preferable to introduce the amino acid sequence of the invention into a site in the vicinity of the C terminal or the N terminal of the original peptide. Note that, to the peptide of the invention, other than the amino acid sequence of the invention, an affinity tag for labeling and the like may be separately introduced.

Particularly, when a peptide containing a variable region in which an antigen-binding site is to be formed is employed as the peptide of the invention, the amino acid sequence of the invention is introduced into a site closer to the C-terminal than a heavy-chain variable region or a site closer to the C-terminal than a light-chain variable region (including both of them). The site closer to the C-terminal than a variable region refers to a site from the C terminal of a heavy-chain or a light-chain variable region to the C terminal of the entire peptide of the invention, that is, refers to all sites which do not inhibit antigen binding of the variable region.

Figure 6:
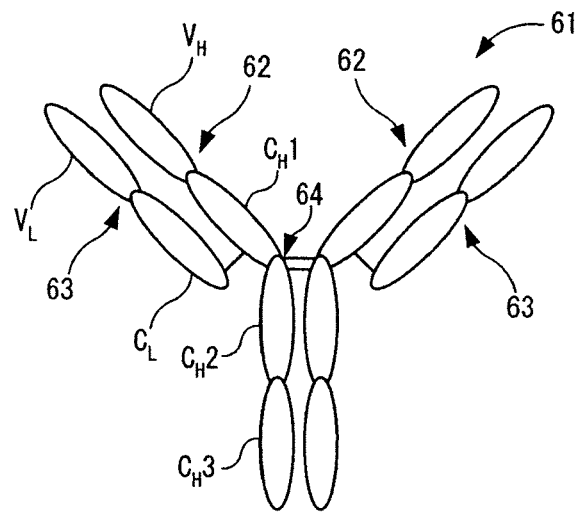
FIG. 6(a) is a schematic view showing the basic structure of an antibody; (b) is a schematic view showing the structures of a Fab fragment and an Fc fragment; (c) is a schematic view showing the structure of an F(ab')$_2$ fragment; and (d) is a schematic view showing the basic structure of a single-chain antibody (scFv).
Figure 6:
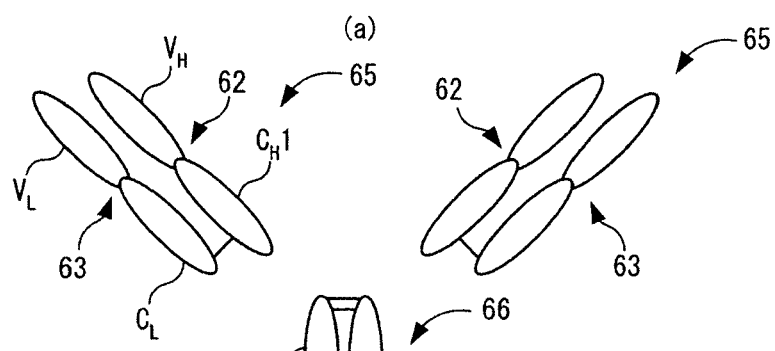
Figure 6:
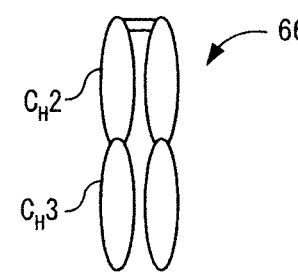
Figure 6:
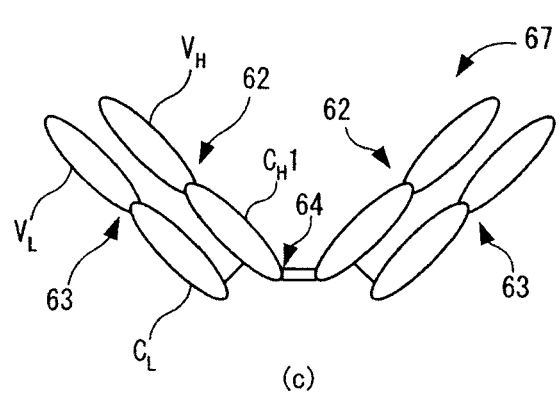
Figure 6:
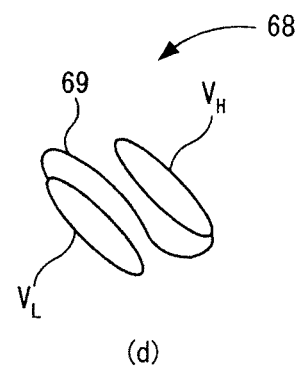

In the case of an antibody molecule (see FIG. 6(*a*)), the amino acid sequence of the invention is preferably introduced into a single site or a plurality of sites of the N terminal and the C terminal of the constant region ($C_H1$, $C_H2$, $C_H3$, $C_H4$) domains, which are positioned closer to the C terminal than the variable region ($V_H$) of the heavy chain (H-chain) 62, and the N terminal and the C terminal of the constant region ($C_L$) domain of the light chain (L-chain) 63. The amino acid sequence of the invention is particularly preferably introduced into a single site or a plurality of sites of the N terminal and the C terminal of the constant region ($C_H2$, $C_H3$, $C_H4$) domains in the Fc region of the heavy chain 62, and the C terminal of the light chain 63.

In the case of a Fab fragment or an F(ab')$_2$ fragment (see FIGS. 6(*b*) and (*c*)), the amino acid sequence of the invention is preferably introduced into a single site or a plurality of sites of the C terminal of the variable-region domains ($V_H$ and $V_L$) of the heavy chain 62 or the light chain 63 and the N terminal and the C terminal of the constant region ($C_H1$ and $C_L$) domains. The amino acid sequence of the invention is particularly preferably introduced into a single site or a plurality of sites of the C terminal of the heavy chain 62 or the C terminal of the light chain 63.

Furthermore, in the case of an antibody having a linker peptide connecting a heavy chain and a light chain, such as a single-chain antibody (scFv), a multivalent single-chain antibody (sc(Fv)$_n$) and a single-chain antibody fused with a constant region (scFv-Fc), the amino acid sequence of the invention may be introduced into the site between the linker peptide and the heavy chain or the light chain or within the linker peptide. The linker peptide herein connects the C terminal of one of the heavy chain and the light chain and the N terminal of the other chain. The C-terminal side of the heavy chain or the light chain includes the entire linker peptide, in other words, from the site of the linker peptide connecting to the C terminal of the heavy chain or the light chain to the N terminal of the other chain. Note that, the site between the linker peptide and the heavy chain or the light chain, or within the linker peptide, something other than the amino acid sequence of the invention, e.g., an affinity tag for labeling, may be separately introduced. In the case of the single-chain antibody (scFv) (FIG. 6(d)), the amino acid sequence of the invention is introduced into one or both of the C-terminal side of the light-chain variable region ($V_L$) and the site from the C terminal of the heavy-chain variable region ($V_H$) to the N terminal of the light-chain variable region ($V_L$) including the interior of the linker peptide 69.

The tertiary structure of the peptide of the invention can be maintained more normally by introducing the amino acid sequence of the invention into a plurality of sites. For example, if the amino acid sequences of the invention is introduced separately into the C-terminal sides of the heavy chain and the light chain of a Fab fragment or an $F(ab')_2$ fragment, or if the amino acid sequences of the invention is introduced separately into the C-terminal sides of the heavy chain and the light chain of a single-chain antibody (scFv), the introduction sites easily bind to a solid-phase surface. As a result, the antigen-binding site faces outside and an antigen-antibody reaction easily occurs.

The peptide of the invention can be produced by a known cloning technology and chemical synthesis. For example, DNA encoding the amino acid sequence of the invention is prepared by use of a cloning technology, and inserted into an autonomously replicable vector to prepare a recombinant DNA. The recombinant DNA is introduced into an appropriate host, such as *Escherichia coli, Bacillus subtilis*, actinomyces, yeast, filamentous fungus, a plant cell, an insect cell and an animal cell, to obtain a transformant. From the cultured product of the transformant, a peptide containing the amino acid sequence of the invention can be obtained. Alternatively, DNA encoding the amino acid sequence of the invention is prepared and subjected to an acellular protein-synthesis system using wheat germ and a cell extract from *Escherichia coli*, etc to synthesize the peptide of the invention. Moreover, using a customary chemical synthesis method for a peptide such as a "solid phase method" or "a liquid phase method", amino acids represented by the amino acid sequence of the invention are successively connected and extended by dehydration/condensation. In this manner, the peptide of the invention composed of the amino acid sequence of the invention can be synthesized. Furthermore, when the peptide of the invention composed of the amino acid sequence of the invention is connected to a desired original peptide, a polymeric peptide of the invention (higher in molecular weight) containing the amino acid sequence of the invention can be synthesized.

Since the peptide of the invention has the amino acid sequence of the invention, a solution containing a product from a transformant is brought into contact with a surface of a solid phase to allow the peptide of the invention to adsorb directly to the surface of the solid phase. In this manner, the peptide of the invention can be separated and purified. The solution containing a product refers to any one of the solutions containing the peptide of the invention to be desired and an unnecessary contaminant derived from a host. Examples thereof include a solution of crushed bacterial cells, a soluble fraction centrifugally obtained from the solution of crushed bacterial cells, a solution solubilizing an insoluble fraction centrifugally obtained from the solution of crushed bacterial cells, a cell membrane fraction, a cell wall fraction, a secretion derived from cells, a body fluid or an incompletely purified product.

Furthermore, when a large amount of xenogeneic gene is expressed in a host by introducing recombinant DNA thereto, the peptide of the invention is sometimes produced in the form of an insoluble and inert aggregate, i.e., an inclusion body, to avoid a negative effect of the produced protein upon the host. Even if the peptide of the invention is produced in the form of an inclusion body, the inclusion body is solubilized by a denaturizing agent and immobilized as it is to a solid-phase surface. In addition, if the denaturing agent is removed while the peptide of the invention is immobilized, the peptide of the invention is sometimes refolded.

Furthermore, besides the case where the peptide of the invention is produced in the form of an inclusion body, in the case where the tertiary structures of the peptide is denatured by unknown causes, the peptide can be immobilized as it is to a solid-phase surface as long as it is the peptide of the invention. In addition, if an appropriate refolding buffer is added while the peptide of the invention is immobilized, the peptide of the invention can be refolded in some cases. Denaturation occurs by a physical cause due to heating, freezing, pressurizing, ultrasonic application, irradiation with UV rays or X-rays, stirring, adsorption and dilution, etc. and a chemical cause due to an extreme acidic or alkaline state, an organic solvent, a heavy metal salt, a denaturizing agent and a surfactant, etc.

As described above, since amino acid sequences 1 to 20 of the invention exhibit an excellent binding ability to a hydrophilic resin surface, the peptide of the invention having any one of amino acid sequences 1 to 20 of the invention can be immobilized directly to a solid phase having a hydrophilic resin surface. Thus, the peptide of the invention can be easily separated and purified. More specifically, a solution containing the peptide of the invention having any one of amino acid sequences 1 to 20 of the invention is allowed to pass through a column charged with a solid phase having a hydrophilic resin surface, thereby directly binding the peptide of the invention to a solid phase. In this manner, the peptide of the invention having any one of amino acid sequences 1 to 20 of the invention can be separated and purified.

The present invention will be more specifically described by way of examples; however, the present invention is not limited to these examples as long as it is not beyond the range of the gist. In Examples 1 to 19, the amino acid sequence of the invention was introduced into glutathione transferase (GST). In Example 20, the amino acid sequence of the invention was introduced into an antibody. In Examples 21 to 28, the amino acid sequence of the invention was introduced into a single-chain antibody. Note that, in the following Examples, the concentration of the peptide of the invention was determined by the Lowry method using bovine serum-derived albumin (BSA) as the standard protein.

Example 1

Biosynthesis of GST Having Amino Acid Sequence 2 of the Invention

First, a plasmid ("pGEX-3X", NCBI database/accession No: U13852, manufactured by GE Healthcare Bioscience) having a gene encoding glutathione transferase (GST) was used. A vector was prepared by introducing a gene encoding amino acid sequence 2 of the invention (the base sequence represented by Sequence ID No. 21 of the sequence listing) into the plasmid between the base sequence site recognized by restriction enzyme BamHI and the base sequence site recognized by restriction enzyme EcoRI.

Next, *Escherichia coli* (BL21) was used as a host. The vector having the gene encoding amino acid sequence 2 of the invention introduced therein was introduced into a host to transform the host. The transformant was screened on an agar medium containing ampicillin. Thereafter, *Escherichia coli* was cultured in 2×YT medium (50 ml) and an expression-inducing substance, namely, isopropyl 1-thio-galactoside (IPTG: Isopropyl-1-thio-β-D(−)-galactoside), was added so as to obtain a final concentration of 0.1 mM to allow GST (the peptide of the invention) containing amino acid sequence 2 of the invention to express.

Subsequently, bacterial cells were crushed. Thereafter, an intracellular soluble fraction was purified using purification gel (GSH-Sepharose 6B) and dialyzed against phosphate buffered saline (PBS) overnight to remove aggregates by a sterilization filter. In this manner, glutathione transferase (GST) having amino acid sequence 2 of the invention introduced in the C terminal was biologically synthesized as the peptide of the invention. Hereinafter, GST having amino acid sequence 2 of the invention biologically synthesized in Example 1 will be referred to as peptide 1 of the invention.

Example 2

Biosynthesis of GST Having Amino Acid Sequence 3 of the Invention

Glutathione transferase (GST) having amino acid sequence 3 of the invention introduced in the C terminal was biologically synthesized as the peptide of the invention, by the same treatment as in Example 1 except that a gene encoding amino acid sequence 3 of the invention (the base sequence represented by Sequence ID No. 22 of the sequence listing) was introduced into plasmid "pGEX-3X" between the base sequence site recognized by restriction enzyme BamHI and the base sequence site recognized by restriction enzyme EcoRI. Hereinafter, GST having amino acid sequence 3 of the invention biologically synthesized in Example 2 will be referred to as peptide 2 of the invention.

Examples 3 to 6

Biosynthesis of GSTs Having Amino Acid Sequences 4 to 7 of the Invention

Glutathione transferases (GST) having amino acid sequences 4 to 7 of the invention introduced in the C terminal were biologically synthesized as the peptide of the invention, by the same treatment as in Example 1 except that the genes encoding amino acid sequences 4 to 7 of the invention each were introduced into plasmid "pGEX-3X" between the base sequence site recognized by restriction enzyme BamHI and the base sequence site recognized by restriction enzyme EcoRI. Note that, in Example 3, GST having amino acid sequence 4 of the invention was biologically synthesized. In Example 4, GST having amino acid sequence 5 of the invention was biologically synthesized. In Example 5, GST having amino acid sequence 6 of the invention was biologically synthesized. In Example 6, GST having amino acid sequence 7 of the invention was biologically synthesized. Hereinafter, GSTs having amino acid sequences 4 to 7 of the invention biologically synthesized in Examples 3 to 6, respectively will be referred to as peptides 3 to 6 of the invention, respectively.

Examples 7 to 9

Biosynthesis of GSTs Having the Amino Acid Sequences 8 to 10 of the Invention

Glutathione transferases (GST) having amino acid sequences 8 to 10 of the invention introduced in the C terminal were biologically synthesized as the peptide of the invention, by the same treatment as in Example 1 except that genes encoding amino acid sequences 8 to 10 of the invention each were introduced into plasmid "pGEX-3X" between the base sequence site recognized by restriction enzyme BamHI and the base sequence site recognized by restriction enzyme EcoRI. Note that, in Example 7, GST having amino acid sequence 8 of the invention was biologically synthesized. In Example 8, GST having amino acid sequence 9 of the invention was biologically synthesized. In Example 9, GST having amino acid sequence 10 of the invention was biologically synthesized. Hereinafter, GSTs having amino acid sequences 8 to 10 of the invention biologically synthesized in Examples 7 to 9 will be referred to as peptides 7 to 9 of the invention.

Example 10

Evaluation on the Binding Ability of Peptides 1 and 2 of the Invention to a Hydrophilic Polystyrene Surface, Contaminant: BSA To evaluate the binding ability of the peptide of the invention to a hydrophilic polystyrene surface, the immobilization ratios of peptide 1 of the invention in Example 1, peptide 2 of the invention in Example 2 and the original peptide, i.e., GST, to a hydrophilic polystyrene surface were determined in the presence of bovine serum-derived albumin (BSA) serving as a contaminant.

First, PBS containing no BSA and PBS containing BSA to a concentration of 0.003 to 50 mg/ml were prepared. To each of the solutions, peptide 1 of the invention was added so as to obtain a final concentration of 5 μg/ml to prepare samples. Next, each (100 μl) of the samples was placed in a hydrophilic polystyrene plate ("IWAKI microplate #3860-096" manufactured by AGC Techno Glass Co., Ltd.), incubated at room temperature for one hour to immobilize peptide 1 of the invention, and washed five times with PBS (hereinafter referred to as "0.1PBST") containing 0.1% Tween 20. Furthermore, 0.1PBST (300 μl) containing 2% BSA was added as a blocking reagent, incubated at room temperature for one hour to block unbound sites of a polystyrene plate surface, and washed five times with 0.1PBST. Subsequently, as an antibody, anti-GST antibody (100 μl) diluted 4000 fold with 0.1PBST containing 0.2% BSA was added and incubated at room temperature for one hour to perform an antigen-antibody reaction between GST contained in peptide 1 of the invention and the anti-GST antibody and washed five times with 0.1PBST. Thereafter, as an enzyme-labeled second antibody, HRP-conjugated anti-rabbit IgG antibody (100 μl) diluted 1000 fold with 0.1PBST containing 0.2% BSA was added, incubated at room temperature for one hour to perform an antigen-antibody reaction, and washed five times with 0.1PBST. Finally, as a chromogenic substrate, ABTS (2,2'-azinobis(3-ethylbenzthiazoline-6-sulphonic acid)) was added and incubated. Using a microplate reader ("SUNRISE Remote" manufactured by TECAN), absorbance at 405 nm was measured. The same treatment was applied to peptide 2 of the invention and GST and absorbance was measured.

Measurement results of Example 10 are shown in FIG. 1. In FIG. 1, a solid circle (●) indicates the result of peptide 1 of the invention; a solid triangle indicates the result of peptide 2 of the invention; and an open circle (○) indicates the result of the original peptide, i.e., GST. Note that, in FIG. 1, the vertical axis indicates the immobilization ratio (%) and the transverse axis indicates the BSA concentration. The immobilization ratio is obtained by normalizing absorbance values (absorbance values other than the standard) based on the absorbance (binding amount) in PBS containing no BSA as a standard (100%).

From FIG. 1, it can be confirmed that the immobilization ratio of the original peptide, i.e., GST, rapidly reduces and the binding amount reduces if BSA is present as a contaminant; however, the immobilization ratios of peptides 1 and 2 of the invention do not virtually change even if BSA is present in a concentration as high as 10 mg/ml, and that these peptides can specifically bind to a hydrophilic polystyrene plate.

Example 11

Evaluation on the Binding Ability of Peptide 1 of the Invention to a Hydrophilic Polystyrene Surface, Contaminant: BSA and Tween 20

To evaluate the binding ability of peptide 1 of the invention according to Example 1 more specifically, the binding amounts thereof (absorbance) to a hydrophobic polystyrene surface and a hydrophilic polystyrene surface were measured in the presence of a contaminant, Tween 20.

First, PBS containing no Tween 20 and PBS samples containing Tween 20 so as to obtain a concentration of 0.1, 1 and 10% were prepared. To each of the solutions, peptide 1 of the invention was added so as to obtain a final concentration of 0 to 1 μg/ml to prepare samples.

Next, each (100 μl) of the samples was placed in a hydrophilic polystyrene plate ("IWAKI microplate #3860-096" manufactured by AGC Techno Glass Co., Ltd.) and a hydrophobic polystyrene plate ("BD Falcon microplate #351172" manufactured by Becton, Dickinson and Company), incubated at room temperature for one hour to immobilize peptide 1 of the invention, and washed five times with 0.1PBST. Thereafter, a treatment for adding a blocking reagent, an antibody, an enzyme labeled second antibody and a chromogenic substrate and a washing treatment were performed in the same conditions as in Example 10, and absorbance was measured. The same treatment was applied to the original peptide, i.e., GST, and absorbance was measured.

FIG. 2(a) to (d) shows measurement results in the hydrophilic polystyrene plate of Example 11, whereas FIG. 3(a) to (d) shows measurement results in the hydrophobic polystyrene plate of Example 11. FIG. 2(a) to (d) and FIG. 3(a) to (d) are measurement results in the conditions where the addition amount of Tween 20 was 0, 0.1, 1 and 10%, respectively. In FIG. 2 and FIG. 3, a solid circle (●) indicates the result of peptide 1 of the invention and an open circle (○) indicates the result of the original peptide, i.e., GST. In FIGS. 2 and 3, the vertical axis indicates absorbance at 405 nm and the transverse axis indicates the concentration of peptide 1 of the invention and GST. Note that, in FIGS. 2 and 3, if the result of GST and result of peptide 1 of the invention are the same, an open circle (○) indicating the result of GST is overlapped with a solid circle (●) indicating peptide 1 of the invention and cannot be checked. For example, in FIG. 3(b) to (d), all open circles of GST (○) are overlapped with a solid circle (●) indicating peptide 1 of the invention.

From FIG. 2(a) to (d), it can be confirmed that both of peptide 1 of the invention and GST increase in binding amount to a hydrophilic polystyrene plate as the concentration (addition amount) thereof increases. Furthermore, in peptide 1 of the invention, the binding amount to the hydrophilic polystyrene plate does not reduce and rather slightly increases even if Tween 20 is added as a contaminant. In GST, the binding amount to the hydrophilic polystyrene plate slightly decreases when Tween 20 was added as a contaminant.

Furthermore, according to FIG. 3(a), both of peptide 1 of the invention and GST bind to a hydrophobic polystyrene plate in absence of a contaminant, Tween 20. However, as shown in FIG. 3(b) to (d), neither peptide 1 of the invention nor GST virtually bind to a hydrophobic polystyrene plate in the presence of a contaminant, Tween 20. Likewise, the binding ability of the peptide of the invention is determined specifically to a solid phase having a hydrophilic resin surface.

Example 12

Evaluation on the Binding Ability of Peptide 1 of the Invention to a Hydrophilic Polystyrene Surface, Contaminant: BSA and Tween 20

To evaluate the binding ability of peptide 1 of the invention according to Example 1 more specifically, the binding amounts (absorbance) to a hydrophobic polystyrene surface and a hydrophilic polystyrene surface were measured in the presence of Tween 20 and in the presence of Tween 20 and BSA as a contaminant, while changing the addition amount of peptide 1 of the invention.

First, PBS, 0.1PBST and 0.1PBST containing a 20 mg/ml BSA were prepared. To each of the solutions, peptide 1 of the invention was added so as to obtain a final concentration of 0 to 10 μg/ml to prepare samples. Next, each sample (100 μl) was placed in a hydrophilic polystyrene plate ("IWAKI microplate #3860-096" manufactured by AGC Techno Glass Co., Ltd.) and a hydrophobic polystyrene plate ("BD Falcon microplate #351172" manufactured by Becton, Dickinson and Company), incubated at room temperature for two hours to immobilize peptide 1 of the invention and washed five times with 0.1PBST. Thereafter, in the same conditions as in Example 10, a treatment for adding a blocking reagent, an antibody, an enzyme labeled second antibody and a chromogenic substrate and a washing treatment were performed and absorbance was measured. The same treatment was applied to the original peptide, i.e., GST, and absorbance was measured.

Figure 4:
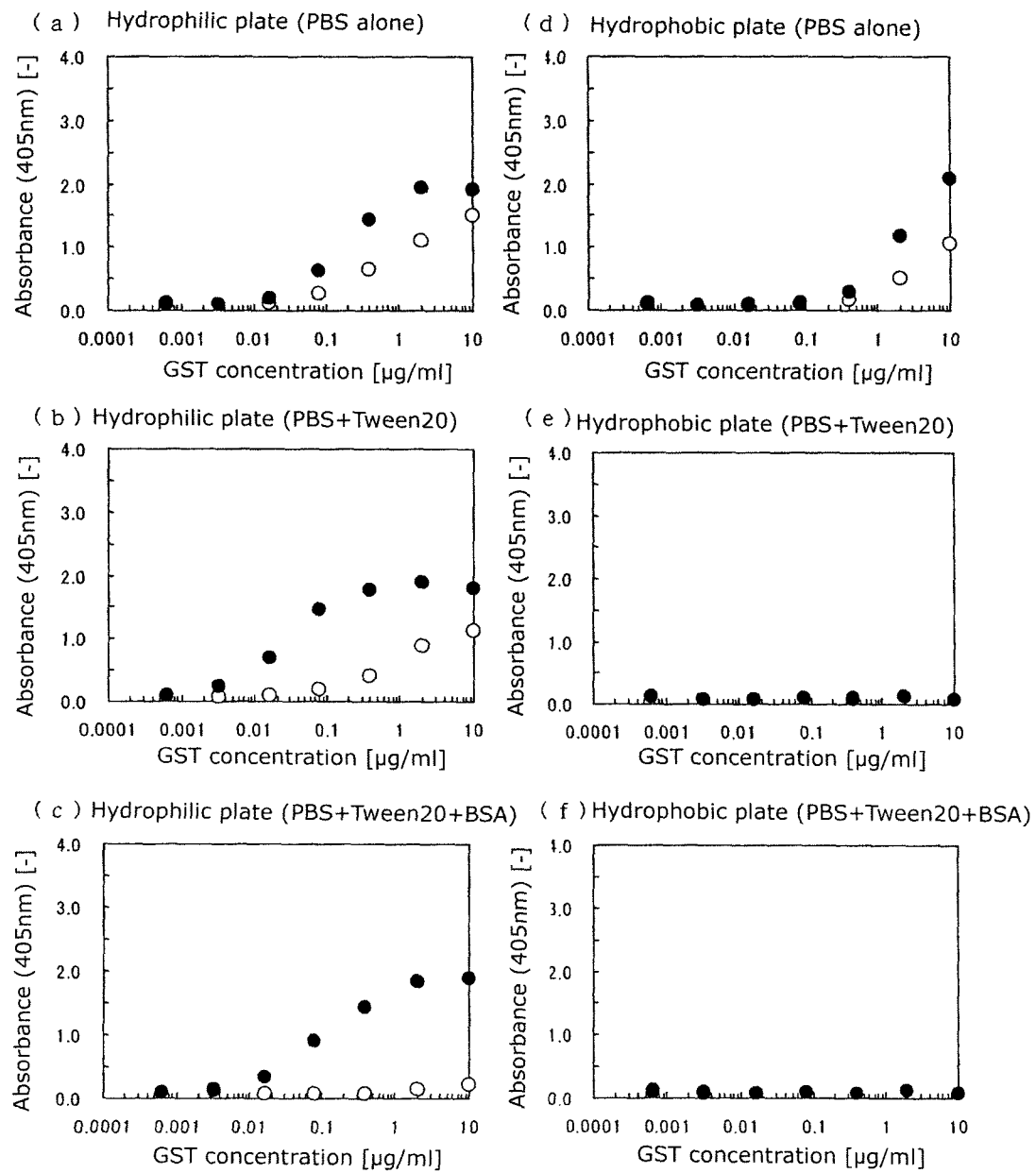
FIG. 4(a) to (f) are graphs showing the binding ability to hydrophilic and hydrophobic polystyrene plates in the presence of various contaminants.

FIG. 4 shows measurement results of Example 12. FIG. 4(a) to (c) shows measurement results of a hydrophilic polystyrene plate in PBS, 0.1PBST and 0.1PBST containing BSA, respectively. FIG. 4(d) to (f) show measurement results of a hydrophobic polystyrene plate in PBS, 0.1PBST and 0.1PBST containing BSA, respectively. Furthermore, in FIG. 4, a solid circle (●) indicates the result of peptide 1 of the invention and an open circle (○) indicates the result of the original peptide, i.e., GST. In FIG. 4, the vertical axis indicates absorbance at 405 nm and the transverse axis indicates the concentrations of peptide 1 of the invention and GST. Note that, in FIG. 4, if the result of GST and result of peptide 1 of the invention are the same, an open circle (○) indicating the result of the GST is overlapped with a solid circle (●) indicating peptide 1 of the invention and cannot be checked. For example, in FIGS. 4(e) and (f), all open circles (○) of GST are overlapped with solid circles (●) indicating peptide 1 of the invention.

From FIGS. 4(a) to (c), it can be confirmed that even when Tween 20 is added as a contaminant (FIG. 4(b)) and when Tween 20 and BSA is added as a contaminant (FIG. 4(c)), the binding amount of peptide 1 of the invention to a hydrophilic polystyrene plate does not virtually changed (solid circles in FIGS. 4(b) and (c)). In contrast, the binding amount of GST to a hydrophilic polystyrene plate slightly decreases (open circles in FIG. 4(b)) when Tween 20 is added as a contaminant. Furthermore, when BSA is added, binding cannot be virtually made (open circles in FIG. 4(c)). Likewise, the binding ability to a hydrophilic polystyrene plate is improved by introducing amino acid sequence 2 of the invention.

Furthermore, according to FIGS. 4(d) to (f), both of peptide 1 of the invention and GST bind to a hydrophobic polystyrene plate in absence of a contaminant, Tween 20, but cannot virtually bind to a hydrophobic polystyrene plate in the presence of Tween 20 and BSA as a contaminant.

Example 13

Evaluation on Activity Value of Peptide 1 of the Invention

To evaluate the activity value of peptide 1 of the invention according to Example 1 in an immobilization state, peptide 1 of the invention was allowed to bind to a hydrophobic polystyrene surface and a hydrophilic polystyrene surface in the presence of Tween 20 and in the presence of Tween 20 and BSA as a contaminant and the enzymatic activity value of the GST immobilized was measured.

First, PBS, 0.1PBST and 0.1PBST containing 20 mg/ml BSA were prepared. To each of the solutions, peptide 1 of the invention was added so as to obtain a final concentration of 10, 20 and 40 µg/ml to prepare samples. Next, each sample (100 µl) was placed in a hydrophilic polystyrene plate ("IWAKI microplate #3860-096" manufactured by AGC Techno Glass Co., Ltd.) and a hydrophobic polystyrene plate ("BD Falcon microplate #351172" manufactured by Becton, Dickinson and Company), incubated at room temperature for two hours to immobilize peptide 1 of the invention and washed five times with 0.1PBST. Thereafter, 200 µl of a 0.1M potassium phosphate buffer (pH6.5) containing 0.1% Tween 20, 1 mM reduced-form glutathione and 1 mM CDNB (1-chloro-2,4-dinitrobenzene) serving as a substrate for GST was added and stirred at room temperature for 30 minutes. Absorbance at 340 nm was measured every 30 seconds. The same treatment was applied to the original peptide, i.e., GST, and absorbance was measured.

Figure 5:
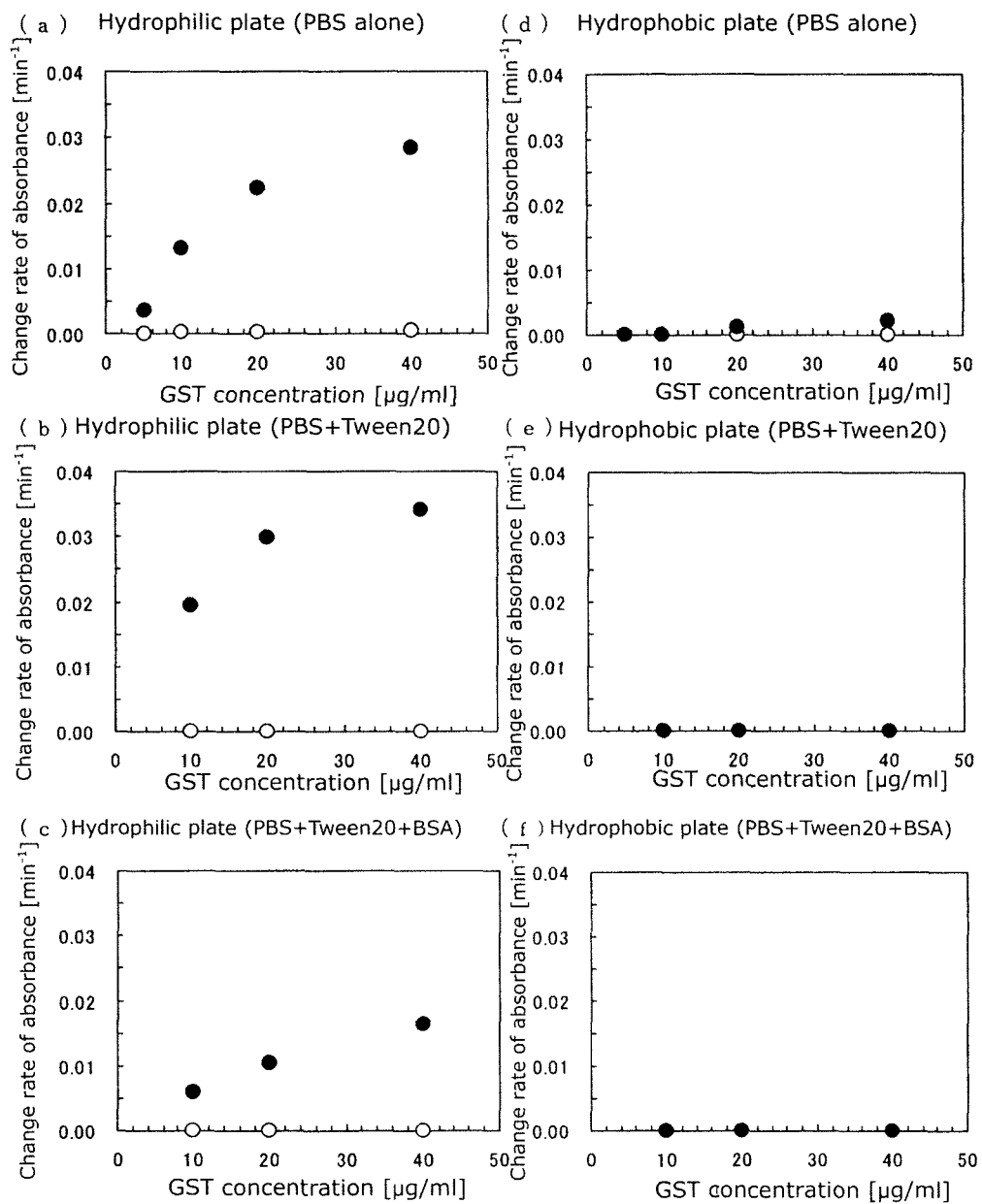
FIG. 5(a) to (f) are graphs showing the activity value to hydrophilic and hydrophobic polystyrene plates in the presence of various contaminants.

FIG. 5 shows the measurement results of Example 13. FIGS. 5(a) to (c) show measurement results of a hydrophilic polystyrene plate in PBS, 0.1PBST and 0.1PBST containing BSA, respectively. FIGS. 5(d) to (f) show measurement results of a hydrophobic polystyrene plate in PBS, 0.1PBST and 0.1PBST containing BSA, respectively. Furthermore, in FIG. 5, a solid circle (●) indicates the result of peptide 1 of the invention and an open circle (○) indicates the result of the original peptide, i.e., GST. In FIG. 5, the vertical axis indicates the activity value (the change rate of absorbance) and the transverse axis indicates the concentrations of peptide 1 of the invention and GST. Note that, in FIG. 5, if the result of GST and result of peptide 1 of the invention are the same, an open circle (○) indicating the result of the GST is overlapped with a solid circle (●) of peptide 1 of the invention and cannot be checked. For example, in FIGS. 5(e) and (f), all open circles (○) of GST are overlapped with solid circles (●) indicating peptide 1 of the invention.

From FIGS. 5(a) to (c), it can be confirmed that GST of peptide 1 of the invention immobilized to a hydrophilic polystyrene plate is very active as an enzyme, even when Tween 20 is added as a contaminant (FIG. 5(b)) and even when Tween 20 and BSA are added as a contaminant (FIG. 5(c)). In contrast, GST binds to the hydrophilic polystyrene plate when no contaminant was added and when Tween 20 is added as a contaminant as shown by open circles of FIGS. 4(a) and (b) in connection with in Example 12; however no enzymatic activity is seen as shown in FIGS. 5(a) and (b). This means that the original peptide, i.e., GST, is immobilized to a hydrophilic polystyrene plate but configurational change and inactivation occur. Note that, GST shows no enzymatic activity also in FIG. 5(c). This is because GST virtually cannot bind to a hydrophilic polystyrene plate in the presence of Tween 20 and BSA, as shown in FIG. 4(c).

Furthermore, from FIG. 5(d), it can be confirmed that GST of peptide 1 of the invention immobilized to a hydrophobic polystyrene plate virtually exhibit no enzymatic activity. As is apparent from FIG. 4(d) in connection with Example 12, peptide 1 of the invention can bind to a hydrophobic polystyrene plate in the absence of a contaminant; however, it loses the activity due to configuration change and inactivation. In short, it can be confirmed that the biding ability of amino acid sequence 2 of the invention is specific to a hydrophilic polystyrene plate and that activity can be maintained in the case where peptide 1 of the invention is immobilized to a hydrophilic polystyrene plate rather than the case where it is immobilized to a conventional hydrophobic polystyrene plate. Note that, in FIGS. 5(e) and (f), neither peptide 1 of the invention nor GST exhibits enzymatic activity. This is because no binding is made to a hydrophobic polystyrene plate in the presence of Tween 20 and BSA as a contaminant.

Example 14

Evaluation on the Binding Ability of Peptides 3 to 6 of the Invention to a Hydrophilic Polystyrene Surface, Contaminant: BSA and Tween 20

To evaluate the binding ability of peptides 3 to 6 of the invention obtained in Examples 3 to 6, the immobilization ratios of peptides 3 to 6 of the invention, peptide 1 of the invention and the original peptide, i.e., GST, to a hydrophilic polystyrene surface were measured in the presence of BSA and Tween 20 as a contaminant.

First, 0.1PBST containing no BSA, 0.1PBST having a BSA concentration of 0.003 to 50 mg/ml were prepared. To each of the solutions, peptide 3 of the invention was added so as to obtain a final concentration of 5 µg/ml to prepare samples. Next, each sample (100 µl) was placed in a hydrophilic polystyrene plate ("IWAKI microplate #3860-096" manufactured by AGC Techno Glass Co., Ltd.) and incubated at 25° C. for three hours to immobilize peptide 3 of the invention and washed six times with 0.1% PBS. Furthermore, a 0.1PBST containing 2% BSA (300 µl) was added as a blocking reagent and incubated at 25° C. for one hour to block unbound sites on the polystyrene plate surface and washed six times with 0.1PBST. Subsequently, an anti-GST antibody (100 µl) diluted 5000 fold with 0.1PBST containing 0.2% BSA was added as an antibody and incubated at 25° C. for one hour to perform the antigen-antibody reaction between GST contained in peptide 3 of the invention and the anti-GST antibody and washed six times with 0.1PBST. Thereafter, as an enzyme labeled second antibody, HRP-conjugated anti-rabbit IgG antibody (100 µl) diluted 5000 fold with 0.1PBST containing 0.2% BSA was added, incubated at 25° C. for one hour to perform an antigen-antibody reaction and washed further six times with 0.1PBST. Finally, as a chromogenic substrate, ABTS (2,2'-azinobis(3-ethylbenzthiazoline-6-sulphonic acid)) was added and incubated. Using a microplate reader ("SUNRISE Remote" manufactured by TECAN), absorbance at 405 nm was measured. The same treatment was applied to the peptides 4 to 6 of the invention, peptide 1 of the invention and GST and absorbance was measured.

Figure 7:
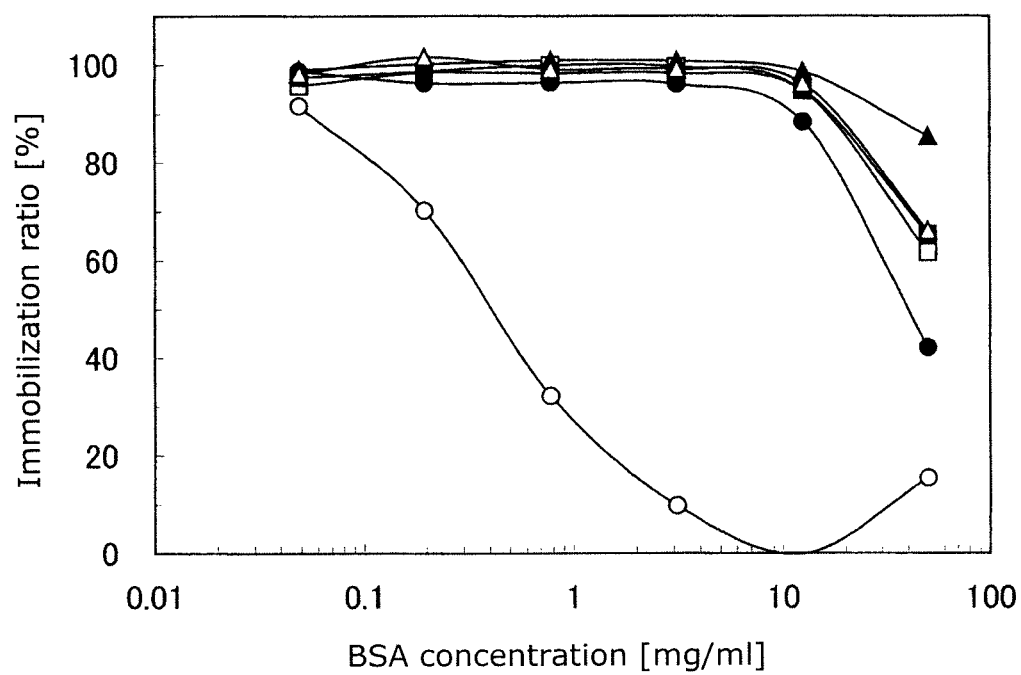
FIG. 7 is a graph showing the immobilization ratio to a hydrophilic polystyrene surface in the presence of BSA.

FIG. 7 shows the measurement results of Example 14. In FIG. 7, a solid triangle indicates the result of peptide 3 of the invention; open triangle (Δ) indicates the result of peptide 4 of the invention; solid square indicates the result of peptide 5 of the invention; open square (□) indicates the result of peptide 6 of the invention; a solid circle (●) indicates the result of peptide 1 of the invention; and an open circle (○) indicates the result of the original peptide, i.e., GST. In FIG. 7, the vertical axis indicates the immobilization ratio (%) and the transverse axis indicates the BSA concentration. The immobilization ratio is obtained by normalizing absorbance values (absorbance values other than the standard) based on the absorbance (binding amount) in PBST containing no BSA as a standard (100%). Note that, in FIG. 7, the results of peptides 1, 3 to 6 of the invention are analogous and partly overlapped.

From FIG. 7, it can be confirmed that in the presence of a BSA and Tween 20 as a contaminant, the immobilization ratio of the original peptide, i.e., GST, rapidly decreases and the binding amount reduces; whereas, the immobilization ratios of peptides 3 to 6 of the invention do not virtually change, even if BSA is present in an amount as large as 10 mg/ml, and these peptides specifically bind to a hydrophilic polystyrene plate at the same level as in peptide 1 of the invention.

Example 15

Evaluation on Activity Values of Peptides 3 to 6 of the Invention to a Polystyrene Surface, Contaminant: BSA and Tween 20

To evaluate the activity values of peptides 3 to 6 of the invention immobilized to a hydrophilic polystyrene surface, the enzymatic activity value of GST immobilized was measured each in the presence of Tween 20 and in the presence of Tween 20 and BSA as a contaminant.

First, PBS and 0.1PBST were prepared. To each of the solutions, peptides 1, 3 to 6 of the invention were added separately so as to obtain a final concentration of 0.5, 10, 20 and 40 μg/ml to prepare samples. Next, each sample (100 μl) was placed in a hydrophilic polystyrene plate ("IWAKI microplate #3860-096" manufactured by AGC Techno Glass Co., Ltd.), incubated at 25° C. for two hours to immobilize the peptide of the invention and washed six times with 0.1PBST and washed once with 0.1M potassium phosphate solution (pH6.5) containing 0.1% Tween 20. Thereafter, 200 μl of 0.1M potassium phosphate buffer (pH6.5) containing 0.1% Tween 20, 1 mM reduced-form glutathione and 1 mM CDNB (1-chloro-2,4-dinitrobenzene) serving as a substrate for GST, was added. While stirring at room temperature for 30 minutes, absorbance at 340 nm was measured every 30 seconds. The same treatment was applied to the original peptide, i.e., GST, and absorbance was measured.

Figure 8:
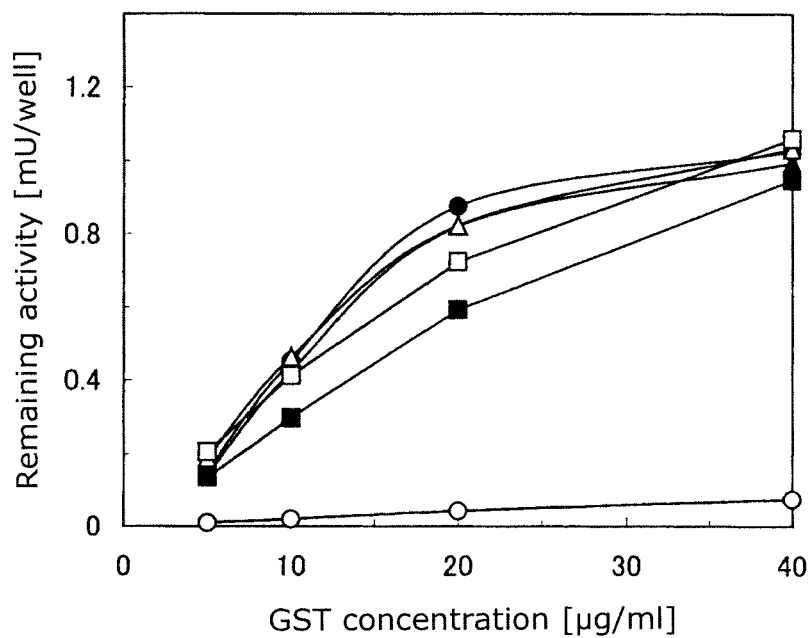
FIGS. 8(a) and (b) are graphs each showing the activity value to a hydrophilic polystyrene plate in the presence of various contaminants.
Figure 8:
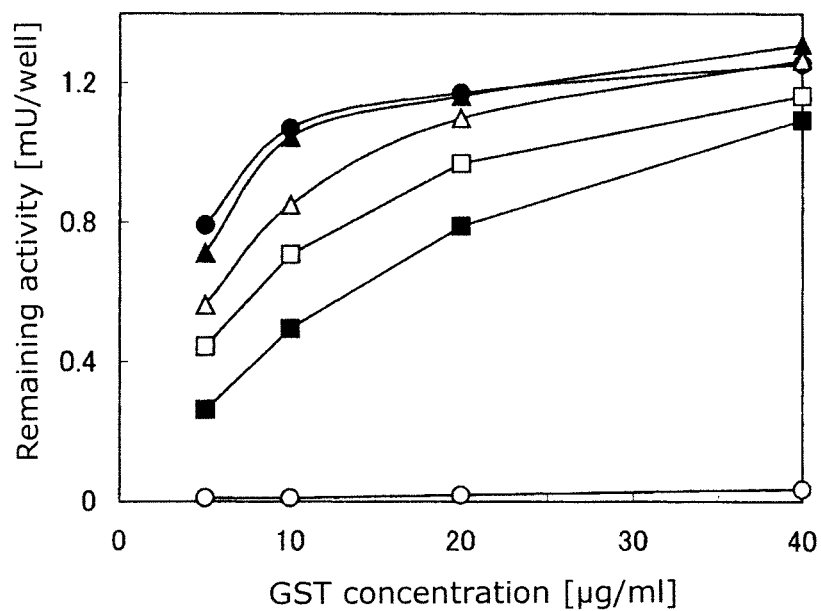

FIG. 8 shows the measurement results of Example 15. FIG. 8(a) shows the measurement results in PBS and (b) shows the measurement results in 0.1PBST. Furthermore, in FIG. 8, a solid triangle indicates the result of peptide 3 of the invention; an open triangle (Δ) indicates the result of peptide 4 of the invention; a solid square indicates the result of peptide 5 of the invention; an open square (□) indicates the result of peptide 6 of the invention; a solid circle (●) indicates the result of peptide 1 of the invention; and an open circle (○) indicates the result of the original peptide, i.e., GST. In FIG. 8, the vertical axis indicates the activity value (the change rate of absorbance) and the transverse axis indicates the concentrations of the peptide of the invention and GST. Note that, in FIG. 8, the results of peptides 1, 3 to 6 of the invention are analogous and partly overlapped.

From FIGS. 8(a) and (b), it was confirmed that GST of peptides 1, 3 to 6 of the invention immobilized to a hydrophilic polystyrene plate are enzymatically very active not only as it is (FIG. 8(a)) but also in the presence of Tween 20 as a contaminant (FIG. 8(b)).

Example 16

Evaluation on the Binding Ability of Peptides 7 to 9 of the Invention to a Hydrophilic Polystyrene Surface, Contaminant: BSA and Tween 20

To evaluate the binding ability of peptides 7 to 9 of the invention biologically synthesized in Examples 7 to 9 to a hydrophilic polystyrene surface, peptides 7 to 9 of the invention and the original peptide, i.e., GST, were subjected to the same treatment as in Example 14 and absorbance was measured. In this manner, the immobilization ratio to the hydrophilic polystyrene surface was evaluated.

Figure 9:
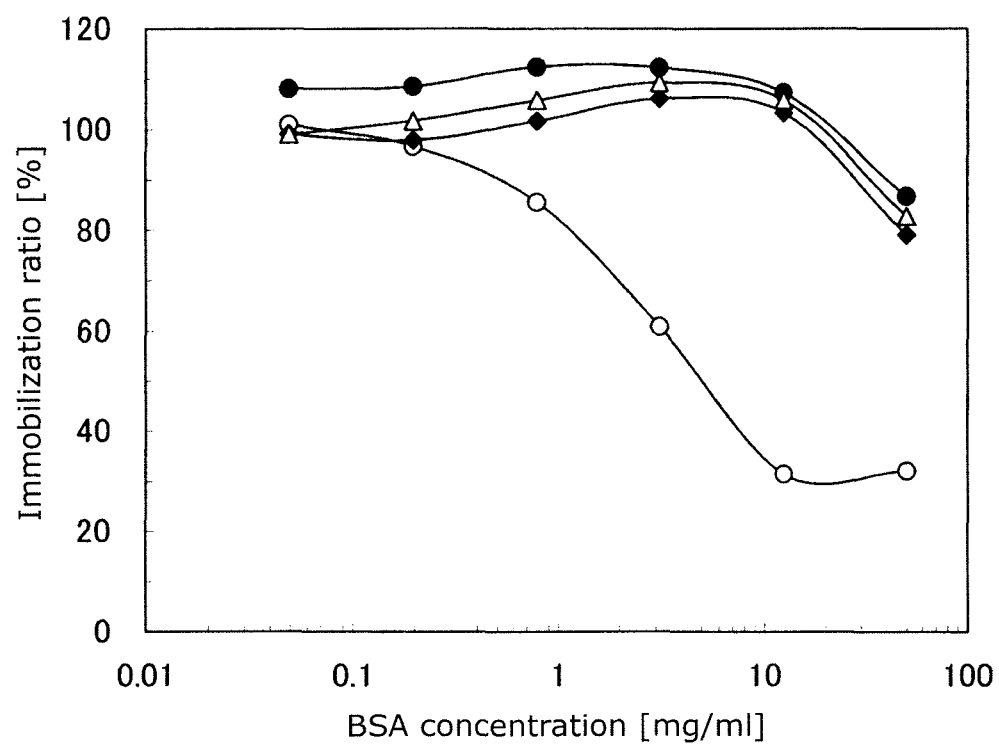
FIG. 9 is a graph showing the immobilization ratio to a hydrophilic polystyrene surface in the presence of BSA.

FIG. 9 shows the measurement results of Example 16. In FIG. 9, a solid triangle indicates the results of peptide 7 of the invention; an solid lozenge indicates the result of peptide 8 of the invention; an open triangle (Δ) indicates the result of peptide 9 of the invention; and an open circle (○) indicates the result of the original peptide, i.e., GST. In FIG. 9, the vertical axis indicates the immobilization ratio (%) and the transverse axis indicates the BSA concentration. The immobilization ratio is obtained by normalizing absorbance values (absorbance values other than the standard) based on the absorbance (binding amount) in PBST containing no BSA as a standard (100%).

From FIG. 9, it was confirmed that the immobilization ratio rapidly decreases and the binding amount reduces in the original peptide, i.e., GST, in the presence of BSA and Tween 20 as a contaminant; whereas, the immobilization ratios of peptides 7 to 9 of the invention, even if BSA is present in an amount as large as 10 mg/ml, do not virtually change, and these peptides specifically bind to a hydrophilic polystyrene plate.

Example 17

Evaluation on Activity Values of Peptides 7 to 9 of the Invention on a Polystyrene Surface, Contaminant: BSA and Tween 20

To evaluate the activity values of peptides 7 to 9 of the invention immobilized to a hydrophilic polystyrene surface, the same treatment as in Example 15 was applied to peptides 7 to 9 of the invention and the original peptide, i.e., GST and an activity value was measured.

Figure 10:
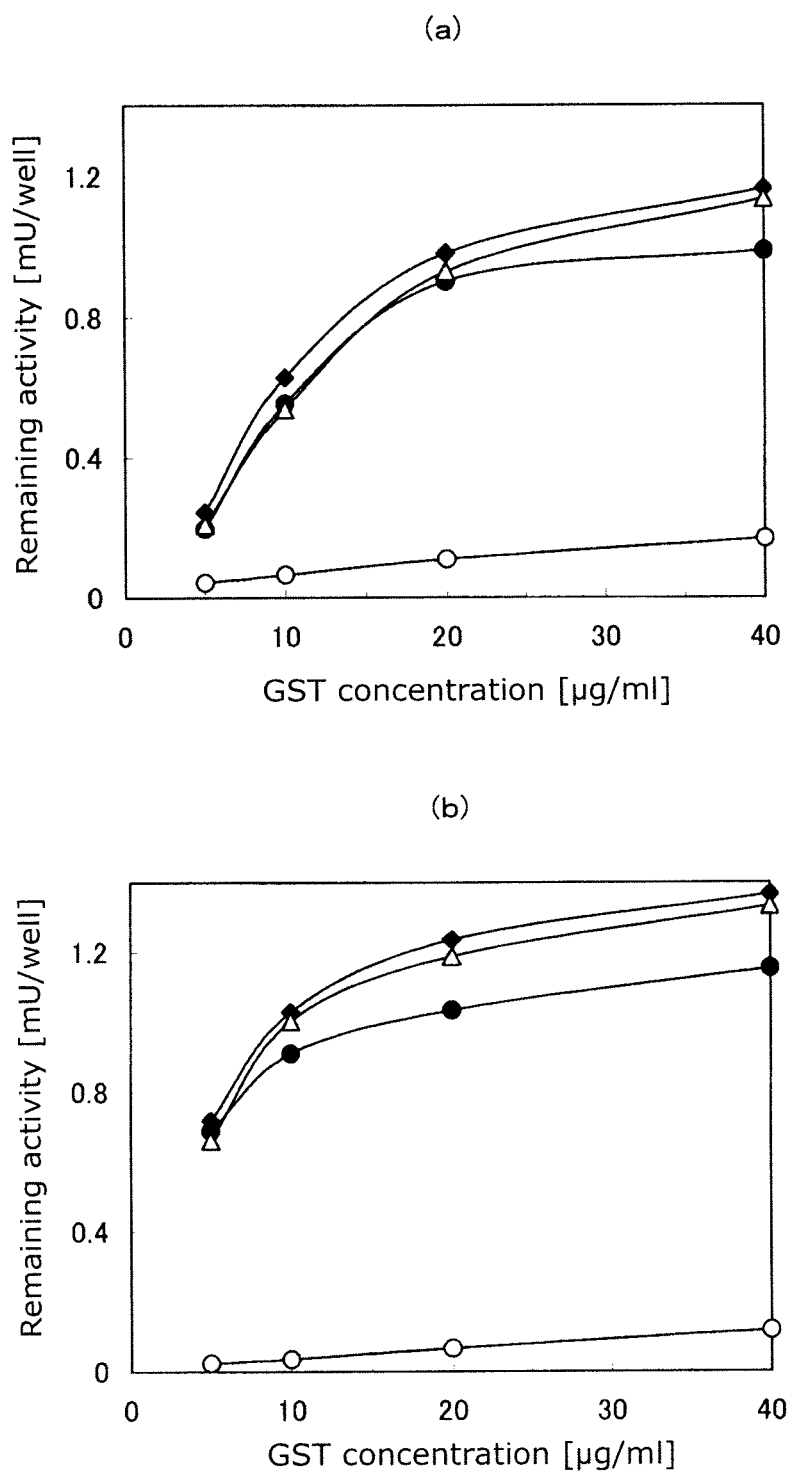
FIGS. 10(a) and (b) are graphs showing the activity value to a hydrophilic polystyrene plate in the presence of various contaminants.

FIG. 10 shows the measurement results of Example 17. FIG. 10(a) shows the measurement results in PBS and (b) shows the measurement results in 0.1PBST. Furthermore, in FIG. 10, a solid circle (●) indicates the result of peptide 7 the invention; a solid lozenge indicates the result of peptide 8 of the invention; an open triangle (Δ) indicates the result of peptide 9 of the invention; and an open circle (○) indicates the result of the original peptide, i.e., GST. In FIG. 10, the vertical axis indicates the activity value (the change rate of absorbance) and the transverse axis indicates the concentrations of the peptide of the invention and GST.

From FIGS. 10(a) and (b), it was confirmed that GST of peptides 7 to 9 of the invention immobilized to a hydrophilic polystyrene plate are enzymatically very active not only as it is (FIG. 10(a)) but also in the presence of Tween 20 as a contaminant (FIG. 10(b)).

Example 18

Application Example of Peptide 1 of the Invention to Separation/Purification Step in a Production Process, Contaminant: Solution of Crushed Bacterial Cells In this Example, to evaluate applicability of a specific adsorption function of the peptide of the invention to a separation/purification step of a production process, GST containing amino acid sequence 2 of the invention expressed by use of *Escherichia coli* was used without a special purification step. More specifically, a solution of crushed bacterial cells was directly subjected to an immobilization to a hydrophilic polystyrene surface and a binding amount (absorbance) was measured. For comparison, the original peptide, i.e., GST, was used and the binding amount (absorbance) was measured in the same manner.

Figure 11:
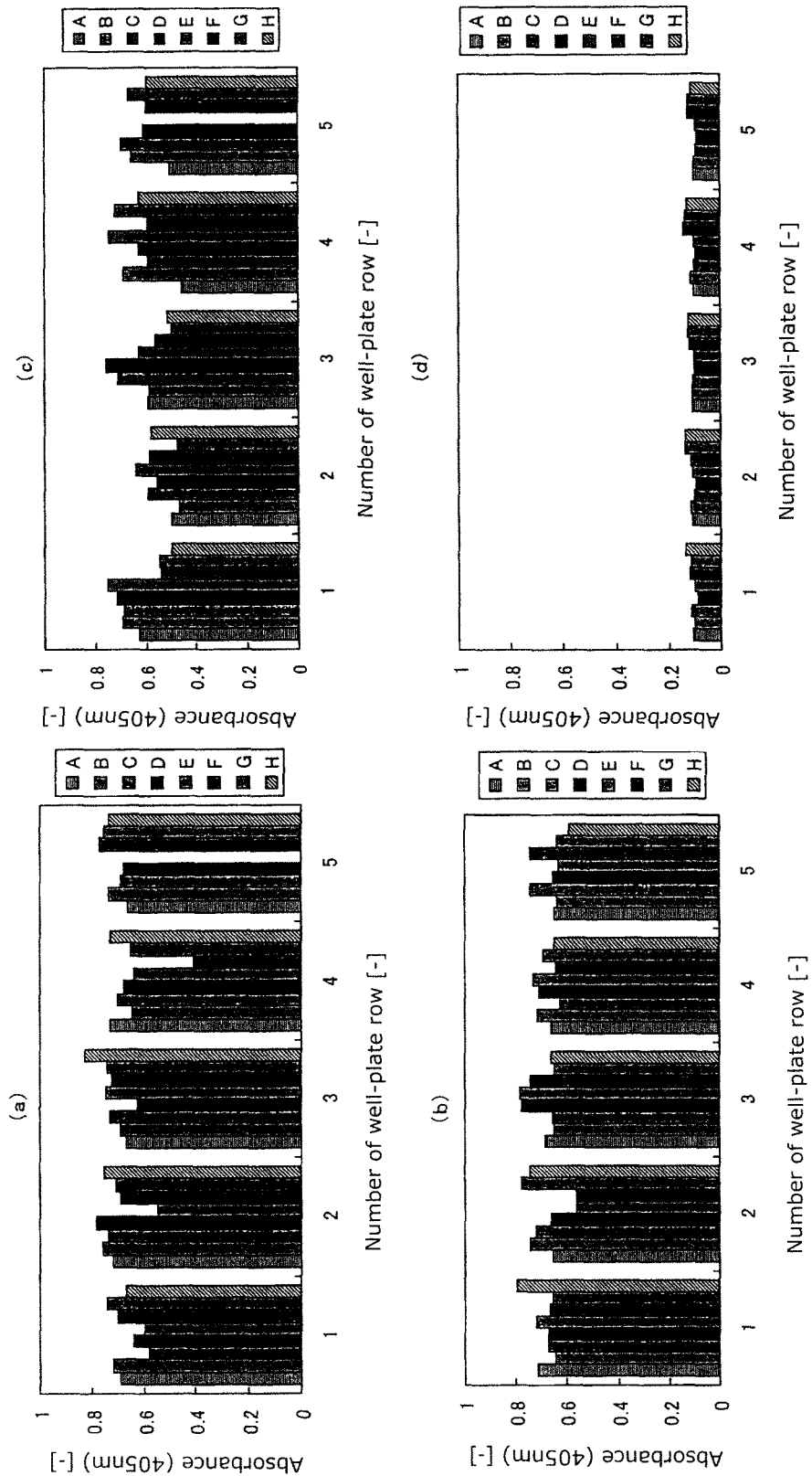
FIGS. 11(a) and (b) are graphs showing the bacterial cell concentrations in colonies obtained by culturing the peptide of the invention and the original peptide, respectively; (c) and (d) are graphs showing the binding abilities of the peptide of the invention and the original peptide, respectively.

First, a well plate, in which 8 culture containers (wells) were provided per row and consisting of 5 rows, was used. To each of 39 culture containers (wells), 2×YT medium (200 µl) was added. *Escherichia coli* (BL21), which was transformed by introducing a vector containing a gene encoding amino acid sequence 2 of the invention similarly to Example 1, was inoculated to form colonies and cultured at 37° C. at 200 rpm overnight. Similarly, 40 colonies of the original peptide, i.e., GST, were formed and cultured. To check degree of culturing, 100 µl of the culture solution was taken and bacterial cell concentration was measured. FIG. 11(a) shows bacterial cell concentration (absorbance at 630 nm) of 39 colonies obtained by culturing the peptide of the invention. FIG. 11(b) shows bacterial cell concentration (absorbance at 630 nm) of 40 colonies obtained by culturing the original peptide of the invention. In FIG. 11, the transverse axis indicates row No. of the well plate and shows the results of 8 wells per row. From FIGS. 11(a) and (b), it was confirmed that all colonies are cultured at the same level.

Next, after the bacterial cells were crushed, the solution (10 µl) of the crushed bacterial cells was taken, mixed with PBS (90 ml) containing 10 mg/ml BSA (1%), placed in a hydrophilic polystyrene plate ("IWAKI microplate #3860-096" manufactured by AGC Techno Glass Co., Ltd.) and incubated at room temperature for one hour to immobilize the peptide onto the solid phase. Thereafter, a treatment for adding a blocking reagent, an antibody, an enzyme labeled second antibody and a chromogenic substrate and a washing treatment were performed in the same conditions as in Example 7 and absorbance was measured. The same treatment was applied to the original peptide, i.e., GST, and absorbance was measured.

FIGS. 11(c) and (d) show the measurement results of Example 18. FIG. 11(c) shows absorbance (405 nm) of 39 colonies formed of the peptide of the invention cultured. FIG. 11(d) shows absorbance (405 nm) of 40 colonies formed of the original peptide cultured. As shown in FIG. 11(d), the original peptide, i.e., GST, had almost the same absorbance as that of background, meaning that most of the original peptide was not immobilized to a solid-phase surface. In contrast, as is confirmed from FIG. 11(c), the peptide of the invention, even if it is contained in a solution of crushed bacterial cells (*Escherichia coli*), is specifically immobilized to a solid-phase surface by bringing it into contact with the solid phase surface. The solution of crushed bacterial cell (*Escherichia coli*) contains not only unspecified various proteins in size but also lower-molecular weight compounds other than proteins and lipid as contaminants. Even if these contaminants are present, the peptide of the invention specifically binds to a hydrophilic polystyrene plate. Therefore, it was confirmed that the peptide of the invention can be used in a separation/purification step in a production process.

Example 19

Application Example of Peptide 1 of the Invention to a Separation/Purification Step in a Production Process, Contaminant: Medium In this Example, to evaluate on applicability of specific adsorption function of the peptide of the invention to a separation/purification step of a production process, binding of peptide 1 of the invention to a hydrophilic polystyrene surface was made in the presence of various types of mediums (YPD, BMMY, 2×TY, LB) serving as a contaminant and the binding amount (absorbance) thereof was measured. For comparison, the binding amount (absorbance) of the original peptide, i.e., GST, was measured in the same manner. YPD is general medium for culturing yeast; BMMY is a medium exclusively used for *P. pastoris*; and 2×TY and LB are mediums exclusively used for *Escherichia coli*.

First, four types of mediums, namely, YPD, BMMY, 2×TY and LB, were prepared. To each of the solutions including a stock solution to 10000-fold dilution solutions, peptide 1 of the invention was added so as to obtain 5 µg/ml to prepare samples. Each of the samples was placed in a hydrophilic polystyrene plate ("IWAKI microplate #3860-096" manufactured by AGC Techno Glass Co., Ltd.) and incubated at room temperature for one hour to immobilize the peptide onto a solid phase. Thereafter, a treatment for adding a blocking reagent, an antibody, an enzyme labeled second antibody and a chromogenic substrate and a washing treatment were performed in the same conditions as in Example 7 and absorbance was measured. The same treatment was applied to the original peptide, i.e., GST, and absorbance was measured. Absorbance of the original peptide, i.e., GST, was measured in the same manner.

Figure 12:
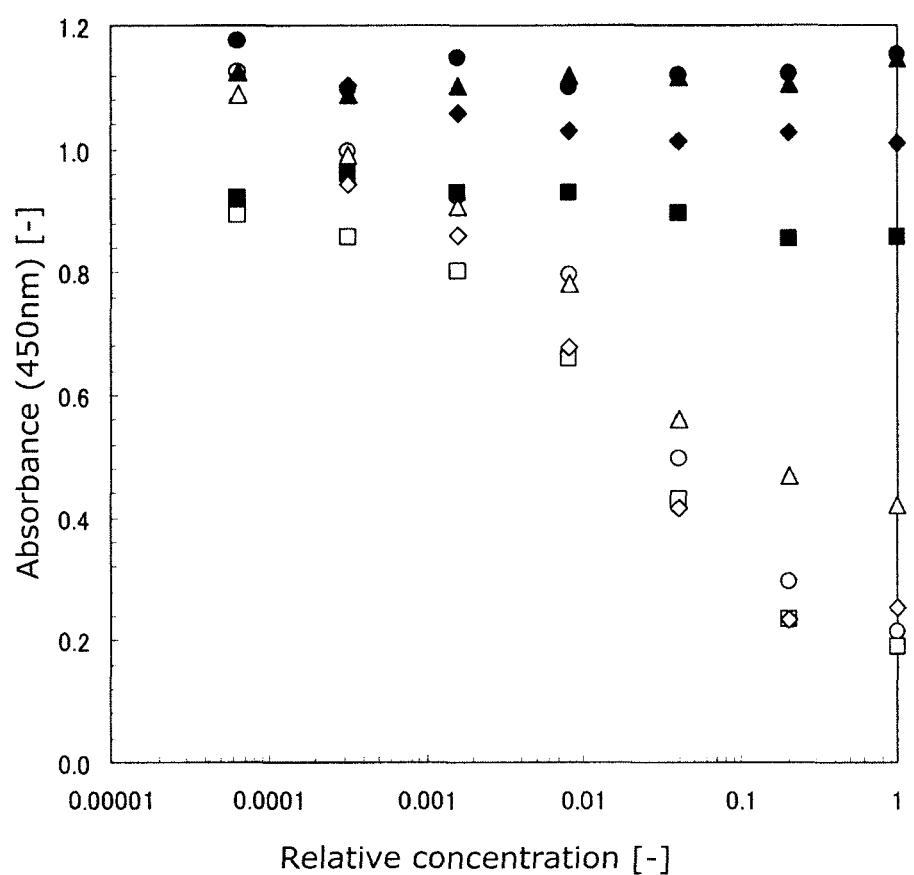
FIG. 12 is a graph showing the binding ability to a hydrophilic polystyrene plate in the states where various types of mediums are added as contaminants.

FIG. 12 shows the measurement results of Example 19. In FIG. 12, a solid circle (●) indicates the result of a sample of peptide 1 of the invention/medium YPD mixture; an open circle (○) indicates the result of a sample of the original peptide (GST)/medium YPD mixture; a solid triangle indicates the result of a sample of peptide 1 of the invention/medium BMMY mixture; an open triangle (Δ) indicates the result of a sample of the original peptide (GST)/medium BMMY mixture; a solid square indicates the result of a sample of peptide 1 of the invention/medium 2×YT mixture; an open square (□) indicates the result of a sample of the original peptide (GST)/medium2×YT mixture; lozenge (♦) indicates the results of a sample of peptide 1 of the invention/medium LB mixture; and an open lozenge (◇) indicates the result of a sample of the original peptide (GST)/medium LB mixture. In FIG. 12, the vertical axis indicates absorbance (405 nm) and the transverse axis indicates a relative concentration of medium (dilution rate) (number 1 on the right end indicates a stock solution). As shown in FIG. 12, the amount of original peptide, i.e., GST, (indicated by an open circle, open triangle, open square, open lozenge) that is bound to a solid-phase surface decreases as the concentration of the medium increases. In contrast, in peptide 1 of the invention (indicated by a solid circle, solid triangle, solid square, solid lozenge), even if the concentration of medium increases, a considerable amount of peptide is bound to a solid-phase surface by immobilization. It was confirmed that peptide 1 of the invention is immobilized specifically to a solid-phase surface regardless of the concentration of a medium.

Particularly, also in YPD for use in Yeast and BMMY, peptide 1 of the invention exhibits a specific adsorption ability. Thus, peptide 1 of the invention can be used in production from a yeast secretion. To describe more specifically, the peptide of the invention contained in a yeast secretion is immobilized by bringing the yeast secretion into direct contact with a solid-phase surface. In this manner, the peptide of the invention can be separated and purified.

Furthermore, even in BMMY and 2×YT, effective mediums for producing a single-chain antibody (scFv), the peptide of the invention expresses a specific adsorption ability. Therefore, when a single-chain antibody (scFv) is produced as the peptide of the invention, the single-chain antibody (scFv) can be directly separated and purified from a yeast secretion and a solution of crushed *Escherichia coli*.

Example 20

Production of Antibody Labeled with the Peptide of the Invention Composed of Amino Acid Sequence 2 of the Invention First, a peptide (KRIIIRRIRR; SEQ ID NO:33), which is the peptide of the invention composed of amino acid sequence 2 of the invention having lysine (K) at the N-terminal side, was synthesized by means of a solid phase method. Next, the peptide of the invention (0.5 mg) composed of amino acid sequence 2 of the invention was dissolved in 100 μl of a 25% glutaraldehyde solution and incubated at room temperature for 10 minutes. Then, diethylether (9 ml) and ethanol (1 ml) were added to precipitate the peptide of the invention labeled with glutaraldehyde and centrifugally recovered.

Furthermore, 0.5 mg of a mouse monoclonal antibody anti-human CRP antibody (#4715500 manufactured by Oriental Yeast Co., Ltd.) was dissolved in PBS (0.5 ml). To the PBS, the peptide of the invention labeled with glutaraldehyde was dissolved and incubated at 25° C. for one hour. Thereafter, 100 μl of 2M Tris-HCl (pH8.0) was added to terminate the reaction and subjected to ultrafiltration. In this manner, an anti-CRP antibody containing amino acid sequence 2 of the invention was purified as the peptide of the invention. Hereinafter, the anti-CRP antibody containing amino acid sequence 2 of the invention and produced in Example 20 will be referred to as "peptide 20 of the invention" and the original peptide thereof will be referred to as "original peptide 20".

Example 21

Production of a Single-Chain Antibody Having Amino Acid Sequence 2 of the Invention on the C-Terminal Side In this example, three types of single-chain antibodies (scFv) represented by Sequence ID Nos. 23, 24 and 25 of the sequence listing were used. To the C-terminal side of each of the antibodies, amino acid sequence 2 of the invention was introduced to prepare three types of single-chain antibodies. Note that, hereinafter, three types of single-chain antibodies (original peptides) represented by Sequence ID Nos. 23, 24 and 25 of the sequence listing will be respectively referred to as "original peptide 21-1", "original peptide 21-2" and "original peptide 21-3"; whereas three types of single-chain antibodies (the peptides of the invention) produced in this example by introducing amino acid sequence 2 of the invention to each of original peptide 21-1, original peptide 21-2 and original peptide 21-3 will be respectively referred to as "peptide 21-1 of the invention", "peptide 21-2 of the invention" and "peptide 21-3 of the invention". These single-chain antibodies each have an antigen-binding site causing a specific antigen-antibody reaction with C-reactive protein (CRP). In original peptides 21-1 to 21-3, the C terminal of the heavy-chain variable region ($V_H$) and the N terminal of the light-chain variable region ($V_L$) are connected by a chain-form linker peptide having a structure $(G_4S)_3$, which is a three-repeat of a 4-glycine (G)/serine (S) combination. Furthermore, in original peptides 21-1 to 21-3, a histidine tag is introduced in the C terminal of the light-chain variable region ($V_L$). Note that, the original peptides of Examples 22 and 23 each are a single-chain antibody (original peptide 21-1) represented by Sequence ID No. 23.

First, oligo DNA fragments of a sense chain (PStag-sense) and anti-sense chain (PStag-antisense) were synthesized, which contains a gene encoding amino acid sequence 2 of the invention whose 5' end was phosphorylated. After annealing, each of the oligo DNA fragments was introduced into pET22b(+) vector (manufactured by Novagen) digested with restriction enzymes NotI and XhoI to prepare pET-PStag vector (a vector having PStag introduced in pET22b(+)) containing a gene encoding amino acid sequence 2 of the invention. Note that, "PStag" refers to a gene expressing amino acid sequence 2 of the invention. The same definition will be applied below.

Next, a sense chain ($V_H$-sense) oligo DNA fragment containing a gene encoding a heavy-chain variable region ($V_H$) and an anti-sense chain ($V_L$-antisense) oligo DNA fragment containing a gene encoding a light-chain variable region ($V_L$) were synthesized. Using these synthesized oligo DNA fragments as primers, and three types of vectors pET-scFv (each vector is prepared by introducing a gene for scFv into pET22b (+)) expressing single-chain antibodies represented by Sequence ID Nos. 23, 24 and 25, used as templates, respectively, PCR was performed to amplify genes for three types of single-chain antibodies (scFv). The scFv genes amplified were digested with restriction enzymes NdeI and NotI and introduced into pET-PStag vector containing a gene encoding amino acid sequence 2 of the invention and digested with the same enzymes to prepare expression vectors (pET-scFv-PStag vector) for the three types of single-chain antibodies containing a gene encoding amino acid sequence 2 of the invention on the C-terminal side.

As a host, *Escherichia coli* (BL21(DE3) Rosetta (Novagen)) was used. The pET-scFv-PStag vector was introduced into a host to transform the host. The transformant was screened in an agar medium containing ampicillin. Thereafter, *Escherichia coli* was cultured in 2×YT medium (50 ml) and isopropyl 1-thio-galactoside (IPTG: isopropyl-1-thio-β-D(−)-galactoside) was added as an expression-inducting substance so as to obtain a final concentration of 1 mM to express a single-chain antibody (scFv-PStag) containing amino acid sequence 2 of the invention at the C terminal.

After the bacterial cells were crushed, an intracellular insoluble fraction was dissolved by a lysate containing 6M guanidine hydrochloride (denaturizing agent) and 10 mM mercapto ethanol (reducing agent). In this manner, an unpurified denatured single-chain antibody containing amino acid sequence 2 of the invention at the C terminal was obtained. Hereinafter, the single-chain antibodies of Example 21 of this state will be referred to as "unpurified denatured peptide 21-1 of the invention" to "unpurified denatured peptide 21-3 of the invention".

Furthermore, unpurified denatured peptides 21-1 to 21-3 of the invention while maintaining the denatured state were purified by Ni chelate affinity chromatography (IMAC) using HisTrap HP (GE HealthCare) to produce denatured single-chain antibodies containing amino acid sequence 2 of the invention on the C-terminal side. Hereinafter, the single-chain antibodies of Example 21 of this state will be referred to as "purified denatured peptide 21-1 of the invention" to purified denatured peptide 21-3 of the invention". The amino acid sequence of peptide 21-1 of the invention is represented by Sequence ID No. 26 of the sequence listing. The amino acid sequence of peptide 21-2 of the invention is represented by Sequence ID No. 27 of the sequence listing. The amino acid sequence of peptide 21-3 of the invention is represented by Sequence ID No. 28 of the sequence listing. Peptides 21-1 to 21-3 of the invention have amino acid sequence 2 of the invention on the C-terminal side of the light-chain variable region ($V_L$). To the site further closer to the C terminal than amino acid sequence 2 of the invention, a histidine tag is ligated. Note that, the amino acid sequences per se do not change before and after the purification and before and after denaturation, and are as shown in Sequence ID Nos. 26, 27 and 28.

Example 22

Production of a Single-Chain Antibody Having Amino Acid Sequence 2 of the Invention Between the Heavy-Chain Variable Region ($V_H$) and a Linker Peptide In this example, amino acid sequence 2 of the invention was introduced into a linker peptide connecting the heavy-chain variable region ($V_H$) and the light-chain variable region ($V_L$) of original peptide 21-1 (Sequence ID No. 23) and original peptide 21-2 (Sequence ID No. 24) to produce single-chain antibodies (hereinafter the peptides thus produced will be referred to as "peptide 22-1 of the invention" and "peptide 22-2 of the invention"). First, a sense chain ($V_H$-sense) oligo DNA fragment containing a gene encoding a heavy-chain variable region ($V_H$) and an anti-sense chain ($V_H$-antisense) oligo DNA fragment were synthesized. Using these synthesized oligo DNA fragments as primers, and pET-scFv vector expressing a single-chain antibody represented by Sequence ID No. 23 as a template, PCR was performed to amplify the gene for the heavy-chain variable region ($V_H$).

Next, a sense chain ($V_L$-sense) oligo DNA fragment containing a gene encoding a light-chain variable region ($V_L$) and an anti-sense chain ($V_L$-antisense) oligo DNA fragment were synthesized. A gene for the light-chain variable region ($V_L$) was amplified in the same manner as above.

Furthermore, the sense chain ($V_H$-PStag-$(G_4S)_3$-sense) oligo DNA fragment having a gene encoding the C terminal portion of the heavy-chain variable region ($V_H$), amino acid sequence 2 of the invention and a linker peptide in this order and an anti-sense chain (PStag-$(G_4S)_3$-$V_L$-antisense) oligo DNA having a gene encoding amino acid sequence 2 of the invention, a linker peptide and the N terminal portion of the light-chain variable region ($V_L$) in this order were synthesized.

Using the gene for the heavy-chain variable region ($V_H$), gene for the light-chain variable region ($V_L$), sense chain ($V_H$-PStag-$(G_4S)_3$-sense) oligo DNA fragment, anti-sense chain (PStag-$(G_4S)_3$-$V_L$-antisense) oligo DNA fragment, sense chain ($V_H$-sense) oligo DNA fragment and anti-sense chain ($V_L$-antisense) oligo DNA fragment, overlapping PCR was performed to prepare a gene (scFv-(PStag)) for the single-chain antibody having amino acid sequence 2 of the invention between the heavy-chain variable region ($V_H$) and the linker peptide $(G_4S)_3$. The gene was digested with restriction enzymes NdeI and NotI and introduced into pET22b(+) digested with the same enzymes to prepare an expression vector (pET-scFv-(PStag) vector) for the single-chain antibody containing the gene encoding amino acid sequence 2 of the invention in the linker peptide $(G_4S)_3$. Note that, "(PStag)" means that PStag is introduced in the middle of the single-chain antibody, more specifically, between the heavy-chain variable region ($V_H$) and the linker peptide $(G_4S)_3$. The same will be applied below.

Thereafter, in the same manner as in Example 21, the pET-scFv-(PStag) vector was introduced into a host and cultured. After bacterial cells were crushed, an intracellular insoluble fraction was dissolved by a lysate containing 6M guanidine hydrochloride (denaturizing agent) and 10 mM mercapto ethanol (reducing agent) to obtain a single-chain antibody having amino acid sequence 2 of the invention in the unpurified denatured linker peptide $(G_4S)_3$. Furthermore, purification was made in the same manner as in Example 21 to produce purified denatured peptide 22-1 of the invention (hereinafter referred to as "purified denatured peptide 22-1 of the invention"). The amino acid sequence of peptide 22-1 of the invention is represented by Sequence ID No. 29 of the sequence listing. Peptide 22-1 of the invention has amino acid sequence 2 of the invention arranged between the domain of the heavy-chain variable region ($V_H$) and the linker peptide $(G_4S)_3$.

Furthermore, in the same manner, purified denatured peptide 22-2 of the invention was produced which has amino acid sequence 2 of the invention between the domain for the heavy-chain variable region ($V_H$) of original peptide 21-2 (Sequence ID No. 24) and the linker peptide $(G_4S)_3$. The amino acid sequence of peptide 22-2 of the invention is represented by Sequence ID No. 30 of the sequence listing.

Example 23

Production of a Single-Chain Antibody Having Amino Acid Sequence 2 of the Invention Both at the C Terminal and Between the Heavy-Chain Variable Region ($V_H$) and a Linker Peptide In this example, amino acid sequence 2 of the invention was introduced into both at the C-terminal side (more specifically, the C-terminal side of the light-chain variable region ($V_L$)) and between the heavy-chain variable region ($V_H$) and the linker peptide (more specifically, the C terminal of the heavy-chain variable region ($V_H$) side) of a single-chain antibody of original peptide 21-1 and original peptide 21-2 to produce single-chain antibodies (hereinafter, the peptides thus produced will be referred respectively to as "peptide 23-1 of the invention" and "peptide 23-2 of the invention"). First, in the same manner as in Example 22, a gene (scFv-(PStag)) for the single-chain antibody having amino acid sequence 2 of the invention between the heavy-chain variable region ($V_H$) and the linker peptide $(G_4S)_3$ was prepared. The gene was introduced into pET22b(+) in Example 22; however, in this example, the gene was introduced into the pET-PStag vector used in Example 21 to prepare an expression vector (pET-scFv-(PStag)-PStag vector) for a single-chain antibody containing a gene encoding amino acid sequence 2 of the invention both at the C-terminal side and between the heavy-chain variable region ($V_H$) and the linker peptide $(G_4S)_3$.

Thereafter, in the same manner as in Example 21, the pET-scFv-(PStag)-PStag vector was introduced into a host and cultured. After bacterial cells were crushed, an intracellular insoluble fraction was dissolved by a lysate containing 6M guanidine hydrochloride (denaturizing agent) and 10 mM mercapto ethanol (reducing agent). An unpurified denatured single-chain antibody (scFv) having amino acid sequence 2 of the invention both at the C-terminal side and in the linker peptide was obtained. Furthermore, in the same manner as in Example 21, purification was made to produce a purified denatured peptide 23-1 of the invention (hereinafter referred to as "purified denatured peptide 23-1 of the invention"). The amino acid sequence of peptide 23-1 of the invention is represented by Sequence ID No. 31 of the sequence listing. Peptide 23-1 of the invention has amino acid sequence 2 of the invention on the C-terminal side of the light-chain variable region ($V_L$) similarly to peptide 21-1 of the invention. Furthermore, a histidine tag is ligated on the C-terminal side of amino acid sequence 2 of the invention. Furthermore, similarly to peptide 22-1 of the invention, an amino acid sequence 2 of the invention is present between the heavy-chain variable region ($V_H$) domain and the linker peptide $(G_4S)_3$.

Furthermore, in the same approach, purified denatured peptide 23-2 of the invention was produced in which amino acid sequence 2 of the invention is arranged at the C-terminal side of the light-chain variable region ($V_L$) of original peptide 21-2 (Sequence ID No. 24) and between the heavy-chain variable region ($V_H$) domain and the linker peptide $(G_4S)_3$. The amino acid sequence of peptide 23-2 of the invention is represented by Sequence ID No. 32 of the sequence listing.

Example 24

Evaluation on the Activity-Values of Peptides 21-1 to 21-3 of the Invention Immobilized In this example, to evaluate the activity values of peptides 21-1 to 21-3 of the invention (Sequence ID Nos. 26 to 28) immobilized, purified denatured peptides 21-1 to 21-3 of the invention were refolded in a liquid phase, allowed to bind to a hydrophilic polystyrene surface and measured for the activity value of an antigen-antibody reaction. For comparison, original peptides 21-1 to 21-3 (Sequence ID Nos. 23 to 25), peptide 20 of the invention, which is not a single-chain antibody but an antibody molecule, and original peptide 20 were also allowed to bind to a hydrophilic polystyrene surface and measured for the activity value. Furthermore, for comparison with a conventional peptide, original peptide 20 (antibody molecule) was allowed to bind to a hydrophobic polystyrene surface and measured for the activity value.

First, purified denatured peptides 21-1 to 21-3 of the invention (Sequence ID Nos. 26 to 28) were diluted in PBS containing 375 μM oxidized-form glutathione (GSSG) so as to contain 80 mM urea serving as a denaturing agent and incubated at room temperature, three hours to perform refolding. After centrifugally removing aggregates, purification was performed by Ni chelate affinity chromatography (IMAC) using HisTrap HP (GE HealthCare) and dialysis against PBS was performed to produce three types of soluble peptides 21-1 to 21-3 of the invention.

Next, peptides 21-1 to 21-3 of the invention were diluted with 0.1PBST to a concentration of 5 μg/ml. The dilution solution (100 μl) was placed in a hydrophilic polystyrene plate ("IWAKI microplate #3860-096" manufactured by AGC Techno Glass Co., Ltd.) and incubated at room temperature for two hours to immobilize the peptide of the invention. After washed six times with 0.1PBST, unbound sites on the polystyrene plate surface were blocked with 0.1PBST (blocking reagent) containing 2% BSA. Further after washed six times with 0.1PBST, 100 μl of biotin-CRP (antigen) diluted with 0.1PBST containing 0.2% BSA to 1 to 5000 ng/ml was added and incubated at room temperature for one hour to perform an antigen-antibody reaction with the peptide of the invention. Further after washed six times with 0.1PBST, 100 μl of HRP-labeled streptavidin diluted with 0.1PBST containing 0.2% BSA to 5000 fold was added and incubated at room temperature for 30 minutes. After washed six times with 0.1PBST, a chromogenic substrate was added and allowed to develop color for 30 minutes. Thirty minutes later, using a microplate reader ("SUNRISE Remote" manufactured by TECAN), absorbance at 405 nm was measured. The same treatment was applied to single-chain antibodies, which are original peptides 21-1 to 21-3 represented by Sequence ID Nos. 23 to 25, peptide 20 of the invention labeled with amino acid sequence 2 of the invention as described in Example 20 and original peptide 20, and measured for absorbance. Furthermore, 5 μg/ml original peptide 20 was immobilized in PBS to a hydrophobic polystyrene plate ("BD Falcon microplate #351172" manufactured by Becton, Dickinson and Company) and measured for absorbance.

Figure 13:
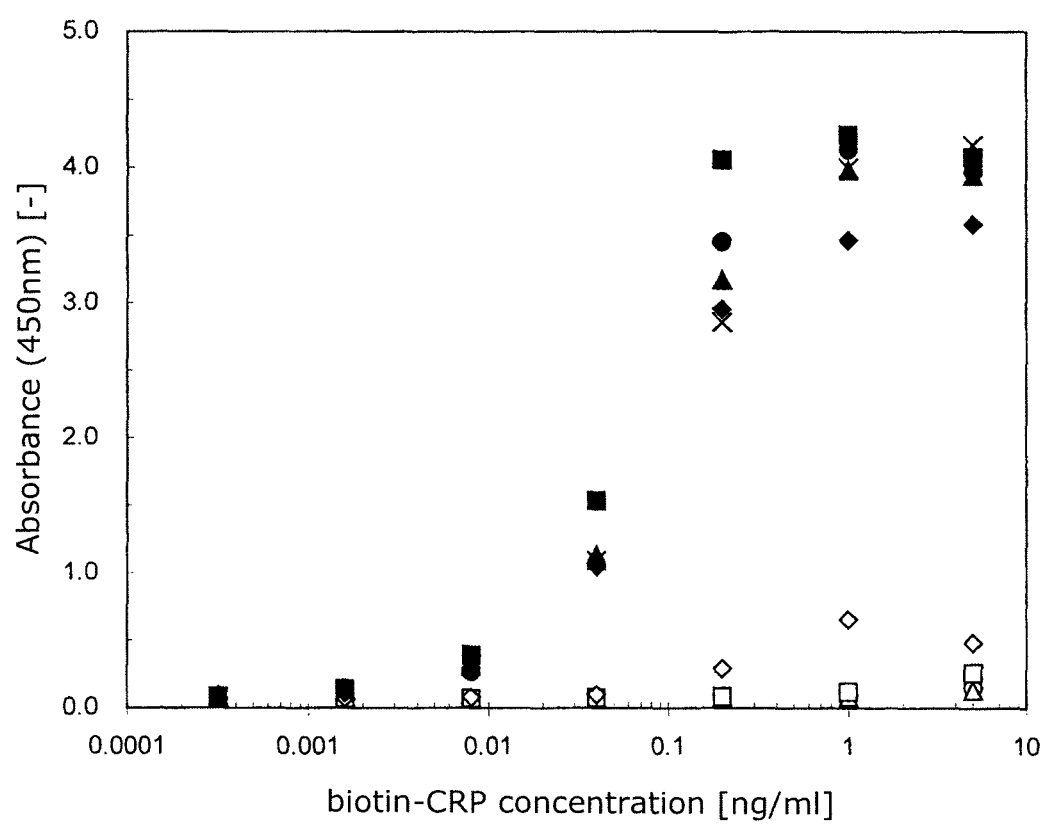
FIG. 13 is a graph showing the activity value when the amino acid sequence of the invention is introduced into a single-chain antibody.

FIG. 13 shows the measurement results of Example 24. In FIG. 13, a solid circle (●), a solid triangle and a solid square respectively indicate the results of peptides 21-1, 21-2 and 21-3 of the invention represented by Sequence ID Nos. 26, 27 and 28. An open circle (○), an open triangle (Δ) and an open square (□) respectively indicate the results of original peptides 21-1, 21-2 and 21-3 represented by Sequence ID Nos. 23, 24 and 25. Furthermore, a solid lozenge (♦) indicates the result of peptide 20 of the invention and an open lozenge (◇) indicates the result of original peptide 20, i.e., a mouse monoclonal antibody anti-human CRP antibody (#4715500 manufactured by Oriental Yeast Co., Ltd.). Mark (×) indicates the experimental result of original peptide 20 immobilized to a hydrophobic polystyrene plate. In FIG. 11, the vertical axis indicates absorbance (405 nm) and the transverse axis indicates the concentration (ng/ml) of biotin-CRP.

From FIG. 13, it can be confirmed that original peptides 21-1, 21-2, 21-3 (○, Δ, □) and original peptide 20 (◇) are not virtually activated on the hydrophilic polystyrene surface; however, peptides 21-1, 21-2, 21-3 of the invention (solid circle, solid triangle, solid square) all maintain a high antigen binding activity regardless of difference in amino acid sequence of a single-chain antibody. Furthermore, it is found that peptide 20 of the invention (♦) labeled with amino acid sequence 2 of the invention is selectively immobilized onto a hydrophilic polystyrene plate and exhibits a high antigen binding activity. Even compared to the result (×) of the mouse monoclonal antibody (original peptide 20) immobilized onto a hydrophobic polystyrene plate, which is conventionally used in ELISA, peptide 20, 21-1, 21-2 and 21-3 of the invention having amino acid sequence 2 of the invention, have high signals which are equal to or more than the aforementioned one. From the above results, it was confirmed that peptides 21-1, 21-2, 21-3 of the invention, which are constructed by introducing amino acid sequence 2 of the invention to the C terminal side of various types of single-chain antibodies, can be immobilized to a hydrophilic polystyrene plate while maintaining a high antigen binding activity. It was also confirmed that a monoclonal antibody, which is labeled with amino acid sequence 2 of the invention, can be immobilized to a hydrophilic polystyrene plate while maintaining a high antigen binding activity.

Example 25

Evaluation on Refolding and Activity Value of Purified Denatured Peptides 21-1, 22-1 and 23-1 of the Invention Immobilized on a Solid Phase In this example, to evaluate refolding and activity value of purified denatured peptides 21-1, 22-1 and 23-1 of the invention immobilized, these peptides were allowed to bind to a hydrophilic polystyrene surface and measured for the activity value of an antigen-antibody reaction.

First, purified denatured peptide 21-1 of the invention (Sequence ID No. 26), 22-1 (Sequence ID No. 29) and 23-1 (Sequence ID No. 31) were each prepared so as to obtain a final concentration of urea serving as a denaturizing agent of 4M to prepare samples. Next, each sample (20 μl) was placed in a hydrophilic polystyrene plate ("IWAKI microplate #3860-096" manufactured by AGC Techno Glass Co., Ltd.), stirred by a mixer and thereafter incubated at room temperature for one hour to immobilize the peptides of the invention (weight of scFv per well: 0.5 μg/well). After washed six times with 0.1PBST, unbound sites on the polystyrene plate surface was blocked with 0.1PBST (blocking reagent) containing 2% BSA. Further after washed six times with 0.1PBST, 100 μl of biotin-CRP (antigen) diluted with 0.1PBST containing 0.2% BSA to 1 to 5000 ng/ml was added and incubated at room temperature for one hour to perform an antigen-antibody reaction of the peptide of the invention. Furthermore, after washed six times with 0.1PBST, HRP-labeled streptavidin (100 μl) diluted with 0.1PBST containing 0.2% BSA to 5000 fold was added and incubated at room temperature for 30 minutes. After washed six times with 0.1PBST, a chromogenic substrate was added and allowed to develop color for 30 minutes. Thirty minutes later, using a microplate reader ("SUNRISE Remote" manufactured by TECAN), absorbance at 405 nm was measured. The same treatment was applied to original peptide 21-1 (Sequence ID No. 23) and absorbance was measured.

Figure 14:
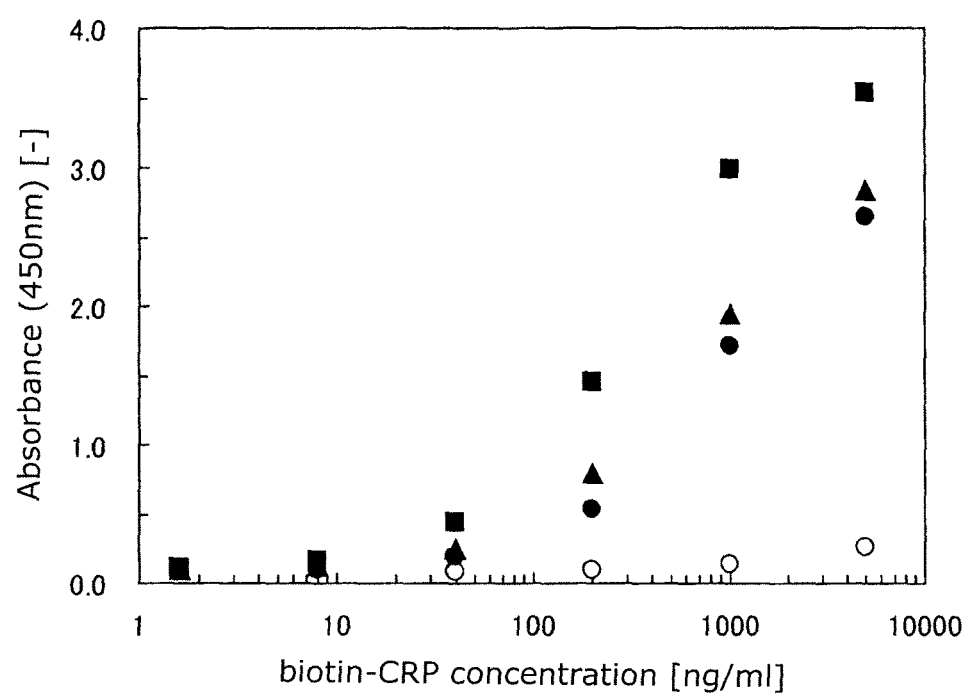
FIG. 14 is a graph showing the relationship between the activity value and an amino acid sequence of the invention introduction site in a single-chain antibody.

FIG. 14 shows the measurement results of Example 25. In FIG. 14, a solid circle (●) indicates the result of purified denatured peptide 21-1 of the invention; a solid triangle indicates the result of purified denatured peptide 22-1 of the invention; a solid square indicates the result of purified denatured peptide 23-1 of the invention; and an open circle (○) is the result of original peptide 21-1. In FIG. 14, the vertical axis indicates absorbance (405 nm) and the transverse axis indicates the concentration of biotin-CRP (ng/ml).

From FIG. 14, it can be confirmed that a single-chain antibody (○) serving as original peptide 21-1 is not virtually activated; however, purified denatured peptides 21-1, 22-1 and 23-1 of the invention are all activated. In short, by virtue of use of the amino acid sequence of the invention, denatured peptides 21-1, 22-1 and 23-1 of the invention are immobilized by bringing them into contact with a solid phase and simultaneously refolded, thereby reconstructing denatured proteins to be normal.

Furthermore, it was confirmed that peptide 21-1 of the invention having amino acid sequence 2 of the invention introduced into the C-terminal side and peptide 22-1 of the invention having amino acid sequence 2 of the invention introduced into the site between the heavy-chain variable region and the linker peptide have almost the same activity; whereas a higher activity can be obtained in peptide 23-1 of the invention having amino acid sequence 2 of the invention introduced into both the C-terminal side and the site between the heavy-chain variable region and the linker peptide.

Example 26

Evaluation on Solid-Phase Refolding and Activity Value of Purified Denatured Peptides 21-2, 22-2 and 23-2 of the Invention Immobilized on a Solid Phase In this example, to evaluate refolding and activity value of purified denatured peptides 21-2, 22-2 and 23-2 of the invention, these peptides were allowed to bind to a hydrophilic polystyrene surface and measured for activity value of an antigen-antibody reaction. Note that, the basic operation of this example was the same as in Example 25; however, the conditions were more or less modified. Just for confirmation, the operation will be described.

First, solutions were prepared by using PBS containing 1% Tween 20 such that a denaturizing agent, urea, is contained in a final concentration of 4M and purified denatured peptides 21-2 of the invention (Sequence ID No. 27), 22-2 (Sequence ID No. 30) and 23-2 (Sequence ID No. 32) were each contained in a concentration of 10 μg/ml to prepare samples. Next, each sample (100 μl) was placed in a hydrophilic polystyrene plate ("IWAKI microplate #3860-096" manufactured by AGC Techno Glass Co., Ltd.) stirred by a mixer and incubated at room temperature for three hours to immobilize the peptide of the invention. After washed six times with 0.1PBST, 300 μl of 0.1PBST (blocking reagent) containing 2% BSA was added and incubated at room temperature for one hour to block unbound sites on the polystyrene plate surface. Furthermore, after washed six times with 0.1PBST, 100 μl of biotin-CRP (antigen) diluted with 0.1PBST containing 0.2% BSA to 1 to 5000 ng/ml was added and incubated at room temperature for one hour to perform an antigen-antibody reaction with the peptide of the invention. Furthermore, after washed six times with 0.1PBST, 100 μl of HRP-labeled streptavidin diluted with 0.1PBST containing 0.2% BSA to 5000 fold was added and incubated at room temperature for one hour. Furthermore, after washed six times with 0.1PBST, a chromogenic substrate (100 μl) was added and allowed to develop color for 30 minutes. Thirty minutes later, using a microplate reader ("SUNRISE Remote" manufactured by TECAN), absorbance at 405 nm was measured. The same treatment was applied to original peptide 21-2 (Sequence ID No. 24) and absorbance was measured.

Figure 15:
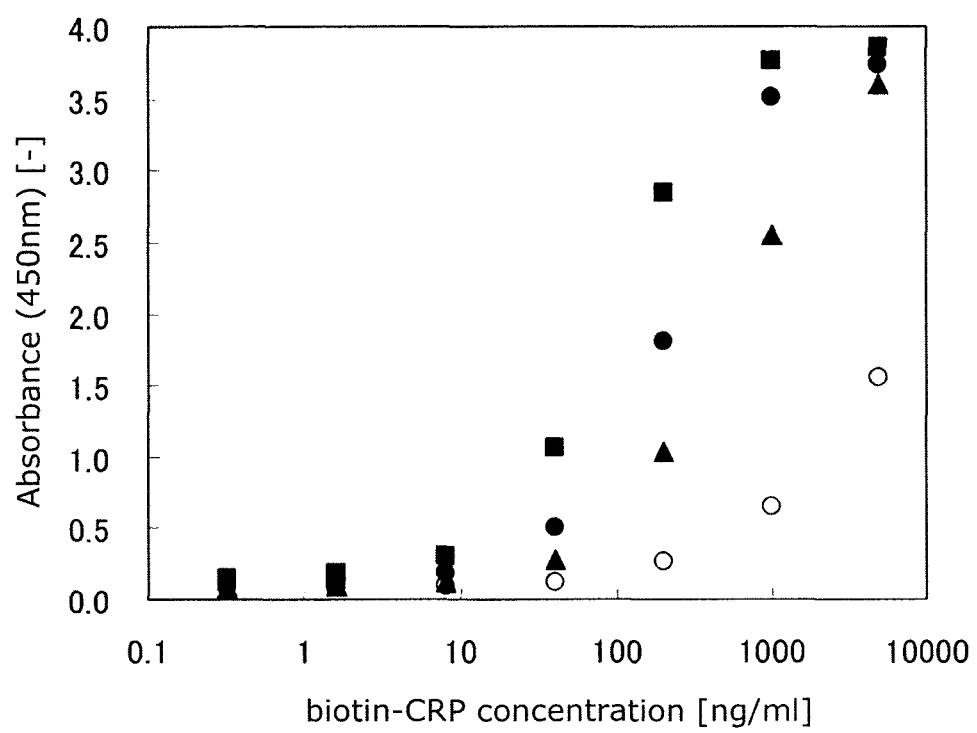
FIG. 15 is a graph showing the relationship between the activity value and an amino acid sequence of the invention introduction site in a single-chain antibody.

FIG. 15 shows the measurement results of Example 26. In FIG. 15, a solid circle (●) indicates the result of purified denatured peptide 21-2 of the invention; a solid triangle indicates the result of purified denatured peptide 22-2 of the invention; a solid square indicates the result of purified denatured peptide 23-2 of the invention; and open circle (○) indicates of the result of original peptide 21-2. In FIG. 15, the vertical axis indicates absorbance (405 nm) and the transverse axis is the concentration (ng/ml) of biotin-CRP.

From FIG. 15, it can be confirmed that original peptide 21-2, i.e., a single-chain antibody (○) is not virtually activated; however, purified denatured peptide 21-2, 22-2 and 23-2 of the invention are all activated. More specifically, it was confirmed that similarly to Example 25, also in this example, by virtue of use of the amino acid sequence of the invention, denatured peptides 21-2, 22-2 and 23-2 of the invention are immobilized by bringing them into contact with a solid phase, and simultaneously refolded, thereby reconstructing denatured proteins to be normal.

Furthermore, it can be confirmed that peptide 21-2 of the invention having amino acid sequence 2 of the invention introduced into the C-terminal side exhibits a higher activity than peptide 22-2 of the invention having amino acid sequence 2 of the invention introduced into the site between the heavy-chain variable region and the linker peptide. However, it was also confirmed that a higher activity than that of peptide 21-2 can be obtained by peptide 23-2 of the invention having amino acid sequence 2 of the invention introduced into both the C-terminal side and the site between the heavy-chain variable region and the linker peptide.

Example 27

Evaluation of Binding Ability and Activity Value of Purified Denatured Peptide 21-1 of the Invention to a Solid Phase In this example, the relationship between the amount of purified denatured peptide 21-1 of the invention (Sequence ID No. 26), binding ability to a hydrophilic polystyrene surface and activity value was evaluated.

First, samples were prepared so as to contain purified denatured peptide 21-1 of the invention in a concentration of 3.2 μg/ml, 32 μg/ml and 320 μg/ml with 8M urea. Next, each sample (10 μl) was placed in a hydrophilic polystyrene plate ("IWAKI microplate #3860-096" manufactured by AGC Techno Glass Co., Ltd.). To each well, 0.1PBST (90 μl) was added, diluted to 10 fold and incubated at 4° C. overnight to immobilize peptide 21-1 of the invention. After washed six times with 0.1PBST, unbound sites on the polystyrene plate surface were blocked with 0.1PBST (blocking reagent) containing 2% BSA. Furthermore, after washed six times with 0.1PBST, 100 μl of biotin-CRP (antigen) diluted with 0.1PBST containing 0.2% BSA to 1 to 5000 ng/ml was added and incubated at room temperature for one hour to perform an antigen-antibody reaction with the peptide of the invention. Furthermore, after washed six times with 0.1PBST, HRP labeled streptavidin (100 μl) diluted with 0.1PBST containing 0.2% BSA to 1000 fold was added and incubated at room temperature for 30 minutes. After washed six times with 0.1PBST, a chromogenic substrate was added and allowed to develop color for 30 minutes. Thirty minutes later, using a microplate reader ("SUNRISE Remote" manufactured by TECAN), absorbance at 405 nm was measured.

Figure 16:
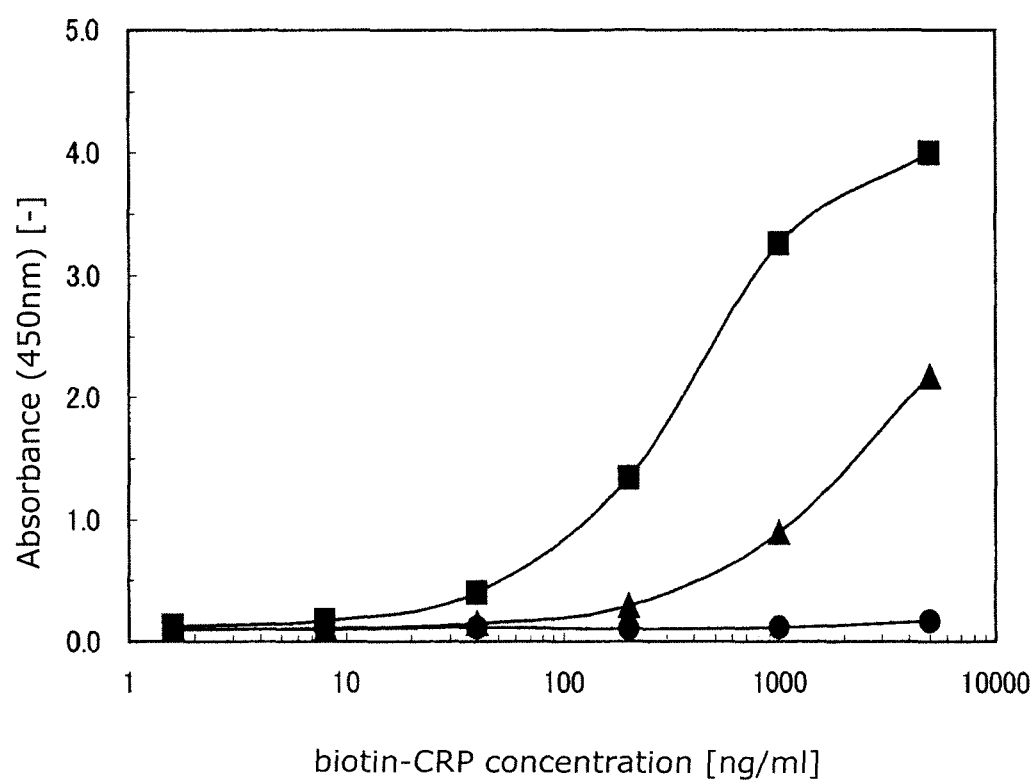
FIG. 16 is a graph showing the relationship between the amount of single-chain antibody and the activity value to a hydrophilic polystyrene substrate.

FIG. 16 shows the measurement results of Example 27. In FIG. 16, a solid circle (●) indicates the result of the case where the amount of purified denatured peptide 21-1 of the invention per well is 0.032 μg; a solid triangle indicates the result of the case of 0.32 μg; and a solid square indicates the result of the case of 3.2 μg. In FIG. 16, the vertical axis indicates absorbance (405 nm) and the transverse axis indicates the concentration (ng/ml) of biotin-CRP.

From FIG. 16, it can be confirmed that purified denatured peptide 21-1 of the invention is activated on a hydrophilic polystyrene surface. More specifically, by virtue of the use of the amino acid sequence of the invention, the peptide 21-1 of the invention exhibits a specific binding ability to a hydrophilic polystyrene substrate to immobilize and simultaneously refolded, thereby reconstructing the natured protein to be normal.

Example 28

Evaluation on Separation/Purification by Immobilization and Activity Value of Unpurified Denatured Peptides 21-1 to 21-3 of the Invention In this example, unpurified denatured peptides 21-1 to 21-3 of the invention (Sequence ID Nos. 26, 27, 28) were evaluated on the possibility of separation/purification by immobilizing them to a hydrophilic polystyrene surface and activity values of the peptides in the immobilized state.

First, unpurified denatured peptides 21-1 to 21-3 of the invention and 3.2 mg/ml purified denatured peptide 21-1 of the invention were diluted with 0.1PBST 10 fold and 100 fold to prepare samples. The samples (200 μl) were placed in a hydrophilic polystyrene plate ("IWAKI microplate #3860-096" manufactured by AGC Techno Glass Co., Ltd.) and incubated at 4° C. overnight to immobilize the peptide of the invention. After washed six times with 0.1PBST, unbound sites on the polystyrene plate surface were blocked with 0.1PBST (blocking reagent) containing 2% BSA. Furthermore, after washed six times with 0.1PBST, 100 μl of biotin-CRP (antigen) diluted with 0.1PBST containing 0.2% BSA to 1 to 5000 ng/ml was added and incubated at room temperature for one hour to perform an antigen-antibody reaction with the peptide of the invention. Furthermore, after washed six times with 0.1PBST, 100 μl of HRP labeled streptavidin diluted with 0.1PBST containing 0.2% BSA to 1000 fold was added and incubated at room temperature for 30 minutes. After washed six times with 0.1PBST, a chromogenic substrate was added and allowed to develop color for 30 minutes. Thirty minutes later, using a microplate reader ("SUNRISE Remote" manufactured by TECAN), absorbance at 405 nm was measured.

FIG. 17(a) shows measurement results of the case of 10-fold dilution; FIG. 17(b) shows measurement results of the case of 100-fold. In FIGS. 17(a) and (b), a solid circle (●) indicates the result of unpurified denatured peptide 21-1 of the invention; a solid triangle indicates the result of unpurified denatured peptide 21-2 of the invention; a solid square indicates the result of unpurified denatured peptide 21-3 of the invention; and an open circle (○) indicates the result of purified denatured peptide 21-1 of the invention. In FIGS. 17(a) and (b), the vertical axis indicates absorbance (405 nm) and the transverse axis indicates the concentration (ng/ml) of biotin-CRP.

Figure 17:
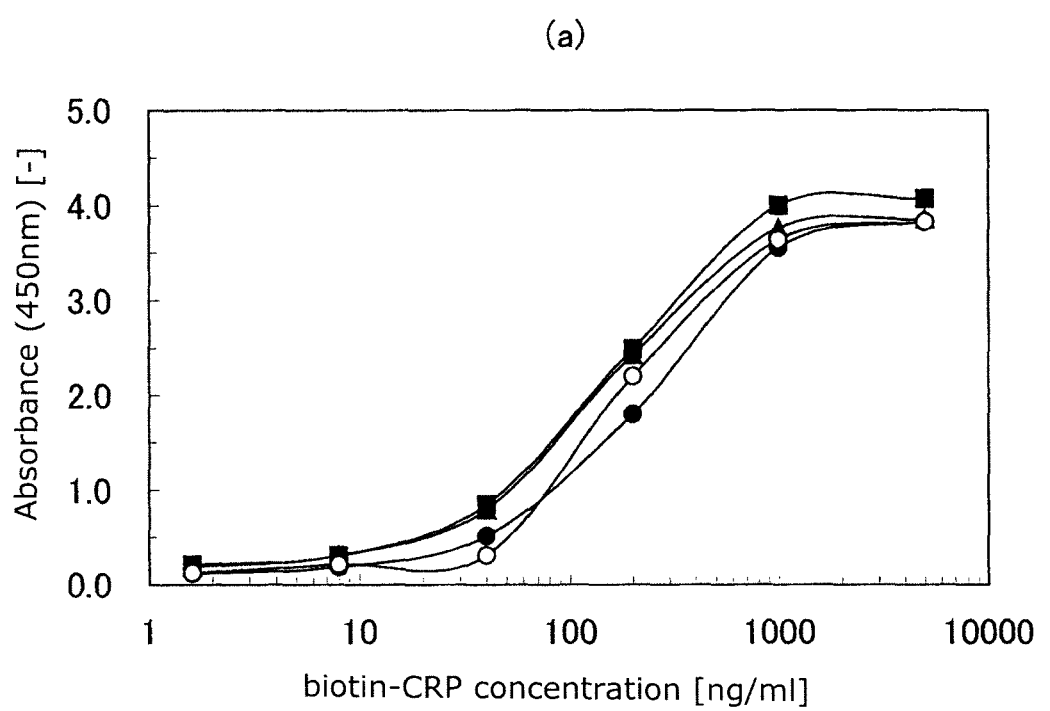
FIG. 17 is a graph showing the activity value and the binding ability of the peptide of the invention in an unpurified denatured state to a polystyrene substrate.
Figure 17:
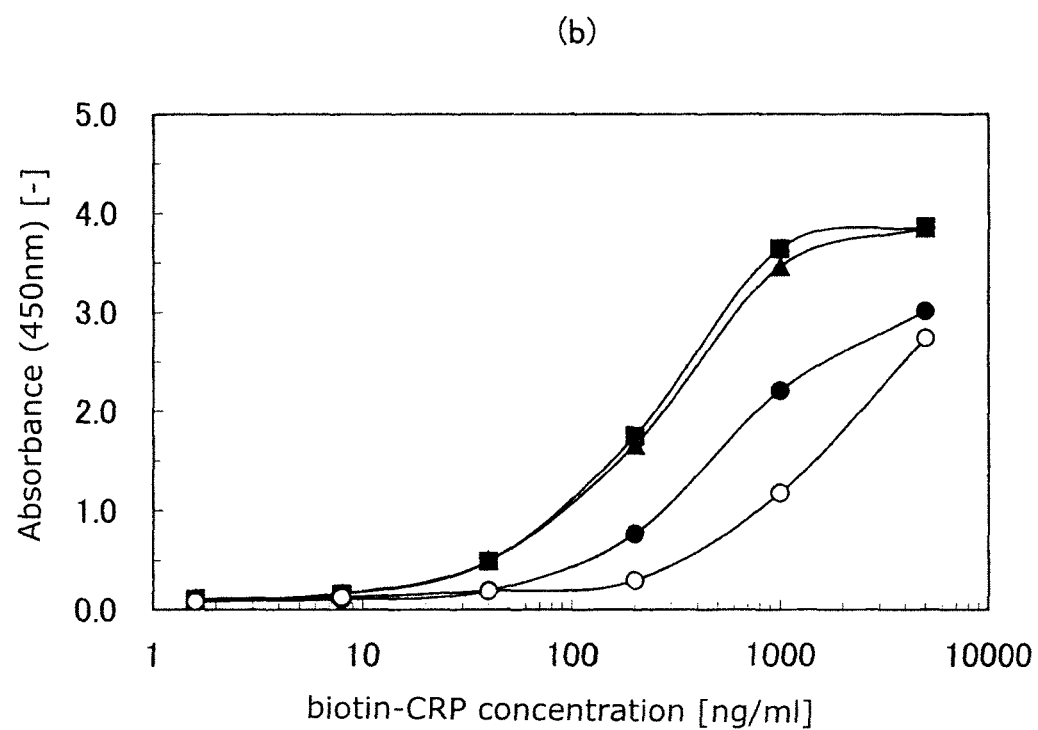

From FIG. 17, it can be confirmed that even in an unpurified state, immobilization was made to a hydrophilic polystyrene surface and activation is made. More specifically, by virtue of the use of the amino acid sequence of the invention, the peptide of the invention can specifically bind to a hydrophilic polystyrene plate and therefore, can be used in separation/purification step of a production process. In addition, it was conformed that since the peptide of the invention is activated, refolding has been made. Sequence listing free text Sequence ID No. 1: Peptide having specific affinity for a surface of a hydrophilic solid substance.

Sequence ID No. 2: Peptide having specific affinity for a surface of a hydrophilic solid substance.

Sequence ID No. 3: Peptide having specific affinity for a surface of a hydrophilic solid substance.

Sequence ID No. 4: Peptide having specific affinity for a surface of a hydrophilic solid substance.

Sequence ID No. 5: Peptide having specific affinity for a surface of a hydrophilic solid substance.

Sequence ID No. 6: Peptide having specific affinity for a surface of a hydrophilic solid substance.

Sequence ID No. 7: Peptide having specific affinity for a surface of a hydrophilic solid substance.

Sequence ID No. 8: Peptide having specific affinity for a surface of a hydrophilic solid substance.

Sequence ID No. 9: Peptide having specific affinity for a surface of a hydrophilic solid substance.

Sequence ID No. 10: Peptide having specific affinity for a surface of a hydrophilic solid substance.

Sequence ID No. 11: Peptide having specific affinity for a surface of a hydrophilic solid substance.
Sequence ID No. 12: Peptide having specific affinity for a surface of a hydrophilic solid substance.
Sequence ID No. 13: Peptide having specific affinity for a surface of a hydrophilic solid substance.
Sequence ID No. 14: Peptide having specific affinity for a surface of a hydrophilic solid substance.
Sequence ID No. 15: Peptide having specific affinity for a surface of a hydrophilic solid substance.
Sequence ID No. 16: Peptide having specific affinity for a surface of a hydrophilic solid substance.
Sequence ID No. 17: Peptide having specific affinity for a surface of a hydrophilic solid substance.
Sequence ID No. 18: Peptide having specific affinity for a surface of a hydrophilic solid substance.
Sequence ID No. 19: Peptide having specific affinity for a surface of a hydrophilic solid substance.
Sequence ID No. 20: Peptide having specific affinity for a surface of a hydrophilic solid substance.
Sequence ID No. 21: Synthesized DNA.
Sequence ID No. 22: Synthesized DNA.
Sequence ID No. 23: Single-chain antibody.
Sequence ID No. 24: Single-chain antibody.
Sequence ID No. 25: Single-chain antibody.
Sequence ID No. 26: Single-chain antibody having specific affinity for a hydrophilic solid substance surface.
Sequence ID No. 27: Single-chain antibody having specific affinity for a hydrophilic solid substance surface.
Sequence ID No. 28: Single-chain antibody having specific affinity for a hydrophilic solid substance surface.
Sequence ID No. 29: Single-chain antibody having specific affinity for a hydrophilic solid substance surface.
Sequence ID No. 30: Single-chain antibody having specific affinity for a hydrophilic solid substance surface.
Sequence ID No. 31: Single-chain antibody having specific affinity for a hydrophilic solid substance surface.
Sequence ID No. 32: Single-chain antibody having specific affinity for a hydrophilic solid substance surface.

The invention claimed is:

1. A peptide, having an N-terminal and a C-terminal, said peptide comprising a first peptide region located N-terminal to a second peptide region, wherein said first peptide region is a heavy chain variable region of an antigen-binding site or a light chain variable region of an antigen-binding site, and said second peptide region has the sequence:
   1) RIIIRRIRR (SEQ ID NO:2);
   2) RAIARRIRR (SEQ ID NO:3);
   3) RLLLRRLRR (SEQ ID NO:4);
   4) RVVVRRVRR (SEQ ID NO:5);
   5) RAAARRARR (SEQ ID NO:6);
   6) RGGGRRGRR (SEQ ID NO:7);
   7) RMMMRRMRR (SEQ ID NO:8);
   8) RSSSRRSRR (SEQ ID NO:9); or
   9) RTTTRRTRR (SEQ ID NO:10),
   wherein R is arginine, I is isoleucine, L is leucine, V is valine, A is alanine, G is glycine, M is methionine, S is serine and T is threonine.

2. The peptide according to claim 1, wherein said peptide is a peptide of an antigen-binding molecule having an antigen-binding site that comprises a heavy chain variable region and a light chain variable region.

3. The peptide according to claim 1, characterized in that said second peptide region is capable of specific adsorption to a hydrophilic resin solid surface.

4. The peptide according to claim 3, characterized in that the hydrophilic resin solid surface is a hydrophilic polystyrene surface.

5. The peptide according to claim 2, characterized by being a single-chain antibody (scFv), a multivalent single-chain antibody (sc(Fv)$_n$), a single-chain antibody fused with a constant region (scFv-Fc), a Fab fragment or an F(ab')$_2$ fragment, wherein one or both of said heavy and light chain variable regions is located N-terminal to said second peptide region.

6. The peptide according to claim 2, characterized by having a linker peptide binding the heavy-chain variable region and the light-chain variable region, wherein said second peptide region is either C-terminal to said linker peptide, N-terminal to said linker peptide, or within said linker peptide.

7. The peptide of claim 1, wherein said second peptide region is bound to a solid support, thereby immobilizing said antigen-binding molecule to said solid support while permitting said antigen-binding site to bind to antigen.

8. The peptide according to claim 7, characterized in that the solid support has a hydrophilic resin surface.

9. The peptide according to claim 7, characterized in that the solid support has a hydrophilic polystyrene surface.

10. The peptide according to claim 7, characterized in that the immobilized antigen-binding molecule, by being able to bind antigen is suitable for use in an immunoassay.

* * * * *

```
                            SEQUENCE LISTING

<160> NUMBER OF SEQ ID NOS: 33

<210> SEQ ID NO 1
<211> LENGTH: 9
<212> TYPE: PRT
<213> ORGANISM: Artificial Sequence
<220> FEATURE:
<223> OTHER INFORMATION: peptide having a specific affinity for a
      hydrophilic solid surface
<220> FEATURE:
<221> NAME/KEY: variation
<222> LOCATION: 2
<223> OTHER INFORMATION: Xaa= Ile, Leu, Val, Ala, Gly, Met, Ser or Thr
<220> FEATURE:
<221> NAME/KEY: variation
<222> LOCATION: 3
<223> OTHER INFORMATION: Xaa= Ile, Leu, Val, Ala, Gly, Met, Ser or Thr
<220> FEATURE:
<221> NAME/KEY: variation
<222> LOCATION: 4
<223> OTHER INFORMATION: Xaa= Ile, Leu, Val, Ala, Gly, Met, Ser or Thr
<220> FEATURE:
<221> NAME/KEY: variation
<222> LOCATION: 7
<223> OTHER INFORMATION: Xaa= Ile, Leu, Val, Ala, Gly, Met, Ser or Thr

<400> SEQUENCE: 1

Arg Xaa Xaa Xaa Arg Arg Xaa Arg Arg
 1               5

<210> SEQ ID NO 2
<211> LENGTH: 9
<212> TYPE: PRT
<213> ORGANISM: Artificial Sequence
<220> FEATURE:
<223> OTHER INFORMATION: peptide having a specific affinity for a
      hydrophilic solid surface

<400> SEQUENCE: 2

Arg Ile Ile Ile Arg Arg Ile Arg Arg
 1               5

<210> SEQ ID NO 3
<211> LENGTH: 9
<212> TYPE: PRT
<213> ORGANISM: Artificial Sequence
<220> FEATURE:
```

```
<223> OTHER INFORMATION: peptide having a specific affinity for a
      hydrophilic solid surface

<400> SEQUENCE: 3

Arg Ala Ile Ala Arg Arg Ile Arg Arg
 1               5

<210> SEQ ID NO 4
<211> LENGTH: 9
<212> TYPE: PRT
<213> ORGANISM: Artificial Sequence
<220> FEATURE:
<223> OTHER INFORMATION: peptide having a specific affinity for a
      hydrophilic solid surface

<400> SEQUENCE: 4

Arg Leu Leu Leu Arg Arg Leu Arg Arg
 1               5

<210> SEQ ID NO 5
<211> LENGTH: 9
<212> TYPE: PRT
<213> ORGANISM: Artificial Sequence
<220> FEATURE:
<223> OTHER INFORMATION: peptide having a specific affinity for a
      hydrophilic solid surface

<400> SEQUENCE: 5

Arg Val Val Val Arg Arg Val Arg Arg
 1               5

<210> SEQ ID NO 6
<211> LENGTH: 9
<212> TYPE: PRT
<213> ORGANISM: Artificial Sequence
<220> FEATURE:
<223> OTHER INFORMATION: peptide having a specific affinity for a
      hydrophilic solid surface

<400> SEQUENCE: 6

Arg Ala Ala Ala Arg Arg Ala Arg Arg
 1               5

<210> SEQ ID NO 7
<211> LENGTH: 9
<212> TYPE: PRT
<213> ORGANISM: Artificial Sequence
<220> FEATURE:
<223> OTHER INFORMATION: peptide having a specific affinity for a
      hydrophilic solid surface

<400> SEQUENCE: 7

Arg Gly Gly Gly Arg Arg Gly Arg Arg
 1               5

<210> SEQ ID NO 8
<211> LENGTH: 9
<212> TYPE: PRT
<213> ORGANISM: Artificial Sequence
<220> FEATURE:
<223> OTHER INFORMATION: peptide having a specific affinity for a
      hydrophilic solid surface

<400> SEQUENCE: 8

Arg Met Met Met Arg Arg Met Arg Arg
 1               5

<210> SEQ ID NO 9
```

```
<211> LENGTH: 9
<212> TYPE: PRT
<213> ORGANISM: Artificial Sequence
<220> FEATURE:
<223> OTHER INFORMATION: peptide having a specific affinity for a
      hydrophilic solid surface

<400> SEQUENCE: 9

Arg Ser Ser Ser Arg Arg Ser Arg Arg
1               5

<210> SEQ ID NO 10
<211> LENGTH: 9
<212> TYPE: PRT
<213> ORGANISM: Artificial Sequence
<220> FEATURE:
<223> OTHER INFORMATION: peptide having a specific affinity for a
      hydrophilic solid surface

<400> SEQUENCE: 10

Arg Thr Thr Thr Arg Arg Thr Arg Arg
1               5

<210> SEQ ID NO 11
<211> LENGTH: 12
<212> TYPE: PRT
<213> ORGANISM: Artificial Sequence
<220> FEATURE:
<223> OTHER INFORMATION: peptide having a specific affinity for a
      hydrophilic solid surface
<300> PUBLICATION INFORMATION:
<301> AUTHORS: Sakiyama et al.,
<302> TITLE: Use of a novel affinity tag selected with a bacterial
      random peptide library for improving activity retention of
      glutathione S-transferase adsorbed on a polystyrene surface
<303> JOURNAL: Journal of Molecular Catalysis B:Enzymatic
<304> VOLUME: 28
<305> ISSUE: 4-6
<306> PAGES: 207-214

<400> SEQUENCE: 11

Lys Gly Leu Arg Gly Trp Arg Glu Met Ile Ser Leu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: peptide having a specific affinity for a
      hydrophilic solid surface
<300> PUBLICATION INFORMATION:
<301> AUTHORS: kumada et al.,
<302> TITLE: Screening and characterization of affinity peptide tags
      specific to polystyrene supports for the orientated immobilization
      of proteins
<303> JOURNAL: Biotechnology Progress
<304> VOLUME: 22
<305> ISSUE: 2
<306> PAGES: 401-405

<400> SEQUENCE: 12

Ala Asp Tyr Leu Ser Arg Trp Gly Ser Ile Arg Asn
1               5                   10

<210> SEQ ID NO 13
<211> LENGTH: 12
<212> TYPE: PRT
<213> ORGANISM: Artificial Sequence
<220> FEATURE:
<223> OTHER INFORMATION: peptide having a specific affinity for a
      hydrophilic solid surface
```

```
<300> PUBLICATION INFORMATION:
<301> AUTHORS: kumada et al.,
<302> TITLE: Screening and characterization of affinity peptide tags
      specific to polystyrene supports for the orientated immobilization
      of proteins
<303> JOURNAL: Biotechnology Progress
<304> VOLUME: 22
<305> ISSUE: 2
<306> PAGES: 401-405

<400> SEQUENCE: 13

Ser Arg Val His Arg Ala Val Leu Asn Gly Val Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: peptide having a specific affinity for a
      hydrophilic solid surface
<300> PUBLICATION INFORMATION:
<301> AUTHORS: kumada et al.,
<302> TITLE: Screening and characterization of affinity peptide tags
      specific to polystyrene supports for the orientated immobilization
      of proteins
<303> JOURNAL: Biotechnology Progress
<304> VOLUME: 22
<305> ISSUE: 2
<306> PAGES: 401-405

<400> SEQUENCE: 14

Arg Pro Pro Gly Val Val Arg Arg Tyr Ala Leu Gly
1               5                   10

<210> SEQ ID NO 15
<211> LENGTH: 12
<212> TYPE: PRT
<213> ORGANISM: Artificial Sequence
<220> FEATURE:
<223> OTHER INFORMATION: peptide having a specific affinity for a
      hydrophilic solid surface
<300> PUBLICATION INFORMATION:
<301> AUTHORS: kumada et al.,
<302> TITLE: Screening and characterization of affinity peptide tags
      specific to polystyrene supports for the orientated immobilization
      of proteins
<303> JOURNAL: Biotechnology Progress
<304> VOLUME: 22
<305> ISSUE: 2
<306> PAGES: 401-405

<400> SEQUENCE: 15

Val Arg Ser Trp Glu Glu Gln Ala Arg Val Thr Thr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: peptide having a specific affinity for a
      hydrophilic solid surface
<300> PUBLICATION INFORMATION:
<301> AUTHORS: kumada et al.,
<302> TITLE: Screening and characterization of affinity peptide tags
      specific to polystyrene supports for the orientated immobilization
      of proteins
<303> JOURNAL: Biotechnology Progress
<304> VOLUME: 22
<305> ISSUE: 2
<306> PAGES: 401-405

<400> SEQUENCE: 16
```

```
Arg Ala Phe Ile Ala Ser Arg Arg Ile Lys Arg Pro
 1               5                  10
```

<210> SEQ ID NO 17
<211> LENGTH: 12
<212> TYPE: PRT
<213> ORGANISM: Artificial Sequence
<220> FEATURE:
<223> OTHER INFORMATION: peptide having a specific affinity for a
      hydrophilic solid surface
<300> PUBLICATION INFORMATION:
<301> AUTHORS: kumada et al.,
<302> TITLE: Screening and characterization of affinity peptide tags
      specific to polystyrene supports for the orientated immobilization
      of proteins
<303> JOURNAL: Biotechnology Progress
<304> VOLUME: 22
<305> ISSUE: 2
<306> PAGES: 401-405

<400> SEQUENCE: 17

```
Arg Glu Ser Thr Leu Lys Gly Thr Ser Arg Ala Val
 1               5                  10
```

<210> SEQ ID NO 18
<211> LENGTH: 12
<212> TYPE: PRT
<213> ORGANISM: Artificial Sequence
<220> FEATURE:
<223> OTHER INFORMATION: peptide having a specific affinity for a
      hydrophilic solid surface
<300> PUBLICATION INFORMATION:
<301> AUTHORS: kumada et al.,
<302> TITLE: Screening and characterization of affinity peptide tags
      specific to polystyrene supports for the orientated immobilization
      of proteins
<303> JOURNAL: Biotechnology Progress
<304> VOLUME: 22
<305> ISSUE: 2
<306> PAGES: 401-405

<400> SEQUENCE: 18

```
Ala Gly Leu Arg Leu Lys Lys Ala Ala Ile His Arg
 1               5                  10
```

<210> SEQ ID NO 19
<211> LENGTH: 12
<212> TYPE: PRT
<213> ORGANISM: Artificial Sequence
<220> FEATURE:
<223> OTHER INFORMATION: peptide having a specific affinity for a
      hydrophilic solid surface
<300> PUBLICATION INFORMATION:
<301> AUTHORS: kumada et al.,
<302> TITLE: Screening and characterization of affinity peptide tags
      specific to polystyrene supports for the orientated immobilization
      of proteins
<303> JOURNAL: Biotechnology Progress
<304> VOLUME: 22
<305> ISSUE: 2
<306> PAGES: 401-405

<400> SEQUENCE: 19

```
Ser Ser Leu Leu Arg Ala Val Pro Glu Pro Thr Gly
 1               5                  10
```

<210> SEQ ID NO 20
<211> LENGTH: 12
<212> TYPE: PRT
<213> ORGANISM: Artificial Sequence
<220> FEATURE:
<223> OTHER INFORMATION: peptide having a specific affinity for a

```
                          hydrophilic solid surface
<300> PUBLICATION INFORMATION:
<301> AUTHORS: kumada et al.,
<302> TITLE: Development of a one-step ELISA method using an affinity
      peptide tag specific to a hydrophilic polystyrene surface
<303> JOURNAL: Journal of Biotechnology
<304> VOLUME: 127
<305> ISSUE: 2
<306> PAGES: 288-299

<400> SEQUENCE: 20

Arg Ala Phe Ile Ala Ser Arg Arg Ile Arg Arg Pro
  1               5               ?   10

<210> SEQ ID NO 21
<211> LENGTH: 27
<212> TYPE: DNA
<213> ORGANISM: Artificial Sequence
<220> FEATURE:
<223> OTHER INFORMATION: synthetic DNA

<400> SEQUENCE: 21
cgtatcatca tccgaaggat tcgacga                                            27

<210> SEQ ID NO 22
<211> LENGTH: 27
<212> TYPE: DNA
<213> ORGANISM: Artificial Sequence
<220> FEATURE:
<223> OTHER INFORMATION: synthetic DNA

<400> SEQUENCE: 22
cgtgcgattg cgcgaaggat tcgacga                                            27

<210> SEQ ID NO 23
<211> LENGTH: 265
<212> TYPE: PRT
<213> ORGANISM: Artificial Sequence
<220> FEATURE:
<223> OTHER INFORMATION: single chain antibody

<400> SEQUENCE: 23

Met Ala Ser Gln Val Gln Leu Gln Gln Ser Gly Ala Glu Leu Val Lys
  1               5                  10                  15

Pro Gly Ala Ser Val Lys Leu Ser Cys Thr Ala Ser Gly Phe Asn Ile
             20                  25                  30

Lys Asp Tyr Tyr Met His Trp Val Lys Gln Arg Thr Glu Gln Gly Leu
         35                  40                  45

Glu Trp Ile Gly Arg Ile Asp Pro Glu Asp Gly Glu Thr Lys Tyr Ala
     50                  55                  60

Pro Lys Phe Gln Gly Lys Ala Thr Ile Thr Ala Asp Thr Ser Ser Asn
 65                  70                  75                  80

Thr Ala Tyr Leu Gln Leu Ser Ser Leu Thr Ser Glu Asp Thr Ala Val
                 85                  90                  95

Tyr Tyr Cys Ala Arg Gly Tyr Tyr Gly Ser Glu Ala Met Asp Tyr Trp
            100                 105                 110

Gly Gln Gly Thr Ser Leu Thr Val Ser Ser Gly Gly Gly Gly Ser Gly
        115                 120                 125

Gly Gly Gly Ser Gly Gly Gly Gly Ser Thr Gly Ser Ile Val Met Thr
    130                 135                 140

Gln Ser His Lys Phe Met Ser Thr Ser Val Gly Asp Arg Val Ser Ile
145                 150                 155                 160
```

```
Thr Cys Lys Ala Ser Gln Asp Val Asn Thr Ala Val Ala Trp Tyr Gln
            165                 170                 175

Gln Lys Pro Gly Gln Ser Pro Lys Leu Leu Ile Tyr Trp Ala Ser Thr
            180                 185                 190

Arg His Thr Gly Val Pro Asp Arg Phe Thr Gly Ser Gly Phe Gly Thr
            195                 200                 205

Asp Tyr Thr Leu Thr Ile Ser Ser Val Gln Ala Glu Asp Leu Ala Leu
            210                 215                 220

Tyr Tyr Cys Gln Gln His Tyr Ser Thr Pro Trp Thr Phe Gly Gly Gly
225                 230                 235                 240

Thr Lys Leu Glu Ile Lys Arg Ala Asp Ala Ala Pro Thr Val Ala Ala
            245                 250                 255

Ala Leu Glu His His His His His His
            260                 265

<210> SEQ ID NO 24
<211> LENGTH: 269
<212> TYPE: PRT
<213> ORGANISM: Artificial Sequence
<220> FEATURE:
<223> OTHER INFORMATION: single chain antibody

<400> SEQUENCE: 24

Met Ala Ser Glu Val Lys Leu Met Glu Ser Gly Gly Gly Leu Val Gln
1               5                   10                  15

Pro Gly Gly Ser Leu Lys Leu Ser Cys Ala Ala Ser Gly Phe Thr Phe
            20                  25                  30

Ser Ser Tyr Gly Met Ser Trp Val Arg Gln Thr Pro Asp Lys Arg Leu
            35                  40                  45

Glu Leu Val Ala Thr Ile Asn Ser Asn Gly Gly Ser Thr Tyr Tyr Pro
50                  55                  60

Asp Ser Val Lys Gly Arg Phe Thr Ile Ser Arg Asp Asn Ala Lys Asn
65                  70                  75                  80

Thr Leu Tyr Leu Gln Met Ser Ser Leu Lys Ser Glu Asp Thr Ala Met
            85                  90                  95

Tyr Tyr Cys Ala Arg Gly Gly Arg Leu Arg Leu Tyr Phe Asp Val Trp
            100                 105                 110

Gly Ala Gly Thr Ser Leu Thr Val Ser Ser Gly Gly Gly Gly Ser Gly
            115                 120                 125

Gly Gly Gly Ser Gly Gly Gly Gly Ser Thr Gly Asp Ile Val Met Ser
130                 135                 140

Gln Ser Pro Ala Ser Leu Ala Val Ser Leu Gly Gln Arg Ala Thr Ile
145                 150                 155                 160

Ser Cys Arg Ala Ser Gln Ser Val Ser Thr Ser Ser Tyr Ser Tyr Met
            165                 170                 175

His Trp Tyr Gln Gln Lys Pro Gly Gln Pro Pro Lys Leu Leu Ile Lys
            180                 185                 190

Tyr Ala Ser Asn Leu Glu Ser Gly Val Pro Ala Arg Phe Ser Gly Ser
            195                 200                 205

Gly Ser Gly Thr Asp Phe Thr Leu Asn Ile His Pro Val Glu Glu Glu
            210                 215                 220

Asp Thr Ala Thr Tyr Tyr Cys Gln His Ser Trp Glu Ile Pro Tyr Thr
225                 230                 235                 240

Phe Gly Gly Gly Thr Lys Leu Glu Ile Lys Arg Ala Asp Ala Ala Pro
            245                 250                 255
```

Thr Val Ala Ala Ala Leu Glu His His His His His
                260                 265

<210> SEQ ID NO 25
<211> LENGTH: 265
<212> TYPE: PRT
<213> ORGANISM: Artificial Sequence
<220> FEATURE:
<223> OTHER INFORMATION: single chain antibody

<400> SEQUENCE: 25

Met Ala Ser Gln Val Gln Leu Gln Gln Ser Gly Ala Glu Leu Val Lys
1               5                   10                  15

Pro Gly Ala Ser Val Lys Leu Ser Cys Thr Ala Ser Gly Phe Asn Ile
            20                  25                  30

Lys Asp Tyr Tyr Met His Trp Val Lys Gln Arg Thr Glu Gln Gly Leu
        35                  40                  45

Glu Trp Ile Gly Arg Ile Asp Pro Glu Asp Gly Glu Thr Lys Tyr Ala
    50                  55                  60

Pro Lys Phe Gln Gly Lys Ala Thr Ile Thr Ala Asp Thr Ser Ser Asn
65                  70                  75                  80

Thr Ala Tyr Leu Gln Leu Ser Ser Leu Thr Ser Glu Asn Thr Ala Val
                85                  90                  95

Tyr Tyr Cys Ala Arg Gly Tyr Tyr Gly Ser Glu Ala Met Asp Tyr Trp
            100                 105                 110

Gly Gln Gly Thr Ser Val Thr Val Ser Ser Gly Arg Gly Gly Ser Gly
        115                 120                 125

Gly Gly Gly Ser Gly Gly Gly Ser Thr Gly Asp Ile Leu Met Thr
        130                 135                 140

Gln Ser His Lys Phe Met Ser Thr Ser Val Gly Asp Arg Val Ser Ile
145                 150                 155                 160

Thr Cys Lys Ala Ser Gln Asp Val Ser Thr Ala Val Ala Trp Tyr Gln
                165                 170                 175

Gln Lys Pro Gly Gln Ser Pro Lys Leu Leu Ile Tyr Trp Ala Ser Thr
            180                 185                 190

Arg His Thr Gly Val Pro Asp Arg Phe Thr Gly Ser Gly Ser Gly Thr
        195                 200                 205

Asp Tyr Thr Leu Thr Ile Ser Ser Val Gln Ala Glu Asp Leu Ala Leu
    210                 215                 220

Tyr Tyr Cys Gln Gln His Tyr Ser Thr Pro Trp Thr Phe Gly Gly Gly
225                 230                 235                 240

Thr Lys Leu Glu Ile Lys Arg Ala Asp Ala Ala Pro Thr Val Ala Ala
                245                 250                 255

Ala Leu Glu His His His His His
            260                 265

<210> SEQ ID NO 26
<211> LENGTH: 274
<212> TYPE: PRT
<213> ORGANISM: Artificial Sequence
<220> FEATURE:
<223> OTHER INFORMATION: single chain antibody having a specific
      affinity for a hydrophilic solid surface

<400> SEQUENCE: 26

Met Ala Ser Gln Val Gln Leu Gln Gln Ser Gly Ala Glu Leu Val Lys
1               5                   10                  15

Pro Gly Ala Ser Val Lys Leu Ser Cys Thr Ala Ser Gly Phe Asn Ile
            20                  25                  30

Lys Asp Tyr Tyr Met His Trp Val Lys Gln Arg Thr Glu Gln Gly Leu
            35                  40                  45

Glu Trp Ile Gly Arg Ile Asp Pro Glu Asp Gly Glu Thr Lys Tyr Ala
 50                  55                  60

Pro Lys Phe Gln Gly Lys Ala Thr Ile Thr Ala Asp Thr Ser Ser Asn
 65                  70                  75                  80

Thr Ala Tyr Leu Gln Leu Ser Ser Leu Thr Ser Glu Asp Thr Ala Val
                85                  90                  95

Tyr Tyr Cys Ala Arg Gly Tyr Tyr Gly Ser Glu Ala Met Asp Tyr Trp
            100                 105                 110

Gly Gln Gly Thr Ser Leu Thr Val Ser Ser Gly Gly Gly Ser Gly
            115                 120                 125

Gly Gly Gly Ser Gly Gly Gly Ser Thr Gly Ser Ile Val Met Thr
    130                 135                 140

Gln Ser His Lys Phe Met Ser Thr Ser Val Gly Asp Arg Val Ser Ile
145                 150                 155                 160

Thr Cys Lys Ala Ser Gln Asp Val Asn Thr Ala Val Ala Trp Tyr Gln
                165                 170                 175

Gln Lys Pro Gly Gln Ser Pro Lys Leu Leu Ile Tyr Trp Ala Ser Thr
            180                 185                 190

Arg His Thr Gly Val Pro Asp Arg Phe Thr Gly Ser Gly Phe Gly Thr
        195                 200                 205

Asp Tyr Thr Leu Thr Ile Ser Ser Val Gln Ala Glu Asp Leu Ala Leu
    210                 215                 220

Tyr Tyr Cys Gln Gln His Tyr Ser Thr Pro Trp Thr Phe Gly Gly Gly
225                 230                 235                 240

Thr Lys Leu Glu Ile Lys Arg Ala Asp Ala Ala Pro Thr Val Ala Ala
                245                 250                 255

Ala Arg Ile Ile Ile Arg Arg Ile Arg Arg Ile Glu His His His His
            260                 265                 270

His His

<210> SEQ ID NO 27
<211> LENGTH: 278
<212> TYPE: PRT
<213> ORGANISM: Artificial Sequence
<220> FEATURE:
<223> OTHER INFORMATION: single chain antibody having a specific
      affinity for a hydrophilic solid surface

<400> SEQUENCE: 27

Met Ala Ser Glu Val Lys Leu Met Glu Ser Gly Gly Gly Leu Val Gln
 1               5                  10                  15

Pro Gly Gly Ser Leu Lys Leu Ser Cys Ala Ala Ser Gly Phe Thr Phe
            20                  25                  30

Ser Ser Tyr Gly Met Ser Trp Val Arg Gln Thr Pro Asp Lys Arg Leu
        35                  40                  45

Glu Leu Val Ala Thr Ile Asn Ser Asn Gly Gly Ser Thr Tyr Tyr Pro
 50                  55                  60

Asp Ser Val Lys Gly Arg Phe Thr Ile Ser Arg Asp Asn Ala Lys Asn
 65                  70                  75                  80

Thr Leu Tyr Leu Gln Met Ser Ser Leu Lys Ser Glu Asp Thr Ala Met
                85                  90                  95

Tyr Tyr Cys Ala Arg Gly Gly Arg Leu Arg Leu Tyr Phe Asp Val Trp
            100                 105                 110

```
Gly Ala Gly Thr Ser Leu Thr Val Ser Ser Gly Gly Gly Ser Gly
            115                 120                 125

Gly Gly Gly Ser Gly Gly Gly Ser Thr Gly Asp Ile Val Met Ser
130                 135                 140

Gln Ser Pro Ala Ser Leu Ala Val Ser Leu Gly Gln Arg Ala Thr Ile
145                 150                 155                 160

Ser Cys Arg Ala Ser Gln Ser Val Ser Thr Ser Ser Tyr Ser Tyr Met
                165                 170                 175

His Trp Tyr Gln Gln Lys Pro Gly Gln Pro Pro Lys Leu Leu Ile Lys
                180                 185                 190

Tyr Ala Ser Asn Leu Glu Ser Gly Val Pro Ala Arg Phe Ser Gly Ser
                195                 200                 205

Gly Ser Gly Thr Asp Phe Thr Leu Asn Ile His Pro Val Glu Glu Glu
            210                 215                 220

Asp Thr Ala Thr Tyr Tyr Cys Gln His Ser Trp Glu Ile Pro Tyr Thr
225                 230                 235                 240

Phe Gly Gly Gly Thr Lys Leu Glu Ile Lys Arg Ala Asp Ala Ala Pro
                245                 250                 255

Thr Val Ala Ala Ala Arg Ile Ile Ile Arg Arg Ile Arg Ile Glu
                260                 265                 270

His His His His His His
            275

<210> SEQ ID NO 28
<211> LENGTH: 274
<212> TYPE: PRT
<213> ORGANISM: Artificial Sequence
<220> FEATURE:
<223> OTHER INFORMATION: single chain antibody having a specific
      affinity for a hydrophilic solid surface

<400> SEQUENCE: 28

Met Ala Ser Gln Val Gln Leu Gln Gln Ser Gly Ala Glu Leu Val Lys
 1               5                  10                  15

Pro Gly Ala Ser Val Lys Leu Ser Cys Thr Ala Ser Gly Phe Asn Ile
                20                  25                  30

Lys Asp Tyr Tyr Met His Trp Val Lys Gln Arg Thr Glu Gln Gly Leu
            35                  40                  45

Glu Trp Ile Gly Arg Ile Asp Pro Glu Asp Gly Glu Thr Lys Tyr Ala
        50                  55                  60

Pro Lys Phe Gln Gly Lys Ala Thr Ile Thr Ala Asp Thr Ser Ser Asn
65                  70                  75                  80

Thr Ala Tyr Leu Gln Leu Ser Ser Leu Thr Ser Glu Asn Thr Ala Val
                85                  90                  95

Tyr Tyr Cys Ala Arg Gly Tyr Tyr Gly Ser Glu Ala Met Asp Tyr Trp
                100                 105                 110

Gly Gln Gly Thr Ser Val Thr Val Ser Ser Gly Arg Gly Gly Ser Gly
            115                 120                 125

Gly Gly Gly Ser Gly Gly Gly Ser Thr Gly Asp Ile Leu Met Thr
130                 135                 140

Gln Ser His Lys Phe Met Ser Thr Ser Val Gly Asp Arg Val Ser Ile
145                 150                 155                 160

Thr Cys Lys Ala Ser Gln Asp Val Ser Thr Ala Val Ala Trp Tyr Gln
                165                 170                 175

Gln Lys Pro Gly Gln Ser Pro Lys Leu Leu Ile Tyr Trp Ala Ser Thr
                180                 185                 190
```

```
Arg His Thr Gly Val Pro Asp Arg Phe Thr Gly Ser Gly Ser Gly Thr
        195                 200                 205

Asp Tyr Thr Leu Thr Ile Ser Ser Val Gln Ala Glu Asp Leu Ala Leu
    210                 215                 220

Tyr Tyr Cys Gln Gln His Tyr Ser Thr Pro Trp Thr Phe Gly Gly Gly
225                 230                 235                 240

Thr Lys Leu Glu Ile Lys Arg Ala Asp Ala Ala Pro Thr Val Ala Ala
            245                 250                 255

Ala Arg Ile Ile Ile Arg Arg Ile Arg Arg Ile Glu His His His His
            260                 265                 270

His His
```

<210> SEQ ID NO 29
<211> LENGTH: 274
<212> TYPE: PRT
<213> ORGANISM: Artificial Sequence
<220> FEATURE:
<223> OTHER INFORMATION: single chain antibody having a specific affinity for a hydrophilic solid surface

<400> SEQUENCE: 29

```
Met Ala Ser Gln Val Gln Leu Gln Gln Ser Gly Ala Glu Leu Val Lys
 1               5                  10                  15

Pro Gly Ala Ser Val Lys Leu Ser Cys Thr Ala Ser Gly Phe Asn Ile
             20                  25                  30

Lys Asp Tyr Tyr Met His Trp Val Lys Gln Arg Thr Glu Gln Gly Leu
         35                  40                  45

Glu Trp Ile Gly Arg Ile Asp Pro Glu Asp Gly Glu Thr Lys Tyr Ala
 50                  55                  60

Pro Lys Phe Gln Gly Lys Ala Thr Ile Thr Ala Asp Thr Ser Ser Asn
65                   70                  75                  80

Thr Ala Tyr Leu Gln Leu Ser Ser Leu Thr Ser Glu Asp Thr Ala Val
                 85                  90                  95

Tyr Tyr Cys Ala Arg Gly Tyr Tyr Gly Ser Glu Ala Met Asp Tyr Trp
            100                 105                 110

Gly Gln Gly Thr Ser Leu Thr Val Ser Ser Arg Ile Ile Ile Arg Arg
        115                 120                 125

Ile Arg Arg Gly Gly Gly Ser Gly Gly Gly Ser Gly Gly
130                 135                 140

Gly Ser Thr Gly Ser Ile Val Met Thr Gln Ser His Lys Phe Met Ser
145                 150                 155                 160

Thr Ser Val Gly Asp Arg Val Ser Ile Thr Cys Lys Ala Ser Gln Asp
                165                 170                 175

Val Asn Thr Ala Val Ala Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Phe Gly Thr Asp Tyr Thr Leu Thr Ile Ser
    210                 215                 220

Ser Val Gln Ala Glu Asp Leu Ala Leu Tyr Tyr Cys Gln Gln His Tyr
225                 230                 235                 240

Ser Thr Pro Trp Thr Phe Gly Gly Gly Thr Lys Leu Glu Ile Lys Arg
                245                 250                 255

Ala Asp Ala Ala Pro Thr Val Ala Ala Ala Leu Glu His His His His
            260                 265                 270

His His
```

<210> SEQ ID NO 30
<211> LENGTH: 278
<212> TYPE: PRT
<213> ORGANISM: Artificial Sequence
<220> FEATURE:
<223> OTHER INFORMATION: single chain antibody having a specific
      affinity for a hydrophilic solid surface

<400> SEQUENCE: 30

```
Met Ala Ser Glu Val Lys Leu Met Glu Ser Gly Gly Leu Val Gln
1               5                   10                  15

Pro Gly Gly Ser Leu Lys Leu Ser Cys Ala Ala Ser Gly Phe Thr Phe
                20                  25                  30

Ser Ser Tyr Gly Met Ser Trp Val Arg Gln Thr Pro Asp Lys Arg Leu
            35                  40                  45

Glu Leu Val Ala Thr Ile Asn Ser Asn Gly Gly Ser Thr Tyr Tyr Pro
        50                  55                  60

Asp Ser Val Lys Gly Arg Phe Thr Ile Ser Arg Asp Asn Ala Lys Asn
65                  70                  75                  80

Thr Leu Tyr Leu Gln Met Ser Ser Leu Lys Ser Glu Asp Thr Ala Met
                85                  90                  95

Tyr Tyr Cys Ala Arg Gly Gly Arg Leu Arg Leu Tyr Phe Asp Val Trp
            100                 105                 110

Gly Ala Gly Thr Ser Leu Thr Val Ser Ser Arg Ile Ile Ile Arg Arg
        115                 120                 125

Ile Arg Arg Gly Gly Gly Ser Gly Gly Gly Ser Gly Gly Gly
130                 135                 140

Gly Ser Thr Gly Asp Ile Val Met Ser Gln Ser Pro Ala Ser Leu Ala
145                 150                 155                 160

Val Ser Leu Gly Gln Arg Ala Thr Ile Ser Cys Arg Ala Ser Gln Ser
                165                 170                 175

Val Ser Thr Ser Ser Tyr Ser Tyr Met His Trp Tyr Gln Gln Lys Pro
            180                 185                 190

Gly Gln Pro Pro Lys Leu Leu Ile Lys Tyr Ala Ser Asn Leu Glu Ser
        195                 200                 205

Gly Val Pro Ala Arg Phe Ser Gly Ser Gly Ser Gly Thr Asp Phe Thr
        210                 215                 220

Leu Asn Ile His Pro Val Glu Glu Asp Thr Ala Thr Tyr Tyr Cys
225                 230                 235                 240

Gln His Ser Trp Glu Ile Pro Tyr Thr Phe Gly Gly Gly Thr Lys Leu
                245                 250                 255

Glu Ile Lys Arg Ala Asp Ala Ala Pro Thr Val Ala Ala Ala Leu Glu
            260                 265                 270

His His His His His His
        275
```

<210> SEQ ID NO 31
<211> LENGTH: 283
<212> TYPE: PRT
<213> ORGANISM: Artificial Sequence
<220> FEATURE:
<223> OTHER INFORMATION: single chain antibody having a specific
      affinity for a hydrophilic solid surface

<400> SEQUENCE: 31

```
Met Ala Ser Gln Val Gln Leu Gln Gln Ser Gly Ala Glu Leu Val Lys
1               5                   10                  15
```

```
Pro Gly Ala Ser Val Lys Leu Ser Cys Thr Ala Ser Gly Phe Asn Ile
            20                  25                  30

Lys Asp Tyr Tyr Met His Trp Val Lys Gln Arg Thr Glu Gln Gly Leu
        35                  40                  45

Glu Trp Ile Gly Arg Ile Asp Pro Glu Asp Gly Glu Thr Lys Tyr Ala
 50                  55                  60

Pro Lys Phe Gln Gly Lys Ala Thr Ile Thr Ala Asp Thr Ser Ser Asn
 65                  70                  75                  80

Thr Ala Tyr Leu Gln Leu Ser Ser Leu Thr Ser Glu Asp Thr Ala Val
            85                  90                  95

Tyr Tyr Cys Ala Arg Gly Tyr Tyr Gly Ser Ala Met Asp Tyr Trp
            100                 105                 110

Gly Gln Gly Thr Ser Leu Thr Val Ser Ser Arg Ile Ile Ile Arg Arg
            115                 120                 125

Ile Arg Arg Gly Gly Gly Ser Gly Gly Gly Ser Gly Gly Gly
        130                 135                 140

Gly Ser Thr Gly Ser Ile Val Met Thr Gln Ser His Lys Phe Met Ser
145                 150                 155                 160

Thr Ser Val Gly Asp Arg Val Ser Ile Thr Cys Lys Ala Ser Gln Asp
                165                 170                 175

Val Asn Thr Ala Val Ala Trp Tyr Gln Gln Lys Pro Gly Gln Ser Pro
            180                 185                 190

Lys Leu Leu Ile Tyr Trp Ala Ser Thr Arg His Thr Gly Val Pro Asp
        195                 200                 205

Arg Phe Thr Gly Ser Gly Phe Gly Thr Asp Tyr Thr Leu Thr Ile Ser
        210                 215                 220

Ser Val Gln Ala Glu Asp Leu Ala Leu Tyr Tyr Cys Gln Gln His Tyr
225                 230                 235                 240

Ser Thr Pro Trp Thr Phe Gly Gly Thr Lys Leu Glu Ile Lys Arg
            245                 250                 255

Ala Asp Ala Ala Pro Thr Val Ala Ala Arg Ile Ile Ile Arg Arg
            260                 265                 270

Ile Arg Arg Ile Glu His His His His His His
        275                 280

<210> SEQ ID NO 32
<211> LENGTH: 287
<212> TYPE: PRT
<213> ORGANISM: Artificial Sequence
<220> FEATURE:
<223> OTHER INFORMATION: single chain antibody having a specific
      affinity for a hydrophilic solid surface

<400> SEQUENCE: 32

Met Ala Ser Glu Val Lys Leu Met Glu Ser Gly Gly Gly Leu Val Gln
 1               5                   10                  15

Pro Gly Gly Ser Leu Lys Leu Ser Cys Ala Ala Ser Gly Phe Thr Phe
            20                  25                  30

Ser Ser Tyr Gly Met Ser Trp Val Arg Gln Thr Pro Asp Lys Arg Leu
        35                  40                  45

Glu Leu Val Ala Thr Ile Asn Ser Asn Gly Gly Ser Thr Tyr Tyr Pro
 50                  55                  60

Asp Ser Val Lys Gly Arg Phe Thr Ile Ser Arg Asp Asn Ala Lys Asn
 65                  70                  75                  80

Thr Leu Tyr Leu Gln Met Ser Ser Leu Lys Ser Glu Asp Thr Ala Met
            85                  90                  95
```

-continued

```
Tyr Tyr Cys Ala Arg Gly Gly Arg Leu Arg Leu Tyr Phe Asp Val Trp
            100                 105                 110

Gly Ala Gly Thr Ser Leu Thr Val Ser Ser Arg Ile Ile Ile Arg Arg
            115                 120                 125

Ile Arg Arg Gly Gly Gly Ser Gly Gly Gly Ser Gly Gly Gly
            130                 135                 140

Gly Ser Thr Gly Asp Ile Val Met Ser Gln Ser Pro Ala Ser Leu Ala
145                 150                 155                 160

Val Ser Leu Gly Gln Arg Ala Thr Ile Ser Cys Arg Ala Ser Gln Ser
                165                 170                 175

Val Ser Thr Ser Ser Tyr Ser Tyr Met His Trp Tyr Gln Gln Lys Pro
                180                 185                 190

Gly Gln Pro Pro Lys Leu Leu Ile Lys Tyr Ala Ser Asn Leu Glu Ser
                195                 200                 205

Gly Val Pro Ala Arg Phe Ser Gly Ser Gly Ser Gly Thr Asp Phe Thr
            210                 215                 220

Leu Asn Ile His Pro Val Glu Glu Glu Asp Thr Ala Thr Tyr Tyr Cys
225                 230                 235                 240

Gln His Ser Trp Glu Ile Pro Tyr Thr Phe Gly Gly Gly Thr Lys Leu
                245                 250                 255

Glu Ile Lys Arg Ala Asp Ala Ala Pro Thr Val Ala Ala Ala Arg Ile
                260                 265                 270

Ile Ile Arg Arg Ile Arg Arg Ile Glu His His His His His His
            275                 280                 285

<210> SEQ ID NO 33
<211> LENGTH: 10
<212> TYPE: PRT
<213> ORGANISM: Artificial Sequence
<220> FEATURE:
<223> OTHER INFORMATION: modified peptide having a specific affinity
      for a hydrophilic solid surface

<400> SEQUENCE: 33

Lys Arg Ile Ile Ile Arg Arg Ile Arg Arg
1               5                   10
```